US008410335B2

(12) United States Patent
Tanaka et al.

(10) Patent No.: US 8,410,335 B2
(45) Date of Patent: Apr. 2, 2013

(54) METHOD FOR PRODUCING ROSE WITH ALTERED PETAL COLORS

(75) Inventors: Yoshikazu Tanaka, Otsu (JP); Yuko Fukui, Takatsuki (JP); Junichi Togami, Takatsuki (JP); Yukihisa Katsumoto, Osaka (JP); Masako Mizutani, Kyoto (JP)

(73) Assignee: Suntory Holdings Limited, Osaka (JP)

( * ) Notice: Subject to any disclaimer, the term of this patent is extended or adjusted under 35 U.S.C. 154(b) by 1805 days.

(21) Appl. No.: 10/567,931

(22) PCT Filed: Aug. 13, 2004

(86) PCT No.: PCT/JP2004/011958
§ 371 (c)(1),
(2), (4) Date: Oct. 24, 2006

(87) PCT Pub. No.: WO2005/017147
PCT Pub. Date: Feb. 24, 2005

(65) Prior Publication Data
US 2011/0126320 A1    May 26, 2011

(30) Foreign Application Priority Data

Aug. 13, 2003  (JP) ................................. 2003-293121
Jun. 29, 2004  (JP) ................................. 2004-192034

(51) Int. Cl.
C12N 15/82   (2006.01)
C12N 15/113  (2010.01)
C12N 15/29   (2006.01)
C12N 5/10    (2006.01)
A01H 5/00    (2006.01)
(52) U.S. Cl. .......................... 800/282; 800/285; 800/323
(58) Field of Classification Search .................. 800/282
See application file for complete search history.

(56) References Cited

U.S. PATENT DOCUMENTS

| | | | |
|---|---|---|---|
| 5,480,789 A | | 1/1996 | Firoozabady et al. |
| 5,568,832 A | * | 10/1996 | Eddy ............................. 160/374 |
| 5,792,927 A | | 8/1998 | Firoozabady et al. |
| 5,948,955 A | * | 9/1999 | Holton et al. ................. 800/298 |
| 6,080,920 A | * | 6/2000 | Holton ........................ 800/323.3 |
| 6,114,601 A | | 9/2000 | Kikuchi et al. |
| 6,232,109 B1 | | 5/2001 | Kikuchi et al. |
| 7,105,719 B1 | | 9/2006 | Ashikari et al. |
| 2001/0007157 A1 | | 7/2001 | Firoozabady et al. |
| 2002/0100072 A1 | | 7/2002 | Kikuchi et al. |

FOREIGN PATENT DOCUMENTS

| | | |
|---|---|---|
| EP | 0 522 880 A2 | 1/1993 |
| EP | 0 536 327 | 4/1993 |
| EP | 0 632 128 A1 | 1/1995 |
| EP | 1 652 916 A1 | 5/2006 |
| JP | 2002-16935 | 1/2002 |
| JP | 2002-201372 | 7/2002 |
| WO | WO 94/28140 | 12/1994 |
| WO | WO 96/36716 | 11/1996 |
| WO | WO 97/32023 | 9/1997 |
| WO | WO 03/062428 | 7/2003 |
| WO | WO 2004/020637 A1 | 3/2004 |

OTHER PUBLICATIONS

Mol et al. "Novel coloured flowers" 1999, Current Opinion in Biotechnology 10: 198-201.*
Suzuki et al. "Flower color modifications of *Torenia hybrida* by cosuppression of anthocyanin biosynthesis genes", 2000, Molecular Breeding 6: 239-246.*
Tanaka et al. "Metabolic Engineering to Modify Flower Color", 1998, Plant Cell Physiol. 39(11): 1119-1126.*
European Search Report dated May 6, 2009, for corresponding European application 04771919.0.
Mol, JNM, et al., *Floriculture: genetic engineering of commercial traits*, TIBTECH, transgenics, vol. 13, Sep. 1995, pp. 350-355, XP 4207200A.
Patent Abstracts of Japan, Publication No. 2002-016935; Date of Publication: Jan. 18, 2002; in the name of Shinji Shibano, et al.
Patent Abstracts of Japan, Publication No. 2002-201372; Date of Publication: Jul. 19, 2002; in the name of Yuko Fukui, et al.
Tanaka, et al., "Metabolic Engineering to Modify Flower Color"; Plant Cell Physiol. 39(11), 1119-1126, 1998.
Mol, et al., "Novel coloured flowers," Curr. Opinion Biotechnol., vol. 10(2), pp. 198 to 201, Apr. 1999.
Mol, et al., "How genes paint flowers and seeds"; Trends in Plant Science vol. 3, No. 6, pp. 212-217, Jun. 1998.
Biolley, et al., "Anthocyanins in Modern Roses: Chemical and Colorimetric Features in Relations to the Colour Range"; Journal of Experimental Botany, vol. 44, No. 268, pp. 1725-1734, Nov. 1993.
Mikanagi, et al.,"Anthocyanins in flowers of genus *Rosa*, sections *cinnamomeae* (=*Rosa*), *chinenses*, *gallicanae* and some modern garden roses"; Biochemical Systematics Ecology, 28 (2000) pp. 887-902.
Doukyu, et al.; "Indigo production by *Escherichia coli* carrying the phenol hydroxylase gene from *Acinetobacter* sp. strain ST-550 in a water-organic solvent two-phase system"; Appl. Microbiol. Biotechnol., 2003, 60:720-725.
August, et al., "Sequence Analysis and Functional Characterization of the Violacein Biosynthetic Pathway from *Chromobacterium violaceum*"; J. Mol. Biotechnol. 2000 2(4):513-519.
Brady, et al., "Cloning and Heterogeneous Expression of a Natural Product Biosynthetic Gene Cluster from eDNA"; Organic Letters; 2001, vol. 3, No. 13, pp. 1981-1984.
Fujikawa, et al., Structure of Genipocyanin $G_1$, A Spontaneous Reaction Product Between Genipin and Glycine; Tetrahedron Letters, vol. 28, No. 40, pp. 4699-4700.

(Continued)

*Primary Examiner* — David T Fox
*Assistant Examiner* — Steven Bernacki
(74) *Attorney, Agent, or Firm* — Christie, Parker & Hale, LLP

(57) ABSTRACT

A method for producing a rose characterized by artificially suppressing the rose endogenous metabolic pathway and expressing the pansy gene coding for flavonoid 3',5'-hydroxylase.

13 Claims, 10 Drawing Sheets

OTHER PUBLICATIONS

Fujikawa, et al., Brilliant Skyblue Pigment Formation from Gardenia Fruits, J. Ferment. Technol., vol. 65, No. 4, pp. 419-424.

Holton, et al., "Cloning and expression of cytochrome P450 genes controlling flower colour"; Letters to Nature vol. 366, pp. 276-279, Nov. 18, 1993.

Tanaka, et al., "Molecular and Biochemical Characterization of Three Antocyanin Synthetic Enzymes from *Gentiani triflora*"; Plant Cell Physiol. 37(5), pp. 711-716, 1996.

Firoozabady, et al., Regeneration of Transgenic Rose (*Rosa hybrida*) Plants from Embryogenic Tissue; Bio/Technology, vol. 12, pp. 609-613, Jun. 12, 1994.

Meyer, et al., "A new petunia flower colour generated by transformation of a mutant with a maize gene"; Letters toNature , vol. 330, pp. 677-678, Dec. 17, 1987.

Helariutta, et al., Cloning of cDNA coding for dihydroflavonol-4-reductase (DFR) and characterization of *dfr* expression in the corollas of *Gerbera hybrida* var. Regina (Compositae); Plant Molecular Biologu,. 22, 183-193, 1993.

Tanaka, et al., "Molecular Cloning and Characterization of *Rosa hybrida* Dihydroflavonol 4-reductase Gene"; Plant Cell Physiol. 36(6), 1023-1031, 1995.

Johnson, et al., *Cymbidium hybrida* dihydroflavonol 4-reductase does not efficiently reduce dihydrokaempferol to produce orange pelargonidin-type anthocyanins, The Plant Journal, 19(1), 81-85, 1999.

Forkmann, et al., "Distinct Substrate Specificity of Dihydroflavonol 4-Reductase from Flowers of *Petunia hybrida*", Z. Naturforsch. pp. 1146-1148.

Terada, et al., "Efficient gene targeting by homologous recombination in rice"; Nature Biotechnology, vol. 20, Oct. 2002, pp. 1030-1034.

Van Der Krol, et al., An anti-sense chalcone synthase gene in transgenic plants inhibits flower pigmentation:, Letter to Nature, vol. 333, Jun. 30, 1988, pp. 866-869.

Napoli, et al., Introduction of a Chimeric Chalcone Synthase Gene into Petunia Results in Reversible Co-Suppression of Homologous Genes in trans; The Plant Cell, vol. 2, pp. 279-289, Apr. 1990.

Waterhouse, et al., "Virus resistance and gene silencing in plants can be induced by simultaneous expression of sense and antisense RNA"; Pro. Natl. Acad. Sci. USA, vol. 95, pp. 13959-13964, Nov. 1998.

Gutterson, "Anthocyanin Biosynthetic Genes and Their Application to Flower Color Modification through Sense Suppression"; HortScience , vol. 30(5), pp. 964-966, Aug. 1995.

Forkmann, et al., "Metabolic engineering and applications of flavonoids," Curr. Opin. Biotechnol. Apr. 2001, vol. 12(2) pp. 155 to 160.

Forkmann, "Flavonoids as Flower Pigments: The Formation of the Natural Spectrum and its Extension by Genetic Engineering"; Plant Breeding 106, 1-26 (1991).

Lazo, et al., "A DNA Transformation-Competent *Arabidopsis* Genomic Library in *Agrobacterium*"; Bio/Technology, vol. 9, pp. 963-967, Oct. 1991.

Koes, et al., "Cloning and Molecular Characterization of the chalcone synthase multigene family of *Petunia hybrida*"; Gene 81 (1989), pp. 245-257, 1989 Elsevier Science Publishers B.V.

Martin, et al., "Contro of anthocyanin biosynthesis in flowers of *Antirrhinum majus*", The Plant Journal, (1991) 1(1), 37-49.

Mitsuhara, et al., "Efficient Promoter Cassettes for Enhanced Expression of Foreign Genes in Dicotyledonous and Monocotyledonous Plants", Plant Cell Physiol. 37(1), 49-59, 1996.

Bevan, "Binary *Agrobacterium* vectors for plant transformation," Nucleic Acids Research, vol. 12, No. 22, 1984, pp. 8711-8721, 1984.

Turpen, et al., "Rapid Isolation of RNA by a Guanidinium Thiocyanate/Cesium Chloride Gradient Method", BioTechniques, vol. 4, No. 1, pp. 11-15, 1986.

Van Engelen, et al., "pBINPLUS: an improved plant transformation vector based on pBIN19", Transgenic Research 4, 288-290, 1995.

Yanisch-Perron, et al., "Improved M13 phage cloning vectors and host strains: nucleotides sequences of the M13mp18 and pUC19 vectors", *Gene*, 33 (1985), pp. 103-119, Elsevier.

Bodeau, "Genetic and molecular regulation of *Bronze-2* and other maize anthocyanin genes", Dissertation, Stanford University, USA, 1994.

Yonekura-Sakakibara, et al., "Molecular and Biochemical Characterization of a Novel Hydroxycinnamoly-CoA: Anthocyanin 3-*O*-Glucoside-6"-*O*-Acyltransferase from *Perilla frutescens*", Plant Cell Physiol. 41(4), 495-502, 2000.

Suzuki, et al., "Flower color modifications of *Torenia hybrida* by cosuppression of anthocyanin biosynthesis genes"; Molecular Breeding 6: 239-246, 2000.

Fujiwara, et al., "cDNA cloning, gene expression and subcellular localization of anthocyanin 5-aromatic acyltransferase from *Gentiana triflora*", The Plant Journal, 16(4), 421-431, 1998.

International Search Report dated Sep. 28, 2004, corresponding to PCT/JP2004/011958.

\* cited by examiner

SEQUENCE LISTING

<160> NUMBER OF SEQ ID NOS: 21

<210> SEQ ID NO 1
<211> LENGTH: 1662
<212> TYPE: DNA
<213> ORGANISM: Artificial Sequence
<220> FEATURE:
<223> OTHER INFORMATION: Viola Wittrockiana hybrid

<400> SEQUENCE: 1

```
gaattcggca cgagagccaa tatggcaatt ccagtcactg accttgctgt cgcggttatc      60
cttttcttga tcactcgctt cctagttcgt tctcttttca agaaaccaac cggaccgctc     120
```

```
ccgccgggtc cttcaggctg gcccttggtg ggcgcgctcc ctctcctagg cgccatgcct    180
cacgtcacac tagccaacct cgctaaaaaa tacggtccga tcatgtacct aaaaatgggc    240
acgtgcgaca tggtggtcgc gtccactccc gactcggctc gagccttcct caaaacccta    300
gacctcaact tctccgaccg cccgcccaac gccggcgcca cccatttggc gtacggcgcg    360
caggacttgg tcttcgcgaa gtacggtcca aggtggaaga ccctaagaaa attgagcaac    420
ctccacatgc taggcgggaa ggcgctggac gattgggctc acgtgagggc taacgagcta    480
ggccacatgc ttaacgccat gtgcgaggcg agccggtgcg agagcccgt ggtgctggcc     540
gagatgctca cgtacgccat ggccaacatg atcggtcaag tgatactgag tcggcgcgtg    600
ttcgtcacca agggacagag tcgaacgag ttcaaagata tggtggtcga gttgatgact     660
tccgcggggt atttcaacat tggtgacttc ataccgtcga ttgcttggat ggatttgcaa    720
gggatcgagc gagggatgaa gaaattgcac acgaaattcg atgttttgtt gacgaagatg    780
atgaaggagc acagagcgac gagtcatgag cgcgaaggga atcggatttt cctcgacgtc    840
ctcttggaag aatgcgagaa tacaaatggc gagaagctta atgttaccaa cgtcaaagct    900
gtcctcttga acttattcac ggcgggtacg gacacatctt caagcataat cgaatgggcg    960
ttaaccgaaa tgatgaagaa tccgacgatc ttaaaaaaga cccaagaaga gatggatcga   1020
gtcatcggtc gcgatcggag attgctcgaa tccgacgttt cgaaactccc gtatttacaa   1080
gccatagcga agaaaacata tcgtaaacac ccatcgacac tctaaacct gccgaggatt    1140
gcgatccaag catgtgaagt tgatggctac tacatcccca agacacgag gcttagcgtc    1200
aacatttggg cgatcggtcg ggacccaagt gtttgggaga tccatcgga gttctcgcct    1260
gaaagattct tgtctgagga gaatgggaag atcagtccag gcgggaatga tttttgagctg   1320
attccgtttg gagcagggag gagaatttgt gctgggacaa ggatgggaat ggtccttgta   1380
agttatattt tgggcacttt ggtccattct tttgattgga aattaccaaa tggggtcagt   1440
gagattaaca tggatgagag ttttgggctt gcgttgcaaa aggccgtgcc tctctcggct   1500
acggtcagtc cacgattggc cccaagcgcg tacgttatat gagctgatgg gctgggcctg   1560
agcccaaaca tattgggtgt gttttatctg taatttttaa tattataaag ttcgtaattt   1620
tgtatttatg gttaattatg agttaaaaaa aaaaaaaaaa aa                     1662
```

<210> SEQ ID NO 2
<211> LENGTH: 506
<212> TYPE: PRT
<213> ORGANISM: Artificial Sequence
<220> FEATURE:
<223> OTHER INFORMATION: Viola Wittrockiana hybrid

<400> SEQUENCE: 2

```
Met Ala Ile Pro Val Thr Asp Leu Ala Val Ala Val Ile Leu Phe Leu
1               5                   10                  15

Ile Thr Arg Phe Leu Val Arg Ser Leu Phe Lys Lys Pro Thr Gly Pro
            20                  25                  30

Leu Pro Pro Gly Pro Ser Gly Trp Pro Leu Val Gly Ala Leu Pro Leu
        35                  40                  45

Leu Gly Ala Met Pro His Val Thr Leu Ala Asn Leu Ala Lys Lys Tyr
    50                  55                  60

Gly Pro Ile Met Tyr Leu Lys Met Gly Thr Cys Asp Met Val Val Ala
65                  70                  75                  80

Ser Thr Pro Asp Ser Ala Arg Ala Phe Leu Lys Thr Leu Asp Leu Asn
                85                  90                  95
```

-continued

```
Phe Ser Asp Arg Pro Pro Asn Ala Gly Ala Thr His Leu Ala Tyr Gly
            100                 105                 110

Ala Gln Asp Leu Val Phe Ala Lys Tyr Gly Pro Arg Trp Lys Thr Leu
            115                 120                 125

Arg Lys Leu Ser Asn Leu His Met Leu Gly Gly Lys Ala Leu Asp Asp
        130                 135                 140

Trp Ala His Val Arg Ala Asn Glu Leu Gly His Met Leu Asn Ala Met
145                 150                 155                 160

Cys Glu Ala Ser Arg Cys Gly Glu Pro Val Val Leu Ala Glu Met Leu
                165                 170                 175

Thr Tyr Ala Met Ala Asn Met Ile Gly Gln Val Ile Leu Ser Arg Arg
            180                 185                 190

Val Phe Val Thr Lys Gly Thr Glu Ser Asn Glu Phe Lys Asp Met Val
        195                 200                 205

Val Glu Leu Met Thr Ser Ala Gly Tyr Phe Asn Ile Gly Asp Phe Ile
210                 215                 220

Pro Ser Ile Ala Trp Met Asp Leu Gln Gly Ile Glu Arg Gly Met Lys
225                 230                 235                 240

Lys Leu His Thr Lys Phe Asp Val Leu Leu Thr Lys Met Met Lys Glu
                245                 250                 255

His Arg Ala Thr Ser His Glu Arg Glu Gly Lys Ser Asp Phe Leu Asp
            260                 265                 270

Val Leu Leu Glu Glu Cys Glu Asn Thr Asn Gly Glu Lys Leu Asn Val
        275                 280                 285

Thr Asn Val Lys Ala Val Leu Leu Asn Leu Phe Thr Ala Gly Thr Asp
290                 295                 300

Thr Ser Ser Ser Ile Ile Glu Trp Ala Leu Thr Glu Met Met Lys Asn
305                 310                 315                 320

Pro Thr Ile Leu Lys Lys Thr Gln Glu Glu Met Asp Arg Val Ile Gly
                325                 330                 335

Arg Asp Arg Arg Leu Leu Glu Ser Asp Val Ser Lys Leu Pro Tyr Leu
            340                 345                 350

Gln Ala Ile Ala Lys Glu Thr Tyr Arg Lys His Pro Ser Thr Pro Leu
        355                 360                 365

Asn Leu Pro Arg Ile Ala Ile Gln Ala Cys Glu Val Asp Gly Tyr Tyr
370                 375                 380

Ile Pro Lys Asp Thr Arg Leu Ser Val Asn Ile Trp Ala Ile Gly Arg
385                 390                 395                 400

Asp Pro Ser Val Trp Glu Asn Pro Ser Glu Phe Ser Pro Glu Arg Phe
                405                 410                 415

Leu Ser Glu Glu Asn Gly Lys Ile Ser Pro Gly Gly Asn Asp Phe Glu
            420                 425                 430

Leu Ile Pro Phe Gly Ala Gly Arg Arg Ile Cys Ala Gly Thr Arg Met
        435                 440                 445

Gly Met Val Leu Val Ser Tyr Ile Leu Gly Thr Leu Val His Ser Phe
450                 455                 460

Asp Trp Lys Leu Pro Asn Gly Val Ser Glu Ile Asn Met Asp Glu Ser
465                 470                 475                 480

Phe Gly Leu Ala Leu Gln Lys Ala Val Pro Leu Ser Ala Thr Val Ser
                485                 490                 495

Pro Arg Leu Ala Pro Ser Ala Tyr Val Ile
            500                 505
```

<210> SEQ ID NO 3
<211> LENGTH: 1795
<212> TYPE: DNA
<213> ORGANISM: Artificial Sequence
<220> FEATURE:
<223> OTHER INFORMATION: Viola Wittrockiana hybrid
<220> FEATURE:
<221> NAME/KEY: misc_feature
<222> LOCATION: (320)..(320)
<223> OTHER INFORMATION: n is a, c, g, or t

<400> SEQUENCE: 3

```
gaattcggca cgaggacaac atggcaattc tagtcaccga cttcgttgtc gcggctataa      60
ttttcttgat cactcggttc ttagttcgtt ctcttttcaa gaaaccaacc cgaccgctcc     120
ccccgggtcc tctcggttgg cccttggtgg gcgccctccc tctcctaggc gccatgcctc     180
acgtcgcact agccaaactc gctaagaagt atggtccgat catgcaccta aaaatgggca     240
cgtgcgacat ggtggtcgcg tccacccccg agtcggctcg agccttcctc aaaacgctag     300
acctcaactt ctccaaccgn ccacccaacg cgggcgcatc ccacctagcg tacggcgcgc     360
aggacttagt cttcgccaag tacggtccga ggtggaagac tttaagaaaa ttgagcaacc     420
tccacatgct aggcgggaag gcgttggatg attgggcaaa tgtgagggtc accgagctag     480
gccacatgct aaagccatg tgcgaggcga ccggtgcgg ggagcccgtg gtgctggccg      540
agatgctcac gtacgccatg gcgaacatga tcggtcaagt gatactcagc cggcgcgtgt     600
tcgtgaccaa agggaccgag tctaacgagt tcaaagacat ggtggtcgag ttgatgacgt     660
ccgccgggta cttcaacatc ggtgacttca taccctcgat cgcttggatg gatttgcaag     720
ggatcgagcg agggatgaag aagctgcaca cgaagtttga tgtgttattg acgaagatgg     780
tgaaggagca tagagcgacg agtcatgagc gcaaagggaa ggcagatttc ctcgacgttc     840
tcttggaaga atgcgacaat acaaatgggg agaagcttag tattaccaat atcaaagctg     900
tccttttgaa tctattcacg gcgggcacgg acacatcttc gagcataatc gaatgggcgt     960
taacggagat gatcaagaat ccgacgatct aaaaaaggc gcaagaggag atggatcgag    1020
tcatcggtcg tgatcggagg ctgctcgaat cggacatatc gagcctcccg tacctacaag    1080
ccattgctaa agaaacgtat cgcaaacacc cgtcgacgcc tctcaacttg ccgaggattg    1140
cgatccaagc atgtgaagtt gatggctact acatccctaa ggacgcgagg cttagcgtga    1200
acatttgggc gatcggtcgg gacccgaatg tttgggagaa tccgttggag ttcttgccgg    1260
aaagattctt gtctgaagag aatgggaaga tcaatcccgg tgggaatgat tttaagctga    1320
ttccgtttgg agccgggagg agaatttgtg cggggacaag gatgggaatg gtccttgtaa    1380
gttatatttt gggcactttg gtccattctt ttgattggaa attaccaaat ggtgtcgctg    1440
agcttaatat ggatgaaagt tttgggcttg cattgcaaaa ggccgtgccg ctctcggcct    1500
tggtcagccc acggttggcc tcaaacccgt acgcaacctg agctaatggg ctgggcctag    1560
ttttgtgggc cctaatttag agactttgt gttttaaggt gtgtacttta ttaattgggt    1620
gcttaaatgt gtgttttaat ttgtatttat ggttaattat gactttattg tataattatt    1680
tatttttccc ttctgggtat tttatccatt taattttct tcagaattat gatcatagtt    1740
atcagaataa aattgaaaat aatgaatcgg aaaaaaaaaa aaaaaaaaa aaaaa          1795
```

<210> SEQ ID NO 4
<211> LENGTH: 506
<212> TYPE: PRT
<213> ORGANISM: Artificial Sequence
<220> FEATURE:
<223> OTHER INFORMATION: Viola Wittrockiana hybrid

```
<400> SEQUENCE: 4

Met Ala Ile Leu Val Thr Asp Phe Val Ala Ala Ile Ile Phe Leu
1               5                   10                  15

Ile Thr Arg Phe Leu Val Arg Ser Leu Phe Lys Lys Pro Thr Arg Pro
            20                  25                  30

Leu Pro Pro Gly Pro Leu Gly Trp Pro Leu Val Gly Ala Leu Pro Leu
                35                  40                  45

Leu Gly Ala Met Pro His Val Ala Leu Ala Lys Leu Ala Lys Lys Tyr
        50                  55                  60

Gly Pro Ile Met His Leu Lys Met Gly Thr Cys Asp Met Val Val Ala
65                  70                  75                  80

Ser Thr Pro Glu Ser Ala Arg Ala Phe Leu Lys Thr Leu Asp Leu Asn
                85                  90                  95

Phe Ser Asn Arg Pro Pro Asn Ala Gly Ala Ser His Leu Ala Tyr Gly
            100                 105                 110

Ala Gln Asp Leu Val Phe Ala Lys Tyr Gly Pro Arg Trp Lys Thr Leu
        115                 120                 125

Arg Lys Leu Ser Asn Leu His Met Leu Gly Gly Lys Ala Leu Asp Asp
130                 135                 140

Trp Ala Asn Val Arg Val Thr Glu Leu Gly His Met Leu Lys Ala Met
145                 150                 155                 160

Cys Glu Ala Ser Arg Cys Gly Glu Pro Val Val Leu Ala Glu Met Leu
                165                 170                 175

Thr Tyr Ala Met Ala Asn Met Ile Gly Gln Val Ile Leu Ser Arg Arg
            180                 185                 190

Val Phe Val Thr Lys Gly Thr Glu Ser Asn Glu Phe Lys Asp Met Val
        195                 200                 205

Val Glu Leu Met Thr Ser Ala Gly Tyr Phe Asn Ile Gly Asp Phe Ile
210                 215                 220

Pro Ser Ile Ala Trp Met Asp Leu Gln Gly Ile Glu Arg Gly Met Lys
225                 230                 235                 240

Lys Leu His Thr Lys Phe Asp Val Leu Leu Thr Lys Met Val Lys Glu
                245                 250                 255

His Arg Ala Thr Ser His Glu Arg Lys Gly Lys Ala Asp Phe Leu Asp
            260                 265                 270

Val Leu Leu Glu Glu Cys Asp Asn Thr Asn Gly Glu Lys Leu Ser Ile
        275                 280                 285

Thr Asn Ile Lys Ala Val Leu Leu Asn Leu Phe Thr Ala Gly Thr Asp
290                 295                 300

Thr Ser Ser Ser Ile Ile Glu Trp Ala Leu Thr Glu Met Ile Lys Asn
305                 310                 315                 320

Pro Thr Ile Leu Lys Lys Ala Gln Glu Glu Met Asp Arg Val Ile Gly
                325                 330                 335

Arg Asp Arg Arg Leu Leu Glu Ser Asp Ile Ser Ser Leu Pro Tyr Leu
            340                 345                 350

Gln Ala Ile Ala Lys Glu Thr Tyr Arg Lys His Pro Ser Thr Pro Leu
        355                 360                 365

Asn Leu Pro Arg Ile Ala Ile Gln Ala Cys Glu Val Asp Gly Tyr Tyr
370                 375                 380

Ile Pro Lys Asp Ala Arg Leu Ser Val Asn Ile Trp Ala Ile Gly Arg
385                 390                 395                 400

Asp Pro Asn Val Trp Glu Asn Pro Leu Glu Phe Leu Pro Glu Arg Phe
                405                 410                 415
```

```
Leu Ser Glu Glu Asn Gly Lys Ile Asn Pro Gly Gly Asn Asp Phe Lys
                420                 425                 430
Leu Ile Pro Phe Gly Ala Gly Arg Arg Ile Cys Ala Gly Thr Arg Met
            435                 440                 445
Gly Met Val Leu Val Ser Tyr Ile Leu Gly Thr Leu Val His Ser Phe
        450                 455                 460
Asp Trp Lys Leu Pro Asn Gly Val Ala Glu Leu Asn Met Asp Glu Ser
465                 470                 475                 480
Phe Gly Leu Ala Leu Gln Lys Ala Val Pro Leu Ser Ala Leu Val Ser
                485                 490                 495
Pro Arg Leu Ala Ser Asn Pro Tyr Ala Thr
            500                 505

<210> SEQ ID NO 5
<211> LENGTH: 1474
<212> TYPE: DNA
<213> ORGANISM: Rosa hybrida

<400> SEQUENCE: 5
ggagatatca aaatggtgac cgtcgaggaa gtccgcaagg ctcaacgcgc tgagggtccg      60
gctaccgtcc tggccatcgg gacagcaact cctcccaact gtattgacca gagcacatac     120
cccgactact acttccgtat cactaagagc gagcacaagg ctgagctcaa ggagaaattc     180
cagcgcatgt gtgacaaatc tatgatcaag aagcgctaca tgtacttgac gaagaaatt      240 cttaaggaga atcctagtat gtgtgagtac atggccccct cacttgatgc aagacaagat     300
atggtggttg ttgaaattcc aaagcttgga aaagaggctg ccactaaggc tattaaggaa     360
tggggtcagc ccaagtccaa aatcacccac ttggtctttt gtaccactag tggcgtcgac     420
atgcccgggg ccgattacca gctcactaag ctcttaggcc tccgcccgtc cgtgaagcgt     480
ctcatgatgt accaacaagg gtgtttcgcc ggaggcacgg tgctccggtt ggctaaggac     540
ttggccgaga caacaagggg tgcacgtgtt cttgttgttt gctcagagat cactgccgtg     600
actttccgtg ggcctagcga caccatctc gatagtcttg tgggccaagc cttgttcggt      660
gatggtgctg cggccattat tgttggggcc gacccattgc cgaggttga aagccttcg       720 ttcgagttgg tctcggcagc ccaaactatc cttcctgaca gtgacggagc catcgacggg     780
catcttcgtg aagttgggct cacatttcac ctcctcaaag atgttccgg gctgatttca      840 aagaacatcg agaagagcct caacgaggcc ttcaaacctt tgaacatcac agactggaac     900 tcactttct ggattgcaca cccgggtggc cctgcaattt tagaccaagt agaggctaaa      960
ttgggcctga gcccgaaaaa gttagaagcc acaaggcata tattatccga gtacggcaat    1020
atgtctagtg cttgtgtgtt gtttatttg gacgaggtgc ggagaaagtc tgcagctaat     1080
gggcacaaga ccactggaga aggcctggag tggggtgtcc tatttggttt tgggccaggg    1140
ctcaccgtcg agaccgtcgt gcttcacagt gtggctgctt aaacttgaag gcatctgggt    1200
tcacttgagt gatctgctcc tggatttgtt cttatatatg tatcgtttcc actctacttt    1260
ccttgttaga tttcctttt tggattatt tttctggtga atttagcaat atatgtaatg      1320
atgaataata ttattccaca aatttcatac gagcaaaagt tcctgcaata atttagttag    1380
aagttgactt tccggaagat ttagagcggg gaatatatct cccactagct gaaagattat    1440
ccggggatag agtacgttca aaaaaaaaaa aaaa                                1474
```

```
<210> SEQ ID NO 6
<211> LENGTH: 420
<212> TYPE: DNA
<213> ORGANISM: Rosa hybrida

<400> SEQUENCE: 6
gaagaaggga ggctggagaa ggaggtcggt ggactcgaag aactcgtcct gcaaatgaaa      60
atcaactact acccaaaatg ccctcagccg aacttgccc tcggcgtgga agcccacacc     120
gacataagtg cactcacctt catcctccac aacatggttc ccggcctgca gctcttctac     180
ggcggcaaat gggtgacagc gaaatgcgtg cccaactcca tcgtcatgca catcggcgac     240
aacttggaga ttctgagcaa cggcaagtac aagagcattt ttcacagggg ggattgtcaa     300
caagggagaa ggtgaggttc tcgttggcgg ttttcttgta gccacccagg aggaggtcat     360
tctcaagccg ttgcgacgac tgtctcgagg aggaaccgcg tcttccaccc gacttttcgg     420

<210> SEQ ID NO 7
<211> LENGTH: 1808
<212> TYPE: DNA
<213> ORGANISM: Torenia hybrida

<400> SEQUENCE: 7
cttcaaagcc aaaagaaac aattaatcaa tggctgttga agcccccaaa acaatatgtg      60
cagtcctcga aactctctt attacaccac aaagtaccga tacagaacaa actctttcac     120
tcacattctt tgacatcaaa tgggttcatt tcatccaat gcaatgcctt gtgttgtaca     180
acttcccatg ttctaagtca cattttctcg aagccacagt tccgagcttc aaatcatcac     240
tctccaaaac tctcagacac tatcttccat tatcaggaaa cttatactat ccaaacccga     300
cccatgacat ggatgatgat gaatcgaaca tgcccgagat ccgttataaa cctggcgact     360
cggtttctct aaccgttgca gagtacttct ccggtcatga agacaatacg actactgaag     420
aatacttcaa ttcctcact ggaaatttcc agagagattg cgatcaattc tatgatctct     480
tacccgattt tcgagacccg gaaaccgaat ccaattgcac agtaatccca cttatagcag     540
ttcaaatcac actctttcca ggtgctggga tatgtctggg ggtcatcaac agtcacgtag     600
ttggcgatgc gagttccata gtgggattca tcaaagcttg gagtaaagtt gcaatgtatg     660
aagacgatga agagattcta gctaacaaca atttgattcc atcttatgac agatcagtcg     720
tgaaagatcc aaaagggatc aaatctttgc tctggaacaa gatgaagaac gtgaaatatc     780
aaccccaacc cgcaaaacat ctcccaacaa acaaggtccg agccacatac accttgagaa     840
agaacgatat cgagaggctg aaaacccgaa tccgatccaa gaaaccaggc acaacctgct     900
tatcatcttt cacaatcgca acagcctatg cttggacatg ccttgcaaaa tctgcagcag     960
aagctgaaga acaagtagtc caagacagtg acgacgagca cttgctcatg cccgttgatt    1020
tgagaccaag aatagatcct ccattaccac cttcttactt tggaaactgc gttcttccat    1080
cttttgcgaa aacgacgcat gggcttttga aggagagtt agggcttttt aatgcagtgg    1140
aagtgattag tgatgtcatt accggtatcg ttagcaagaa atatgacttg ttcaaagact    1200
tagacagaca aggtgagatt tttcgtgcct tgttcggaaa acgagtgttg gcgatcatgg    1260
gttcgcctaa gttcgatctc tacgaagttg atttcggggtg gggtaagccg aagaagattg    1320
aacctgtgtc cattgataga gagaggacga ctatgtggat tagcaagtct ggcgagtttg    1380
agggtggatt ggagattggt ttttcttttca ataagaagaa aatggatgct tttggcgagt    1440
gttttaacag cggtttgaag gatatttaat ttaaaaaatt gtttagcttt gatgcatgcg    1500
ttttatatat gttgtgaaat aatgtggtgt gcaataacta gagtaacttt aggttaataa    1560
```

-continued

```
attcggtttt tctgttaaat ctggatgatt cgtgcaagca aactgtcgat gcgttggatg    1620
gatgtcgggt ggtgtggaga ttgttgaaga aggaaatgga tgcttttttt atggtggttt    1680
gaaggatttg aatgtgtaga ttattggttt attgaggttg tttatatttg tgtatgttgt    1740
ttatgcatga aaatattta gatcccaaca ttttatgtat gacgtggttt aatatttcga    1800
tttcgatc                                                             1808
```

<210> SEQ ID NO 8
<211> LENGTH: 479
<212> TYPE: PRT
<213> ORGANISM: Torenia hybrida

<400> SEQUENCE: 8

```
Met Ala Val Glu Ala Pro Lys Thr Ile Cys Ala Val Leu Glu Asn Ser
1               5                   10                  15

Leu Ile Thr Pro Gln Ser Thr Asp Thr Glu Gln Thr Leu Ser Leu Thr
            20                  25                  30

Phe Phe Asp Ile Lys Trp Val His Phe His Pro Met Gln Cys Leu Val
        35                  40                  45

Leu Tyr Asn Phe Pro Cys Ser Lys Ser His Phe Leu Glu Ala Thr Val
    50                  55                  60

Pro Ser Phe Lys Ser Ser Leu Ser Lys Thr Leu Arg His Tyr Leu Pro
65                  70                  75                  80

Leu Ser Gly Asn Leu Tyr Tyr Pro Asn Pro Thr His Asp Met Asp Asp
                85                  90                  95

Asp Glu Ser Asn Met Pro Glu Ile Arg Tyr Lys Pro Gly Asp Ser Val
            100                 105                 110

Ser Leu Thr Val Ala Glu Tyr Phe Ser Gly His Glu Asp Asn Thr Thr
        115                 120                 125

Thr Glu Glu Tyr Phe Asn Tyr Leu Thr Gly Asn Phe Gln Arg Asp Cys
    130                 135                 140

Asp Gln Phe Tyr Asp Leu Leu Pro Asp Phe Arg Asp Pro Glu Thr Glu
145                 150                 155                 160

Ser Asn Cys Thr Val Ile Pro Leu Ile Ala Val Gln Ile Thr Leu Phe
                165                 170                 175

Pro Gly Ala Gly Ile Cys Leu Gly Val Ile Asn Ser His Val Val Gly
            180                 185                 190

Asp Ala Ser Ser Ile Val Gly Phe Ile Lys Ala Trp Ser Lys Val Ala
        195                 200                 205

Met Tyr Glu Asp Asp Glu Glu Ile Leu Ala Asn Asn Leu Ile Pro
    210                 215                 220

Ser Tyr Asp Arg Ser Val Val Lys Asp Pro Lys Gly Ile Lys Ser Leu
225                 230                 235                 240

Leu Trp Asn Lys Met Lys Asn Val Lys Tyr Gln Pro Gln Pro Ala Lys
                245                 250                 255

His Leu Pro Thr Asn Lys Val Arg Ala Thr Tyr Thr Leu Arg Lys Asn
            260                 265                 270

Asp Ile Glu Arg Leu Lys Thr Arg Ile Arg Ser Lys Lys Pro Gly Thr
        275                 280                 285

Thr Cys Leu Ser Ser Phe Thr Ile Ala Thr Ala Tyr Ala Trp Thr Cys
    290                 295                 300

Leu Ala Lys Ser Ala Ala Glu Ala Glu Glu Gln Val Val Gln Asp Ser
305                 310                 315                 320

Asp Asp Glu His Leu Leu Met Pro Val Asp Leu Arg Pro Arg Ile Asp
                325                 330                 335
```

```
Pro Pro Leu Pro Pro Ser Tyr Phe Gly Asn Cys Val Leu Pro Ser Phe
        340                 345                 350

Ala Lys Thr Thr His Gly Leu Leu Lys Gly Glu Leu Gly Leu Phe Asn
            355                 360                 365

Ala Val Glu Val Ile Ser Asp Val Ile Thr Gly Ile Val Ser Lys Lys
        370                 375                 380

Tyr Asp Leu Phe Lys Asp Leu Asp Arg Gln Gly Glu Ile Phe Arg Ala
385                 390                 395                 400

Leu Phe Gly Lys Arg Val Leu Ala Ile Met Gly Ser Pro Lys Phe Asp
                405                 410                 415

Leu Tyr Glu Val Asp Phe Gly Trp Gly Lys Pro Lys Lys Ile Glu Pro
            420                 425                 430

Val Ser Ile Asp Arg Glu Arg Thr Thr Met Trp Ile Ser Lys Ser Gly
        435                 440                 445

Glu Phe Glu Gly Gly Leu Glu Ile Gly Phe Ser Phe Asn Lys Lys Lys
        450                 455                 460

Met Asp Ala Phe Gly Glu Cys Phe Asn Ser Gly Leu Lys Asp Ile
465                 470                 475

<210> SEQ ID NO 9
<211> LENGTH: 1252
<212> TYPE: DNA
<213> ORGANISM: Iris hollandica

<400> SEQUENCE: 9
aaacaatata tcgagatgat gagccccgtt gtcgtgaccg agcgagcgg ctacgtcggt      60 tcatggcttg ttatgaagct ccttcgcgac ggctacgccg ttcgagccac tgtcagagac    120
ccaaccaatg tggagaagac gaagccgctg ttggacctcc ccggagctga cgcgctgctc    180
accatctgga aggcagacct cggccaggac ggaagcttcg acaaggcggt cgcaggatgc    240
accgcggtct ccacgtcgc cacgcccatg gatttcgagt ccaaggaccc agaaaacgag     300
gtgatcaagc cgaccataaa tggcgttta agtatcatga ggtcctgtaa aaggccgga     360 acggtcaaac gcgtcgtctt cacttcatcc gccgggacgg tggacgtgaa agaacatcag    420
cagacggagt acgacgagag ctcgtggagc gacgtcgact tctgcagacg tgtcaagatg    480
acaggctgga tgtatttgt gtcgaagact ctggccgaga gagcagcctg gaatttgca     540 agagagaatg gcatagactt cataagcatc atccccacgc tagtcgtcgg tccttcatc    600 accacaacta tgccacccag catggtgact gcgctatcat tcatgacagg aaacgaagca    660
cactatcaca taatcaagca cgcgcagctc gtccaccttg acgacctgtg cgctgcccac    720
atttacctcc tgaatcgccc cgaagcgaac gggaggtaca tatgctcatc gcacgaagcc    780
accatccacg acctggcgag gatggtcagg gagaggcacc cttggtgcgg ctccataccc    840
gaaaagttcg acggcatcga gaaggacgtc agaaccgtgc acttctcttc caagaggctt    900
ttggacctcg ggttcgagtt caagtacacg gtggaagaaa tgttcgacga agcgatacgg    960
tcgtgcgtcg agaagaagct catacccctc cctgagaatg caacgtgga cgcagctgcc   1020 ggggctaaag acatggttca tggagcagag gaacatgccc gaattgctat ggaactagaa   1080
ccaaaaaaaa aggtcaagtg aaatgtgaag ataacacatt ttatgcgtat ggacattaca   1140
atcttagatg ttcaaggttt caaattgtat cttaagtgta tgatttatgt tgacactcgg   1200
aagtttcatt gaaattaata aaaagggatt tgctcaaaaa aaaaaaaaaa aa           1252
```

<210> SEQ ID NO 10
<211> LENGTH: 361
<212> TYPE: PRT
<213> ORGANISM: Iris hybrida

<400> SEQUENCE: 10

Met Met Ser Pro Val Val Thr Gly Ala Ser Gly Tyr Val Gly Ser
1               5                   10                  15

Trp Leu Val Met Lys Leu Leu Arg Asp Gly Tyr Ala Val Arg Ala Thr
            20                  25                  30

Val Arg Asp Pro Thr Asn Val Glu Lys Thr Lys Pro Leu Leu Asp Leu
        35                  40                  45

Pro Gly Ala Asp Ala Leu Leu Thr Ile Trp Lys Ala Asp Leu Gly Gln
    50                  55                  60

Asp Gly Ser Phe Asp Lys Ala Val Ala Gly Cys Thr Ala Val Phe His
65                  70                  75                  80

Val Ala Thr Pro Met Asp Phe Glu Ser Lys Asp Pro Glu Asn Glu Val
                85                  90                  95

Ile Lys Pro Thr Ile Asn Gly Val Leu Ser Ile Met Arg Ser Cys Lys
            100                 105                 110

Lys Ala Gly Thr Val Lys Arg Val Val Phe Thr Ser Ser Ala Gly Thr
        115                 120                 125

Val Asp Val Lys Glu His Gln Gln Thr Glu Tyr Asp Glu Ser Ser Trp
    130                 135                 140

Ser Asp Val Asp Phe Cys Arg Arg Val Lys Met Thr Gly Trp Met Tyr
145                 150                 155                 160

Phe Val Ser Lys Thr Leu Ala Glu Arg Ala Ala Trp Glu Phe Ala Arg
                165                 170                 175

Glu Asn Gly Ile Asp Phe Ile Ser Ile Pro Thr Leu Val Val Gly
            180                 185                 190

Pro Phe Ile Thr Thr Thr Met Pro Pro Ser Met Val Thr Ala Leu Ser
        195                 200                 205

Phe Met Thr Gly Asn Glu Ala His Tyr His Ile Ile Lys His Ala Gln
210                 215                 220

Leu Val His Leu Asp Asp Leu Cys Ala Ala His Ile Tyr Leu Leu Asn
225                 230                 235                 240

Arg Pro Glu Ala Asn Gly Arg Tyr Ile Cys Ser Ser His Glu Ala Thr
                245                 250                 255

Ile His Asp Leu Ala Arg Met Val Arg Glu Arg His Pro Trp Cys Gly
            260                 265                 270

Ser Ile Pro Glu Lys Phe Asp Gly Ile Glu Lys Asp Val Arg Thr Val
        275                 280                 285

His Phe Ser Ser Lys Arg Leu Leu Asp Leu Gly Phe Glu Phe Lys Tyr
    290                 295                 300

Thr Val Glu Glu Met Phe Asp Glu Ala Ile Arg Ser Cys Val Glu Lys
305                 310                 315                 320

Lys Leu Ile Pro Leu Pro Glu Asn Gly Asn Val Asp Ala Ala Ala Gly
                325                 330                 335

Ala Lys Asp Met Val His Gly Ala Glu His Ala Arg Ile Ala Met
            340                 345                 350

Glu Leu Glu Pro Lys Lys Lys Val Lys
        355                 360

<210> SEQ ID NO 11
<211> LENGTH: 1297
<212> TYPE: DNA
<213> ORGANISM: Nierembergia hybrida

<400> SEQUENCE: 11

| | | | | |
|---|---|---|---|---|
| attcatacta catttcccg tccttaagta aattttattt ctgaaaatgg caagcgaagc | 60 |
| agttcatgct agtccgacag tttgtgtcac cggagcagct ggattcattg gctcttggct | 120 |
| tgtcatgaga ctccttgaac gcggttataa tgttcatgct actgttcgtg atcctgagaa | 180 |
| caagaagaag gtgaaacatc tacaggaatt gccaaaagct gatacgaact taacgctgtg | 240 |
| gaaagcggac ttggcggtag aaggaagctt tgatgaagcc attaaggct gtcaaggagt | 300 |
| atttcatgtg ccactccta tggatttcga gtccaaggac cctgagatg aagtaatcaa | 360 |
| gccaacagtc cagggaatgt tgagcatcat agaatcatgt gttaaagcaa acacagtgaa | 420 |
| gaggttggtt ttcacttcgt ctgctggaac tctagatgtc caagagcaac aaaaactctt | 480 |
| ctacgatgag accagctgga gcgacttgga cttcataaat gccaagaaga tgacaggatg | 540 |
| gatgtacttt gtttcaaaga tactcgcgga gaaggctgca atggaagaag ctaaaaagaa | 600 |
| caacattgat tcattagca tcataccacc actggttgtt ggtccattca tcaccccttc | 660 |
| gttcccgcct agtttaatca ctgccctttc actaattact gggaatgaag ctcactactg | 720 |
| catcattaaa caaggtcaat atgtgcattt ggatgatctt tgtgaggctt acatattctt | 780 |
| gtatgaacac cctaaagcag agggaaggtt catttgctcg tcccatcatg ctatcatcta | 840 |
| tgatgtagct aagatgatcc gagaaaaatg gccagagtac tacgttccta cagagtttaa | 900 |
| aggcatcgct aaggacctac ctgtggtggc ttttttcgtca agaagttga cagatatggg | 960 |
| ttttcagttc aagtacactt tggaggatat gtataaaggg ccattgaga cttgtcgaca | 1020 |
| gaagcagttg cttcccttt ctaccaatag gccttcggaa aatggacttg acaaagaagc | 1080 |
| catttccatt tcttctgaaa actttgcaag tggaaaagag aatgcaccag ttgcaaatca | 1140 |
| caaagtaaag ttaacaagtg ttgaaattta gaactgcaat ctttcaaatg taaaagaggc | 1200 |
| aagcttgcct atcaacatct ttgcttctaa gttgtcatct atttgtttct ttaatgctaa | 1260 |
| agcagtaaaa ggttcaatga aaaaaaaaaa aaaaaaa | 1297 |

<210> SEQ ID NO 12
<211> LENGTH: 374
<212> TYPE: PRT
<213> ORGANISM: Nierembergia hybrida

<400> SEQUENCE: 12

Met Ala Ser Glu Ala Val His Ala Ser Pro Thr Val Cys Val Thr Gly
1               5                   10                  15

Ala Ala Gly Phe Ile Gly Ser Trp Leu Val Met Arg Leu Leu Glu Arg
            20                  25                  30

Gly Tyr Asn Val His Ala Thr Val Arg Asp Pro Glu Asn Lys Lys Lys
        35                  40                  45

Val Lys His Leu Gln Glu Leu Pro Lys Ala Asp Thr Asn Leu Thr Leu
    50                  55                  60

Trp Lys Ala Asp Leu Ala Val Glu Gly Ser Phe Asp Glu Ala Ile Lys
65                  70                  75                  80

Gly Cys Gln Gly Val Phe His Val Ala Thr Pro Met Asp Phe Glu Ser
                85                  90                  95

Lys Asp Pro Glu Asn Glu Val Ile Lys Pro Thr Val Gln Gly Met Leu
            100                 105                 110

-continued

```
Ser Ile Ile Glu Ser Cys Val Lys Ala Asn Thr Val Lys Arg Leu Val
    115                 120                 125
Phe Thr Ser Ser Ala Gly Thr Leu Asp Val Gln Glu Gln Gln Lys Leu
130                 135                 140
Phe Tyr Asp Glu Thr Ser Trp Ser Asp Leu Asp Phe Ile Asn Ala Lys
145                 150                 155                 160
Lys Met Thr Gly Trp Met Tyr Phe Val Ser Lys Ile Leu Ala Glu Lys
                165                 170                 175
Ala Ala Met Glu Glu Ala Lys Lys Asn Asn Ile Asp Phe Ile Ser Ile
            180                 185                 190
Ile Pro Pro Leu Val Val Gly Pro Phe Ile Thr Pro Ser Phe Pro Pro
        195                 200                 205
Ser Leu Ile Thr Ala Leu Ser Leu Ile Thr Gly Asn Glu Ala His Tyr
    210                 215                 220
Cys Ile Ile Lys Gln Gly Gln Tyr Val His Leu Asp Asp Leu Cys Glu
225                 230                 235                 240
Ala Tyr Ile Phe Leu Tyr Glu His Pro Lys Ala Glu Gly Arg Phe Ile
                245                 250                 255
Cys Ser Ser His His Ala Ile Ile Tyr Asp Val Ala Lys Met Ile Arg
            260                 265                 270
Glu Lys Trp Pro Glu Tyr Tyr Val Pro Thr Glu Phe Lys Gly Ile Ala
        275                 280                 285
Lys Asp Leu Pro Val Val Ala Phe Ser Ser Lys Leu Thr Asp Met
    290                 295                 300
Gly Phe Gln Phe Lys Tyr Thr Leu Glu Asp Met Tyr Lys Gly Ala Ile
305                 310                 315                 320
Glu Thr Cys Arg Gln Lys Gln Leu Leu Pro Phe Ser Thr Asn Arg Pro
                325                 330                 335
Ser Glu Asn Gly Leu Asp Lys Glu Ala Ile Ser Ile Ser Ser Glu Asn
            340                 345                 350
Phe Ala Ser Gly Lys Glu Asn Ala Pro Val Ala Asn His Lys Val Lys
        355                 360                 365
Leu Thr Ser Val Glu Ile
    370

<210> SEQ ID NO 13
<211> LENGTH: 20
<212> TYPE: DNA
<213> ORGANISM: Artificial
<220> FEATURE:
<223> OTHER INFORMATION: DFR-2F primer

<400> SEQUENCE: 13
caagcaatgg catcggaatc                                                 20

<210> SEQ ID NO 14
<211> LENGTH: 22
<212> TYPE: DNA
<213> ORGANISM: Artificial
<220> FEATURE:
<223> OTHER INFORMATION: DRF-2B primer

<400> SEQUENCE: 14
tttccagtga gtggcgaaag tc                                              22

<210> SEQ ID NO 15
<211> LENGTH: 20
<212> TYPE: DNA
<213> ORGANISM: Artificial Sequence
```

```
<220> FEATURE:
<223> OTHER INFORMATION: ANS-2F primer

<400> SEQUENCE: 15
tggactcgaa gaactcgtcc                                              20

<210> SEQ ID NO 16
<211> LENGTH: 19
<212> TYPE: DNA
<213> ORGANISM: Artificial Sequence
<220> FEATURE:
<223> OTHER INFORMATION: ANS-2B primer

<400> SEQUENCE: 16
cctcaccttc tcccttgtt                                               19

<210> SEQ ID NO 17
<211> LENGTH: 17
<212> TYPE: DNA
<213> ORGANISM: Artificial Sequence
<220> FEATURE:
<223> OTHER INFORMATION: ATC primer
<220> FEATURE:
<221> NAME/KEY: misc_feature
<222> LOCATION: (9)..(9)
<223> OTHER INFORMATION: n is i
<220> FEATURE:
<221> NAME/KEY: misc_feature
<222> LOCATION: (15)..(15)
<223> OTHER INFORMATION: n is i

<400> SEQUENCE: 17
gayttyggnt ggggnaa                                                 17

<210> SEQ ID NO 18
<211> LENGTH: 23
<212> TYPE: DNA
<213> ORGANISM: Artificial Sequence
<220> FEATURE:
<223> OTHER INFORMATION: oligo dT primer

<400> SEQUENCE: 18
tttttttttt tttttttctc gag                                          23

<210> SEQ ID NO 19
<211> LENGTH: 26
<212> TYPE: DNA
<213> ORGANISM: Artificial Sequence
<220> FEATURE:
<223> OTHER INFORMATION: RDF310 primer

<400> SEQUENCE: 19
ccctcgagcc cttgatggcc tcgtcg                                       26

<210> SEQ ID NO 20
<211> LENGTH: 26
<212> TYPE: DNA
<213> ORGANISM: Artificial Sequence
<220> FEATURE:
<223> OTHER INFORMATION: RDF830

<400> SEQUENCE: 20
gggtcgacgc ggccctctgc tttcgg                                       26

<210> SEQ ID NO 21
<211> LENGTH: 2934
<212> TYPE: DNA
<213> ORGANISM: Rose hybrida
```

-continued

```
<400> SEQUENCE: 21
aagcttcagc aagagttgaa gaaataggga cagagccatc catgtgcttt gatgaatctg        60
atgggataca aaatgtgaaa gattcacttg ctgatttatc cagaatttct tcatatagtg       120
aggagaatgt tgaaagatct aatgatgagc actctgttaa actagacgga attcatgtgc       180
agcacgagtg tcatgagggc agtgaagaag acaaacctga tggtaagagc ggtgagaatg       240
cagttgatct ggctaatcat ggcatggctc gaactgattt ttgtcagata acagaagaga       300
ttgagaatgg agtagtcatc actgagatga gcaacattgc caaccctgat aaaactgata       360
ttccaaacgg ggtgcctcaa aatgagactg atgatggatt taataacact caggatgatg       420
ctaatacaaa ggaagtgaca gaagagaatt ctgacagacg tgcgaaggaa gtgacagaag       480
agaattctga caaagatgtt ttgaagaata tccttgaatt ctcacgtgct tcttctgtgg       540 tggatttttga aattccagtg ttggatgtga aatttacttc tcttgaaagt tgcagtgcca       600
cttgttctct tgcagccctt ttgtctgaat cgccggaatc aatgactgaa gcaccttgtg       660
tgaggcaaat tgatgatgtg cccccggttg gtgaggagtc tagcttgatt ttggtggaag       720
atcgggagcc ggttggtcct actcctgatg gtaattttc tgtggatatg gattactata       780
gtgtagcaga acctttgagc acatgggatg cgaatctgca gtgtgaaaca tcaaatagcc       840
atgagacttt tgctgcaagt ctcatttgat agcttctgtg ttaataactt tgttagtctg       900
tacataaatt tgtctagaca agaattggtc gtgtactatc gtgtgttttt gccgtgcttt       960
agtactcatg aaccaattca gagaaaactg gctgcatatt ttgaggagtc tctgaattct      1020
tcaatgctca actggtatgc atgtaggtgg catatcactt cagggattct tctattcttt      1080
aactttacgc atcttgacat tttgtatata acaaaatcag gtctattggg tgaaagtaat      1140
tggctagaat ggaaagctct acggttttac cgcaggtcaa tttttcatagc tccacaagtg      1200 aattgaaaat gctcataggc tttatgtttg tcctccacct ctggcgacga tgtttgttgg      1260
ggagttaact caaacctacc accaaactcg aacccatctt ccataattta taatacaaat      1320
ttgcgatcat ttgttcatcc aattattgtg acactcggct accacccaaa atatcggtca      1380
cagacccaaa cgtattgtca caacaaatcg tgtctctcgc attaaacaca gctagaaaga      1440
agagttgaac ccacaattcg agcacccact acctatgtac gaagtcatga gttcgagtca      1500 ccatagggg agaagtgaaa tcatttgatc atctttaaag aaataaaagg aagagttgaa      1560
cccacaattg gctcttgtcc caaaagaaac taatagttca gtgcaccgac gtgtatttgc      1620
accgacataa atgatgatgtt agattatatt aaatacactc ttaggttatt aataaaaata      1680
ttaattataa atatcaaaag ttgagatcat cttataaatg ttgggtcagt tacaccgtcg      1740
gtgcatagaa taattttccaa actatataat agccttcatt ttctgattta gctcatggga      1800
catgattgct ataaataatt gtactcgtag aggcatactt gtgtcttttt atacagttgt      1860
actgaagctc agaaaagttt atgaaggtga gaactgagaa gggcaaggca tttggtagtt      1920
gaggtatatg agagcatgaa ccccatgcat tgcagctacc acctctcttt tttccttctt      1980
cccatacaaa taaaccaac tcttctcacc taagtctatc atctttattt atggcagctc      2040
ttgcttaatt agctcatcta tattatatta tttatctata atatgtgtca ctctgtctac      2100
ctaccagccc aaaataaaac tgataatagt caatttgatg atattttttg tttttgttt      2160 tgttttgtct ttttttgtatt gatttttta aaattaaaat gacttcattt tttgtttttg      2220 ttttttttc tatttttttt tatagaaaaa ttggcaaact ttcattatct gttattgatg      2280
acaattaagc cattaaaacc tataattaat tatctttcaa ttcgagtaaa tttaaaacgg      2340
```

```
tgtaaaatta aaatatgatc gtattcttaa atgaataaaa ctcacttaat aatagtaata    2400
cttgaatcac atctacgaac atagattctt ttcatccagt ctaaccatgt ttgaatatat    2460
agagtttgat tatggttatg tctttgtcca cattttggtt tgtaaataaa tgtgcaacgg    2520
aggtatggta ctgttgctct atcaaattca agtttgaatt aaaagaaaaa aaaaaagacg    2580
atattttgtg cgctttgttt ggtaggtaaa acgagagaac aaacgcattc caaatcatgc    2640
ggattttgat cggcaacaca caccacaaaa aaccgtacac gatgcacgtg ccatttgccg    2700
ggggtttcta acaaggtaat tgggcaggca cgtgatcccc cagctaccca cctctcgctt    2760
cccttctcaa actcctttc catgtatata tacaacccct tttctcagac cattatattc    2820
taacattttt gctttgctat tgtaacgcaa caaaaactgc tcattccatc cttgttcctc    2880
cccattttga tcttctctcg accttctcc gagatgggta ccgagctcga attc          2934
```

METHOD FOR PRODUCING ROSE WITH ALTERED PETAL COLORS

CROSS-REFERENCE TO RELATED APPLICATION

This application is a National Phase Patent Application of International Application Number PCT/JP2004/011958, filed on Aug. 13, 2004, which claims priority of Japanese Patent Application Number 2003-293121, filed on Aug. 13, 2003, and Japanese Patent Application Number 2004-192034, filed on Jun. 29, 2004.

INCORPORATION BY REFERENCE

The material in the text file entitled "10567931SEQLIS-TING.txt," amended Feb. 3, 2011, and being 38,000 bytes in size, is herein incorporated by reference in its entirety.

TECHNICAL FIELD

The present invention relates to a new method for producing a rose with altered petal colors. More specifically, it relates to a method for producing a rose by artificially inhibiting the endogenous metabolic pathway of rose, and expressing the gene coding for pansy flavonoid 3',5'-hydroxylase and the gene coding for dihydroflavonol reductase which reduces dihydromyricetin.

BACKGROUND ART

Flower petals perform the role of attracting pollinators such as insects and birds, which transport plant pollen, and therefore flower colors, shapes, patterns and odors have evolved in tandem with pollinators (Honda, T. et al., Gendai Kagaku, May, 25-32 (1998)). Probably as a result of this, it is rare for a single species of flower to exhibit several different colors, and for example, rose or carnation varieties exhibiting violet to blue colors do not exist, while iris or gentian varieties exhibiting bright red colors do not exist. Because flower color is the most important aspect of petals for purposes of appreciation as well, flowers of different colors have traditionally been bred by crossbreeding. The rose, known as the "queen of flowers" and having high commercial value, has also been crossbred throughout the world.

For example, the current yellow rose cultivar was created by crossbreeding of *Rosa foetida*, originating from western Asia, with a non-yellow rose variety. However, because flower color is determined by the genetic capacity of the plant, there has been a limit to the flower colors that can currently be produced in cross-bred strains whose available genetic sources are restricted (Tanaka et al. Plant Cell Physiol. 39, 1119-1126, 1998; Mol et al. Curr. Opinion Biotechnol. 10, 198-201 1999). Among these, the cultivation of blue roses has been thought impossible and has been considered the "holy grail" of colors (Oba, H., "Bara no Tanjo", 1997, Chukoshin-sho; Suzuki, M., "Shokubutsu Bio no Mahou: Aoi Bara mo Yume dewanakuhatta", 1990, Kodansha Bluebacks; Saisho, H., "Aoi Bara", 2001, Shogakkan).

Although "blue rose" varieties currently exist, these are actually pale violet roses. The first improved variety of "blue rose" by crossbreeding is said to have been the light-violet shaded grey-colored "Grey Pearl" created in 1945. The light-violet pink-colored "Staring Silver" was later created in 1957, and these varieties were crossed to produce several pale violet roses such as "Blue Moon" (1964) and "Madam Violet" (1981). These pale violet roses and other roses were then utilized in further breeding to create light-grey-colored roses such as "Seiryu" (1992) and "Blue Heaven" (2002), which were hailed as new types of "blue roses".

However, these flower colors are not actually blue but merely greyish-dull pink, and despite many years of breeding efforts, there is still no example of a truly "blue" rose. In horticultural industry, the group of colors from violet to blue is generally considered "blue" according to the RHSCC (The Royal Horticultural Society Colour Chart). It is an aim of the present invention to create rose plants having flower colors falling within the "violet group", "violet-blue" group and "blue group" according to the Royal Horticultural Society Colour Chart.

Flower colors derive mainly from the three compound groups of anthocyanins, carotenoids and betalains, but it is the anthocyanins, having the widest absorption wavelength range (from orange to blue), that are responsible for blue color. Anthocyanins belong to the flavonoid family and are biosynthesized by the metabolic pathway shown in FIG. 1. Anthocyanins are normally localized in the vacuoles of epithelial cells. The color shade of anthocyanins (i.e. flower color) depends largely on the structure of the anthocyanins, with more numerous hydroxyl groups on the B ring resulting in a bluer color. Hydroxylation of the B ring is catalyzed by flavonoid 3'-hydroxylase (F3'H) and flavonoid 3',5'-hydroxylase (F3'5'H). Absence of F3'H and F3'5'H activity leads to synthesis of pelargonidin (orange to red colors), presence of F3'H activity leads to synthesis of cyanidin (red to rouge colors) and presence of F3'5'H activity leads to synthesis of delphinidin (violet color).

These anthocyanidins are modified with sugars and acyl groups to produce an assortment of anthocyanins. Generally speaking, a larger number of modifying aromatic acyl groups correlates to bluer anthocyanins. Anthocyanins also produce quite different colors depending on the vacuole pH and the copresent flavonols and flavones or metal ions (Saito, N., Tanpakushitsu Kakusan Kouso, 47 202-209, 2002; Broullard and Dangles, In the flavonoids: Advances in Research since 1986 (Ed. by Harborne) Capmann and Hall, London pp. 565-588; Tanaka et al. Plant Cell Physiol. 39 1119-1126, 1998; Mol et al., Trends in Plant Science 3, 212-217, 1998; Mol et al., Curr. Opinion Biotechnol. 10, 198-201 1999).

Rose flower petal anthocyanins are derivatives of pelargonidin, cyanidin and peonidin, whereas no delphinidin derivatives are known (Biolley and May, J. Experimental Botany, 44, 1725-1734 1993; Mikanagi Y., Saito N., Yokoi M. and Tatsuzawa F. (2000) Biochem. Systematics Ecol. 28:887-902). This is considered to be the main reason for the lack of blue roses. Existing roses have been created by crossbreeding of crossable related rose species (*R. multiflora, R. chinensis, R. gigantean, R. moschata, R. gallica, R. whichuraiana, R. foetida*, etc.).

The fact that no blue rose has been achieved in spite of repeated efforts at crossbreeding is attributed to the lack of delphinidin production ability by rose-related varieties. Production of delphinidin in rose petals would require expression of F3'5'H in the petals as mentioned above, but F3'5'H is believed to be non-expressed in the petals of rose and rose-related varieties. Thus, it is likely impossible to obtain a blue rose by accumulating delphinidin in the petals through crossbreeding. It is known that trace amounts of the blue pigment rosacyanin are found in rose petals and its chemical structure has been determined (Japanese Unexamined Patent Publication No. 2002-201372), but no reports are known regarding augmentation of rosacyanin to create a blue rose, and no findings have been published on the rosacyanin biosynthesis pathway or the relevant enzymes or genes.

Examples of blue or violet colors produced by biological organisms also include indigo plant-produced indigo (for example, Appl. Microbiol. Biotechnol. February 2003, 60(6): 720-5) and microbially-produced violacein (J. Mol. Microbiol. Biotechnol. October 2000 2 (4):513-9; Org. Lett., Vol. 3, No. 13, 2001, 1981-1984), and their derivation from tryptophan and their biosynthetic pathways have been studied.

Blue pigments based on gardenia fruit-derived iridoid compounds (S. Fujikawa, Y. Fukui, K. Koga, T. Iwashita, H. Komura, K. Nomoto, (1987) Structure of genipocyanin G1, a spontaneous reaction product between genipin and glycine. Tetrahedron Lett. 28 (40), 4699-700; S. Fujikawa, Y. Fukui, K. Koga, J. Kumada, (1987), Brilliant skyblue pigment formation from gardenia fruits, J. Ferment. Technol. 65 (4), 419-24) and lichen-derived azulenes (Wako Pure Chemical Industries Co., Ltd.) are also known, but no reports are known of expressing these in plant flower petals to produce blue-colored flowers.

It has been expected that a blue rose could be created by transferring the F3'5'H gene expressed by other plants into rose and expressing it in rose petals (Saisho, H., "Aoi Bara", 2001, Shogakkan). The F3'5'H gene has been obtained from several plants including petunia, gentian and *Eustoma russellianum* (Holton et al. Nature 366, 276-279, 1993; Tanaka et al. Plan Cell Physiol. 37, 711-716 1996; WO93/18155). There are also reports of transformed varieties of rose (for example, Firoozababy et al. Bio/Technology 12:609-613 (1994); U.S. Pat. No. 5,480,789; U.S. Pat. No. 5,792,927; EP 536,327 A1; US 20010007157 A1).

Actual transfer of the petunia F3'5'H gene into rose has also been reported (WO93/18155, WO94/28140).

However, it has not been possible to obtain a blue rose, and it is believed that obtaining a blue rose will require a modification which alters the metabolism of flower pigments suited for rose.

On the other hand, it has been confirmed that transfer of the F3'5'H gene into red carnation, which produces pelargonidin instead of delphinidin, leads to accumulation of both pelargonidin and delphinidin, but that the flower color is only altered to a slightly purplish red (WO94/28140). This result suggests that it is not possible to obtain a "blue" carnation simply by expression of F3'5'H, and that it is necessary to inhibit the metabolic pathway to endogenous synthesis of pelargonidin by carnation.

In order to avoid competition with the carnation endogenous metabolic pathway (reduction of dihydrokaempferol (DHK) by dihydroflavonol reductase (DFR)), a variety lacking DFR was selected from among white carnations. The F3'5'H gene and petunia DFR (which is known to efficiently reduce dihydromyricetin (DHM) without reducing DHK) gene were transferred into carnation. This resulted in one case of successfully obtaining a recombinant carnation with a delphinidin content of about 100% and a blue-violet flower color previously not found in carnation (Tanpakushitsu Kakusan Kouso, Vol. 47, No. 3, p 225, 2002). Thus, further modification was necessary to realize a blue carnation flower, in addition to accumulating delphinidin by expression of the F3'5'H gene.

DFR has already been cloned from several plants (petunia, tobacco, rose, *Torenia*, snapdragon, transvaal daisy, orchid, barley, corn, etc.) (Meyer et al., Nature 330, 677-678, 1987; Helariutta et al., Plant Mol. Biol. 22, 183-193 1993; Tanaka et al., Plant Cell Physiol. 36, 1023-1031; Johnson et al., Plant J. 19, 81-85, 1999). Substrate specificity of the DFR gene differs depending on the plant variety, and it is known that the petunia, tobacco and orchid DFR genes cannot reduce DHK, whereas the petunia DFR gene most efficiently reduces DHM among the dihydroflavonols (Forkmann et al., Z. Naturforsch. 42c, 1146-1148, 1987; Johnson et al. Plant J. 19, 81-85, 1999). Nevertheless, no cases have been reported for expression of these DFR genes in rose.

As a means of avoiding competition with the endogenous metabolic pathway or between the enzyme and the exogenous gene-derived enzyme such as F3'5'H, as mentioned above, the gene may be transferred into a variety lacking the gene. Also, it is known that expression of the target gene can be artificially inhibited by deletion methods involving homologous recombination of the target gene, but because of the low frequency of homologous recombination and the limited number of suitable plant varieties, this has not been implemented in practice (for example, Nat. Biotechnol. 2002, 20:1030-4).

Inhibition methods on the transcription level include the antisense method using antisense RNA transcripts for mRNA of the target gene (van der Krol et al., Nature 333, 866-869, 1988), the sense (cosuppression) method using transcripts of RNA equivalent to mRNA of the target gene (Napoli et al., Plant Cell 2, 279-289, 1990) and a method of using duplex RNA transcripts corresponding to mRNA of the target gene (RNAi method; Waterhouse et al., Pro. Natl. Acad. Sci. USA 95, 13959-13964, 1998).

Numerous successful examples of these three methods have been published. For rose, cosuppression of chalcone synthase (CHS) gene which is necessary for synthesis of anthocyanins was reported to successfully alter flower color from red to pink (Gutterson HortScience 30:964-966 1995), but this CHS suppression is incomplete and therefore it has not been possible to totally suppress anthocyanin synthesis to obtain a white flower stock.

Patent document 1: Japanese Unexamined Patent Publication No. 2002-201372
Patent document 2: WO93/18155
Patent document 3: U.S. Pat. No. 5,480,789
Patent document 4: U.S. Pat. No. 5,792,927
Patent document 5: EP 536 327 A1
Patent document 6: US 20010007157 A1
Patent document 7: WO94/28140
Non-patent document 1: Honda T. et al. Gendai Kagaku, May, 25-32 (1998)
Non-patent document 2: Tanaka et al. Plant Cell Physiol. 39, 1119-1126, 1998
Non-patent document 3: Mol et al. Curr. Opinion Biotechnol. 10, 198-201 1999
Non-patent, document 4: Oba, H., "Bara no Tanjo", 1997, Chukoshinsho
Non-patent document Suzuki, M., "Shokubutsu Bio no Mahou: Aoi Bara mo Yume dewanakunatta", 1990, Kodansha Bluebacks
Non-patent document 6: Saisho, H., "Aoi Bara", 2001, Shogakkan
Non-patent document 7: Saito, N., Tanpakushitsu Kakusan Kouso, 47 202-209, 2002
Non-patent document 8: Broullard et al. In the flavonoids: Advances in Research since 1986 (Ed by Harborne) Capmann and Hall, London pp 565-588
Non-patent document 9: Tanaka et al. Plant Cell Physiol. 39 1119-1126, 1998
Non-patent document 10: Mol et al, Trends in Plant Science 3, 212-217 1998
Non-patent document 11: Mol et al. Curr. Opinion Biotech. 10, 198-201 1999
Non-patent document 12: Biolley and May, J. Experimental Botany, 44, 1725-1734 1993
Non-patent document 13: Mikanagi Y, et al. (2000) Biochem Systematics Ecol. 28:887-902

Non-patent document 14: Appl. Microbiol. Biotechnol. 2003 February; 60(6):720-5
Non-patent document 15: J. Mol. Microbiol. Biotechnol. 2000 October; 2 (4): 513-9
Non-patent document 16: Org. Lett., Vol. 3, No. 13, 2001, 1981-1984
Non-patent document 17: S. Fujikawa, et al. (1987) Tetrahedron Lett. 28 (40), 4699-700
Non-patent document 18: S. Fujikawa, et al. (1987) J. Ferment. Technol. 65 (4), 419-24
Non-patent document 19: Holton et al. Nature 366, 276-279, 1993
Non-patent document 20: Tanaka et al. Plant Cell Physiol. 37, 711-716 1996
Non-patent document 21: Firoozababy et al. Bio/Technology 12:609-613 (1994)
Non-patent document 22: Tanpakushitsu Kakusan Kouso, Vol. 47, No. 3, p 225, 2002
Non-patent document 23: Meyer et al. Nature 330, 677-678, 1987
Non-patent document 24: Helariutta et al. Plant Mol. Biol. 22 183-193 1993
Non-patent document 25: Tanaka et al. Plant Cell Physiol. 36, 1023-1031
Non-patent document 26: Johnson et al. Plant J. 19, 81-85, 1999
Non-patent document 27: Forkmann et al. Z. Naturforsch. 42c, 1146-1148, 1987
Non-patent document 28: Nat Biotechnol 2002, 20:1030-4
Non-patent document 29: van der Krol et al. Nature 333, 866-869, 1988
Non-patent document 30: Napoli et al. Plant Cell 2, 279-289, 1990
Non-patent document 31: Waterhouse et al. Pro. Natl. Acad. Sci. USA 95, 13959-13964 1998
Non-patent document 32: Gutterson HortScience 30:964-966 1995
Non-patent document 33: Suzuki, S., "Bara, Hanazufu", Shogakkann, p. 256-260, 1990

DISCLOSURE OF THE INVENTION

As mentioned above, rose flower colors have been successfully altered by transferring the F3'5'H gene into rose and expressing it in the petals. In carnation, the F3'5'H gene and petunia DFR gene have been expressed in DFR-deficient varieties to create blue-violet carnations. However, a "blue rose" has not yet been created. It is therefore an object of the present invention to provide a rose which blossoms with a blue flower.

The invention thus provides (1) a method for producing a rose characterized by artificially suppressing the rose endogenous metabolic pathway and expressing the pansy gene coding for flavonoid 3',5'-hydroxylase.

The invention further provides (2) a method for producing a rose characterized by artificially suppressing the rose endogenous metabolic pathway, and expressing the pansy gene coding for flavonoid 3',5'-hydroxylase and the gene coding for dihydroflavonol reductase.

The invention still further provides (3) a method for producing a rose characterized by artificially suppressing expression of rose endogenous dihydroflavonol reductase, and expressing the pansy gene coding for flavonoid 3',5'-hydroxylase and the gene coding for dihydroflavonol reductase derived from a plant other than rose.

The invention still further provides (4) a method for producing a rose characterized by artificially suppressing expression of rose endogenous flavonoid 3'-hydroxylase and expressing the pansy gene coding for flavonoid 3',5'-hydroxylase.

The aforementioned pansy gene coding for flavonoid 3',5'-hydroxylase is, for example, the gene listed as SEQ ID NO: 1 or SEQ ID NO: 3. The gene coding for dihydroflavonol reductase is preferably derived from iris, Nierembergia, petunia, orchid, gentian or Eustoma russellianum.

The invention still further provides (5) a rose obtained by the production method according to any one of (1) to (4) above, or a progeny or tissue thereof having the same properties as the rose.

The invention still further provides (6) a rose obtained by the production method according to any one of (1) to (4) above, or a progeny or tissue thereof, wherein the petal color of the rose is violet, blue-violet or blue.

The invention further provides (7) a rose according to (6) above, or a progeny or tissue thereof, wherein the petal color of the rose belongs to the "Violet group", "Violet-Blue" group or "Blue group" according to the Royal Horticultural Society Colour Chart (RHSCC).

The invention further provides (8) a rose according to (7) above, or a progeny or tissue thereof, wherein the petal color of the rose belongs to "Violet group" 85a or 85b according to the Royal Horticultural Society Colour Chart (RHSCC).

BEST MODE FOR CARRYING OUT THE INVENTION

Figure 1:
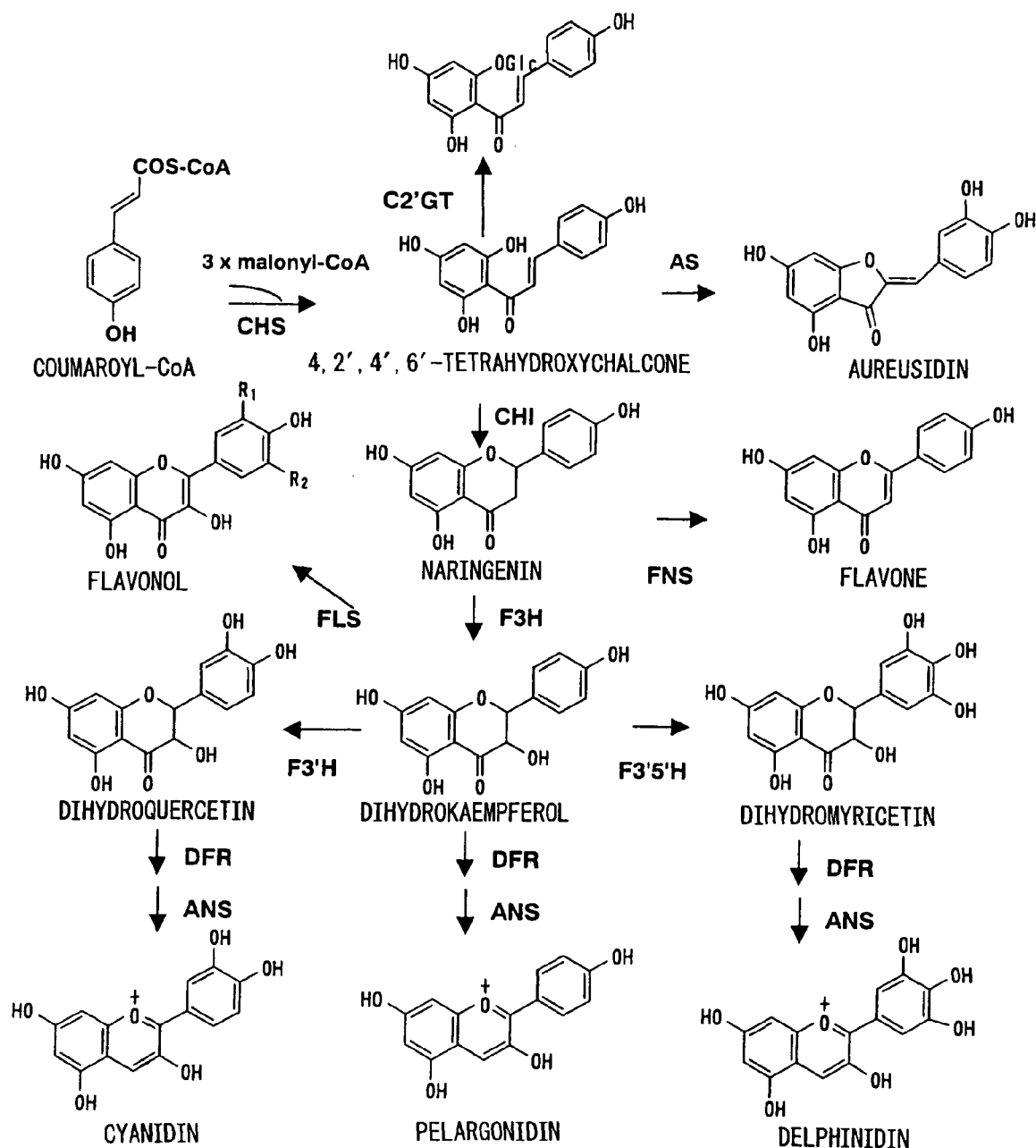
FIG. 1 shows the flavonoid biosynthesis pathway.
CHS: Chalcone synthase, CHI: Chalcone isomerase FNS: Flavone synthase, F3H: Flavanone 3-hydroxylase
F3'H: Flavonoid 3'-hydroxylase
F3'5'H: Flavonoid 3'5'-hydroxylase, FLS: Flavonol synthase
DFR: Dihydroflavonol 4-reductase
ANS: Anthocyanidin synthase, AS: Aurone synthase
C2'GT: Chalcone 2'-glucosyl transferase

Several reasons may be postulated for a lack of blue color in rose even with production of delphinidin. The stability, solubility and color of anthocyanins varies depending on modification with acyl groups and sugars. Specifically, it is known that an increased number of aromatic acyl groups results in greater blueness. Also, formation of complexes between flavonol and flavone copigments and anthocyanins produce a blue color and shift the maximum absorption wavelength toward the longer wavelength end while also increasing the absorbance. Anthocyanin color is also dependent on pH. Since a lower pH tends toward redness and a more neutral pH produces blueness, the flower color depends on the pH of the vacuoles in which the anthocyanins are localized. In addition, formation of metal chelates in the copresence of metal ions such as $Al^{3+}$ and $Mg^{2+}$ can significantly affect flower color as well. Trial and error and assiduous research led to the proposal for a modification whereby the proportion of delphinidin in flower petals is increased.

First, it was attempted to create a blue rose by the same method used to create a blue-violet carnation. Specifically, it was attempted to analyze white rose variety 112 and identify a DFR-deficient line, but unlike carnation, no completely DFR-deficient line could be obtained. This is presumably due to the fact that carnation is diploid while ordinarily cultivated rose is tetraploid, such that it is difficult to find a line deficient in a single gene.

Next, the pansy F3'5'H gene and petunia DFR gene were transferred into the white flower variety Tineke and accumulation of delphinidin was detected, but the amount was minimal and a blue rose was not obtained.

According to the present invention, the DFR gene, an enzyme participating in the rose endogenous flavonoid synthesis pathway, is artificially suppressed by a gene engineering technique, and the pansy F3'5'H gene is expressed while a dihydromyricetin-reducing DFR gene is also expressed, in order to increase the delphinidin content to roughly 80-100% of the total anthocyanidins in the flower petals, thereby allowing realization of a blue rose.

The dihydromyricetin-reducing DFR genes used in this case were derived from iris (Iridaceae), *Nierembergia* (Solanaceae) and petunia (Solanaceae), but as other dihydromyricetin-reducing DFR gene sources there may be mentioned non-pelargonidin-accumulating plants such as tobacco (Solanaceae), cyclamen (Primulaceae), delphinium (Ranunculaceae), orchid (Orchidaceae), gentian (Gentianaceae), *Eustoma russellianum* (Gentianaceae) and the like (Forkmann 1991, Plant Breeding 106, 1-26; Johnson et al., Plant J. 1999, 19, 81-85). The DFR genes used for the present invention are genes that preferentially reduce dihydromyricetin.

According to the invention, the flavonoid 3'-hydroxylase (F3'H) gene, an enzyme participating in the rose endogenous flavonoid synthesis pathway, is artificially suppressed by a gene engineering technique, and the pansy F3'5'H gene is expressed, in order to increase the delphinidin content to roughly 80-100% of the total anthocyanidins in the flower petals, thereby allowing realization of a blue rose.

The roses obtained according to the invention have hitherto non-existent flower colors, and the invention can provide roses with flower colors belonging not only to the red-purple group, purple group and purple-violet group but also to the violet group, violet-blue group and blue group, according to the Royal Horticultural Society Colour Chart.

EXAMPLES

The present invention will now be explained in greater detail by the following examples. Unless otherwise specified, the molecular biological protocols used were based on Molecular Cloning (Sambrook and Russell, 2001, Cold Spring Harbor Laboratory Press, Cold Spring Harbor, N.Y.).

Example 1

Flower Color Measuring Method

The flower petal color shade was evaluated by measurement using a CM2022 spectrophotometric colorimeter (Minolta Japan) with a 10° visual field and a D65 light source, and analysis using SpectraMagic color control software (Minolta Japan). The Royal Horticultural Society Colour Chart (RHSCC) number is the nearest color as compared against Color Classification System Version 2.1.1 (The Japan Research Institute Co., Ltd.; Japanese Unexamined Patent Publication No. 2002-016935), based on the color value (CIE L*a*b* color system) obtained by visual discrimination and measurement with the device mentioned above. This system may be used for objective selection of the nearest RHSCC number.

Upon measuring the color shades of flower petals of cultivars conventionally referred to as "blue roses" and determining the nearest colors according to the RHSCC by this method, it was determined that Blue Moon and Madam Violet were 186d (Greyed-Purple group), Lavande was 186c (Greyed-Purple group), Seiryu was 189d (Greyed-Green group) and Blue Heaven was 198d (Greyed-Green group). These cultivars are called blue roses but are classified in "Grey" groups according to RHSCC number and therefore do not exhibit the blue color which is the object of the present invention.

Example 2

Flavonoid Analysis

1) Extraction of Flower Petal Color

A 0.5 g portion of freeze-dried rose petals was subjected to extraction in 4 ml of 50% acetonitrile ($CH_3CN$) containing 0.1% TFA for 20 minutes under ultrasonic vibration and then filtered with a 0.45 μm filter. High-performance liquid chromatography (HPLC) of the anthocyanins in the extract was conducted under the following conditions. Isocratic elution was carried out using an RSpak DE-413L (4.6 mmϕ×25 cm, Shoko Co., Ltd.) column with a flow rate of 0.6 ml/min, and a mobile phase at a linear concentration gradient of 10%→50% $CH_3CN/H_2O$ containing 0.5% trifluoroacetic acid (TFA) for 15 minutes followed by 50% $CH_3CN/H_2O$ containing 0.5% TFA for 10 minutes. Detection was performed using an SPD-M10A photodiode array detector (Shimadzu Laboratories), with detection in the wavelength range of 600-250 nm and calculation of the abundance ratio of each anthocyanin based on the 520 nm absorbance area.

2) Anthocyanidin Analysis

A 0.2 ml portion of the filtrate was dried completely under reduced pressure in a glass test tube and dissolved in 0.2 ml of 6N hydrochloric acid (HCl), and subjected to hydrolysis at 100° C. for 20 minutes. The hydrolyzed anthocyanidins were extracted with 0.2 ml of 1-pentanol, and the organic layer was analyzed by HPLC under the following conditions. The column used was an ODS-A312 (6 mmϕ×15 cm, YMC Co., Ltd.), and elution was performed at a flow rate of 1 ml/min using a $CH_3COOH:CH_3OH:H_2O=15:20:65$ solution as the mobile phase.

Detection was performed by spectral measurement at 600-400 nm using an SPD-M10A photodiode array detector (Shimadzu Laboratories), identification based on absorption maximum (λmax) and retention time (RT), and quantitation based on 520 nm absorbance area. The retention time and λmax of delphinidin and cyanidin under these HPLC conditions were 4.0 min, 5.2 min and 534 nm, 525 nm, respectively. Delphinidin hydrochloride and cyanidin hydrochloride purchased from Funakoshi Co., Ltd. were used as samples for identification and quantitation.

3) Flavonol Analysis

A 0.2 ml portion of the flower petal-extracted filtrate was dried to hardness under reduced pressure in a 1.5 ml Eppendorf tube and dissolved in 0.2 ml of 0.1 M potassium phosphate buffer (KPB) at pH 4.5, and then 6 units of β-glucosidase (Shinnihon Kagaku Co., Ltd.) and 1 unit of naringenase (Sigma Chemical Co., MO, USA) were added and the mixture was kept at 30° C. for 16 hours. After the reaction, 0.2 ml of 90% $CH_3CN$ was added to the enzyme reaction solution to terminate the reaction. The solution was filtered with a 0.45 μm filter and subjected to HPLC under the following conditions.

Isocratic elution was carried out using a Develosil C30-UG-5 (4.6 mmφ×15 cm, Nomura Chemical Co., Ltd.) column with a flow rate of 0.6 ml/min, and a mobile phase at a linear concentration gradient of 18%-+63% $CH_3CN/H_2O$ containing 0.1% TFA for 10 minutes followed by 63% $CH_3CN/H_2O$ containing 0.1% TFA for 10 minutes. Detection was performed using an SPD-M10A photodiode array detector, with detection in the wavelength range of 400-250 nm. The R.T. and λmax of kaempferol and quercetin under these conditions were 11.6 min, 365 nm and 10.3 min, 370 nm, respectively. Kaempferol and quercetin purchased from Funakoshi Co., Ltd. were used as samples for quantitation based on the A330 nm area.

Example 3 pH Measurement Method

Approximately 2 g of rose petals frozen at −80° C. for 1 hour or longer was pressed with a homogenizer to obtain the petal juice. The pH was measured by connecting a 6069-10C microelectrode (Horiba Laboratories) to a pH meter (F-22, Horiba Laboratories).

Example 4

Transformation of Rose

Several methods have been reported for transformation of roses (for example, Firoozababy et al. Bio/Technology 12:609-613 (1994); U.S. Pat. No. 5,480,789; U.S. Pat. No. 5,792,927; EP 536,327 A1; US 20010007157 A1), and transformation may be carried out by any of these techniques. Specifically, rose calli taken from aseptic seedling leaves were immersed for 5 minutes in a bacterial suspension of *Agrobacterium tumefaciens* Ag10 (Lazo et al., Bio/Technology 9:963-967, 1991), the excess bacterial suspension was wiped off with sterile filter paper, and the calli were transferred to subculturing medium and cocultivated for 2 days in a dark room.

After subsequently rinsing with MS liquid medium containing 400 mg/L carbenicillin, the calli were transferred to selection/elimination medium prepared by adding 50 mg/L kanamycin and 200 mg/L carbenicillin to subculturing medium. Upon repeating transfer and cultivation of the portions which grew normally in selection medium without growth inhibition, the kanamycin-resistant calli were selected out. The kanamycin-resistant transformed calli were cultivated in redifferentiation medium containing 50 mg/L kanamycin and 200 mg/L carbenicillin to obtain kanamycin-resistant shoots. The obtained shoots were rooted in 1/2MS medium and then habituated. The habituated plants were potted and then cultivated in a closed greenhouse until blooming.

Example 5

Obtaining Rose Flavonoid Gene

A cDNA library derived from Kardinal rose variety flower petals was screened using the petunia DFR gene (described in WO96/36716) as the probe, to obtain rose DFR cDNA was which designated as pCGP645. The details have already been reported (Tanaka et al., Plant Cell Physiol. 36, 1023-1031 1995).

Likewise, the same library was screened with the petunia chalcone synthase-A (CHS-A) gene (Koes et al., Gene (1989) 81, 245-257) and the anthocyanidin synthase (ANS) gene (Martin et al., Plant J., (1991) 1, 37-49) according to a publicly known procedure (Tanaka et al., Plant Cell Physiol. 36, 1023-1031 1995), to obtain rose chalcone synthase (CHS) and anthocyanidin synthase (ANS) homologs which were designated as pCGP634 and pCGP1375, respectively. The nucleotide sequence for rose CHS is listed as SEQ ID NO: 5, and the nucleotide sequence for rose ANS is listed as SEQ ID NO: 6.

Example 6

Screening for White Rose

For creation of a blue cultivar by gene recombination, cultivars lacking only the DFR gene may be selected, in order to avoid competition between the endogenous anthocyanin synthesis pathway and the introduced genes (particularly the F3'5'H gene), and the petunia DFR gene and F3'5H gene transferred into those cultivars (WO96/36716).

A screening was conducted among the numerous existing white rose varieties, for those lacking only the DFR gene and normally expressing other anthocyanin biosynthesis enzyme genes. The cause of flower color whitening is believed to be occasional mutation or deletion of structural genes involved in anthocyanin biosynthesis, and occasional loss of transcription regulating factors which control transcription of structural genes involved in anthocyanin biosynthesis. Roses lacking DFR gene mRNA were examined according to the method described in WO96/36716.

First, 112 primarily white rose lines were analyzed for flavonoid composition of the flower petals by the method described in Example 1, and lines with high accumulation of flavonols were selected. The pH of each petal juice was then measured and 80 cultivars with relatively high pH values were chosen as primary candidates.

RNA was then extracted from petals of these cultivars. The RNA extraction was accomplished by a publicly known method (Tanaka et al., Plant Cell Physiol. 36, 1023-1031, 1995). The obtained RNA was used to examine the presence or absence of mRNA corresponding to the rose DFR gene (Tanaka et al., Plant Cell Physiol. 36, 1023-1031, 1995) and the rose anthocyanidin synthase (ANS) gene. RT-PCR was performed and eight cultivars (WKS-11, 13, 22, 36, 43, White Killarney, Tsuru No. 2, Tineke) having low endogenous expression of DFR mRNA and normal ANS mRNA levels were selected.

RT-PCR was carried out with a Script First-strand Synthesis System for RT-PCR (Invitrogen) using RNA obtained from petals of each cultivar. The DFR mRNA was detected using DFR-2F (5'-CAAGCAATGGCATCGGAATC-3') (SEQ ID NO: 13) and DFR-2B (5'-TTTCCAGTGAGTGGC-GAAAGTC-3') (SEQ ID NO: 14) primers, and the ANS mRNA was detected using ANS-2F (5'-TGGACTCGAA-GAACTCGTCC-3') (SEQ ID NO: 15) and ANS-2B (5'-CCT-CACCTTCTCCCTTGTT-3') (SEQ ID NO: 16) primers.

These eight cultivars showed lower levels of DFR mRNA and normal levels of ANS mRNA in Northern blotting (Table 1), and their cultivating properties were excellent. Two of the transformable cultivars (Tineke, WKS36) were decided on for actual transfer of the delphinidin-producing construct.

TABLE 1

| Cultivar name | Flavonols (mg/g petal) | | | pH | RT-PCR | | |
|---|---|---|---|---|---|---|---|
| | Q | K | Total | | DFR | CHS | ANS |
| WKS-36 | 0.082 | 8.095 | 8.177 | 4.81 | − | + | + |
| White Killarney | 1.343 | 6.113 | 7.456 | 4.7 | + | + | + |
| Tsuru No. 2 | 0.715 | 5.188 | 5.903 | 4.7 | + | + | + |
| WKS-11 | 2.028 | 0.475 | 2.503 | 4.51 | + | + | + |
| Tineke | 0.097 | 4.337 | 4.434 | 4.45 | − | + | + |
| WKS-13 | 0.320 | 3.993 | 4.313 | 4.45 | − | + | + |
| WKS-22 | 0.145 | 10.469 | 10.614 | 4.41 | − | + | + |
| WKS-43 | 0.045 | 2.104 | 2.149 | 4.07 | − | + | + |

+: mRNA detected at same level as colored rose (Rote Rose cultivar)
−: mRNA detected at lower level than colored rose (Rote Rose cultivar)
Q: Quercetin,
K: kaempferol Example 7

Transfer of Rose DFR Gene into Tineke

Plasmid pE2113 (Mitsuhara et al., Plant Cell Physiol. 37, 49-59, 1996) comprises the enhancer sequence repeat-containing cauliflower mosaic virus 35S (E1235S) promoter and the nopaline synthase terminator. This plasmid was digested with SacI and the ends were blunted using a Blunting Kit (Takara). The DNA fragment was ligated with an 8 bp SalI linker (Takara) and the obtained plasmid was designated as pUE5.

Figure 2:
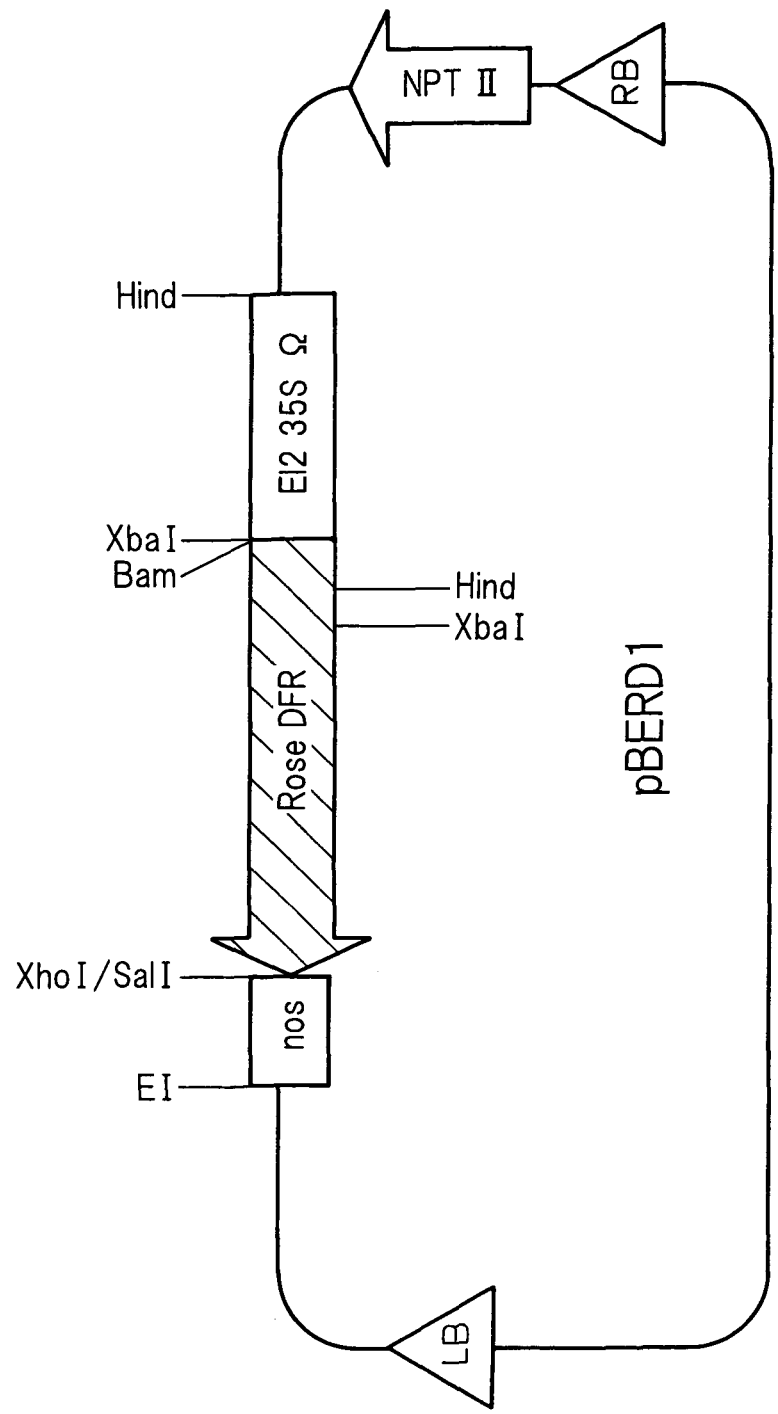
FIG. 2 shows the structure of plasmid pBERD1.

Plasmid pUE5 was digested with HindIII and EcoRI to obtain an approximately 3 kb DNA fragment, which was introduced into pBin19 (Bevan M., Binary Agrobacterium Vector for plant transformation. Nucl. Acid Res. 12. 8711-21, 1984) previously digested with HindIII and EcoRI, to obtain plasmid pBE5. Next, pCGP645 was digested with BamHI and XhoI to obtain a DNA fragment containing full-length rose DFR cDNA. This was ligated with pBE5 digested with BamHI and XhoI to construct pBERD1 (FIG. 2). The plasmid was transferred into *Agrobacterium tumefaciens* Ag10.

Plasmid pBERD1 (FIG. 2) was transferred into the white rose cultivar "Tineke", and 18 transformants were obtained. Flower color was altered in six of the obtained transformants. Pigment analysis of two plants in which a clear color change from white to pink was observed confirmed accumulation of cyanidin and pelargonidin in both (Table 2). These results suggested that the Tineke cultivar is a cultivar lacking the DFR gene.

TABLE 2

| Plant No. | Cya (mg/g) | Pel (mg/g) |
|---|---|---|
| 1 | 0.014 | 0.005 |
| 2 | 0.014 | 0.006 |

Cya: Cyanidin, Pel: Pelargonidin

Example 8

Transfer of Pansy F3'5'H Gene (#18) and Petunia DFR Gene into Tineke

RNA was extracted from young budding pansy (Black Pansy variety) petals by the method of Turpen and Griffith (BioTechniques 4:11-15, 1986), and Oligotex-dT (Qiagen) was used for purification of polyA+RNA. This polyA+RNA and a λZAPII/GigapackII Cloning Kit (Stratagene) were used to construct a cDNA library from the young budding pansy petals. After transferring approximately 100,000 pfu of phage plaques grown on an NZY plate onto a Colony/PlaqueScreen (DuPont), treatment was conducted by the manufacturer's recommended protocol. The plaques were $^{32}$P-labeled and screened using petunia Hf1cDNA (pCGP602, Holton et al., Nature, 366, p 276-279, 1993) as the probe.

The membrane was subjected to pre-hybridization for 1 hour at 42° C. in hybridization buffer (10% (v/v) formamide, 1 M NaCl, 10% (w/v) dextran sulfate, 1% SDS), and then the $^{32}$P-labeled probe was added to 1×10$^6$ cpm/ml and hybridization was performed for 16 hours at 42° C. The membrane was then rinsed for 1 hour in 2×SSC, 1% SDS at 42° C., fresh rinsing solution was exchanged, and rinsing was again performed for 1 hour. The rinsed membrane was exposed on a Kodak XAR film together with an intensifying screen, and the hybridization signal was detected.

The results of cDNA analysis demonstrated that the two obtained cDNA had high identity with petunia Hf1. The two cDNA types were designated as pansy F3'5'H cDNA, BP#18 (pCGP1959) and BP#40 (pCGP1961). The nucleotide sequence for #18 is listed as SEQ ID NO: 1, and its corresponding amino acid sequence is listed as SEQ ID NO: 2, the nucleotide sequence for #40 is listed as SEQ ID No. 3, and its corresponding amino acid sequence is listed as SEQ ID NO: 4. BP#18 and BP#40 have 82% identity on the DNA level. Also, BP#18 and BP#40 both exhibit 60% identity with petunia Hf1 and 62% identity with petunia Hf2 (Holton et al., Nature, 366, p 276-279, 1993), on the DNA level.

Separately, plasmid pUE5 was digested with EcoRI and the ends were blunted using a Blunting Kit (Takara), and the obtained DNA fragment was ligated with an 8 bp HindIII linker (Takara), producing a plasmid which was designated as pUE5H. There was recovered an approximately 1.8 kb DNA fragment obtained by subjecting plasmid pCGP1959 containing pansy F3'5'H #18 cDNA to complete digestion with BamHI and partial digestion with XhoI. The plasmid obtained by ligation of this with pUE5H digested with BamHI and XhoI was designated as pUEBP18.

Figure 3:
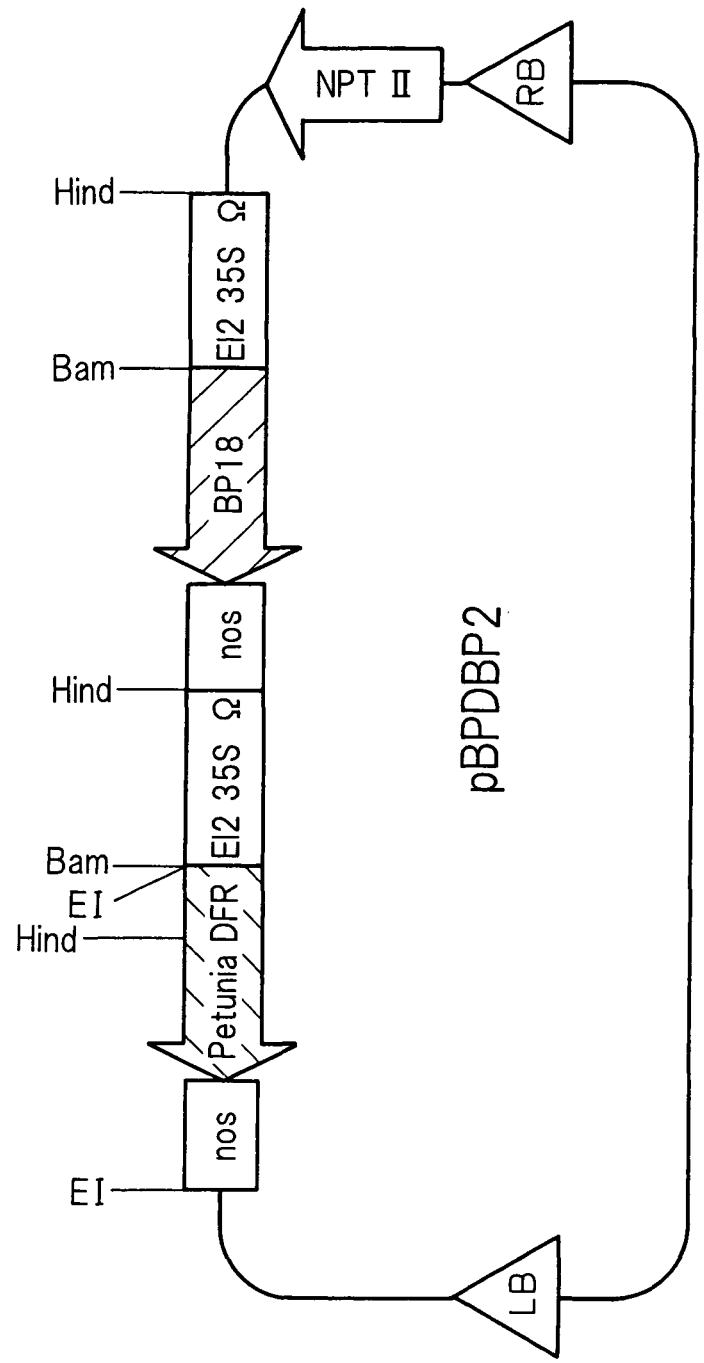
FIG. 3 shows the structure of plasmid pBPDBP2.

Separately, a DNA fragment containing petunia DFR cDNA was recovered by digestion of pCGP1403 (WO96/36716) with BamHI and XhoI, and this DNA fragment was ligated with pBE5 that had been digested with BamHI and XhoI, to prepare pBEPD2. Next, pUEBP18 was partially digested with HindIII and an approximately 2.8 kb DNA fragment was recovered containing the E1235S promoter, pansy F3'5'H #18 cDNA and the nos terminator. This fragment was ligated with a DNA fragment obtained by partial digestion of pBEPD2 with HindIII to obtain a binary vector plasmid pBPDBP2 (FIG. 3). This plasmid was introduced into *Agrobacterium tumefaciens* Ag10.

Plasmid pBPDBP2 (FIG. 3) was transferred into the white rose cultivar "Tineke", and 40 transformants were obtained. Flower color was altered in 23 of the obtained transformants, and pigment analysis confirmed accumulation of delphinidin in 16 of the 19 analyzed transformants (Table 3). The delphinidin content was 100% at maximum (average: 87%), but the maximum amount of pigment was very low at 0.035 mg per gram of petals and the flower color was only altered from RHS Color Chart 158d (Yellow-White group) to 56a (Red group) or 65b (Red-Purple group), while no color of the Violet group, Violet-Blue group or Blue group according to the RHSCC was achieved and the target blue rose could not be obtained.

TABLE 3

| Plant No. | Del content (%) | Del (mg/g) | Cya (mg/g) | M (mg/g) | Q (mg/g) | K (mg/g) |
|---|---|---|---|---|---|---|
| 1 | 87 | 0.002 | 0.000 | 0.000 | 0.058 | 0.354 |
| 2 | 100 | 0.004 | 0.000 | 0.338 | 0.059 | 1.921 |
| 3 | 82 | 0.002 | 0.001 | 0.203 | 0.039 | 1.382 |
| 4 | 100 | 0.003 | 0.000 | 0.245 | 0.050 | 1.840 |
| 5 | 76 | 0.005 | 0.001 | 0.000 | 0.280 | 3.288 |
| 6 | 0 | 0.000 | 0.000 | 0.000 | 0.098 | 0.409 |
| 7 | 0 | 0.000 | 0.001 | 0.000 | 0.101 | 0.358 |
| 8 | 0 | 0.000 | 0.001 | 0.000 | 0.030 | 2.277 |
| 9 | 83 | 0.013 | 0.003 | 0.000 | 0.117 | 0.841 |
| 10 | 85 | 0.011 | 0.002 | 0.000 | 0.104 | 3.300 |
| 11 | 84 | 0.020 | 0.004 | 0.000 | 0.168 | 3.137 |
| 12 | 91 | 0.025 | 0.002 | 0.294 | 0.119 | 1.252 |
| 13 | 90 | 0.028 | 0.003 | 0.000 | 0.075 | 1.912 |
| 14 | 91 | 0.014 | 0.001 | 0.000 | 0.152 | 2.667 |
| 15 | 90 | 0.035 | 0.004 | 0.000 | 0.086 | 1.616 |
| 16 | 83 | 0.023 | 0.005 | 0.000 | 0.117 | 2.267 |
| 17 | 91 | 0.014 | 0.001 | 0.000 | 0.113 | 0.825 |
| 18 | 76 | 0.003 | 0.001 | 0.000 | 0.085 | 2.351 |
| 19 | 82 | 0.005 | 0.001 | 0.000 | 0.054 | 1.616 |

Del: delphinidin,
M: Myricetin

Example 9

Transfer of Pansy F3'5'H Gene (#40) and Petunia DFR Gene into Tineke

Plasmid pE2113 (Mitsuhara et al., Plant Cell Physiol. 37, 49-59, 1996) was digested with HindIII and XbaI to obtain an approximately 800 bp DNA fragment, which was ligated with pBin19 (Bevan M., Binary Agrobacterium Vector for plant transformation. Nucl. Acid Res. 12. 8711-21, 1984) previously digested with HindIII and XbaI. The obtained plasmid was designated as pCGP1391. Another plasmid, pCGP669 (WO94/21840), contains the petunia chalcone synthase A (CHS-A) gene promoter. This plasmid was digested with EcoRI, blunted and then digested with HindIII.

The approximately 700 bp DNA fragment was ligated with pCGP1391 that had been digested with HindIII and SnaBI, and the obtained plasmid was designated as pCGP1707. Also, there was recovered an approximately 1.8 kb DNA fragment obtained by subjecting plasmid pCGP1961 containing pansy F3'5'H #40 cDNA to complete digestion with BamHI and partial digestion with XhoI. The plasmid obtained by ligation of this with pUE5H digested with BamHI and XhoI was designated as pUEBP40. Plasmid pUEBP40 was digested with EcoRV and XbaI and an approximately 5.5 kb DNA fragment was recovered.

Figure 4:
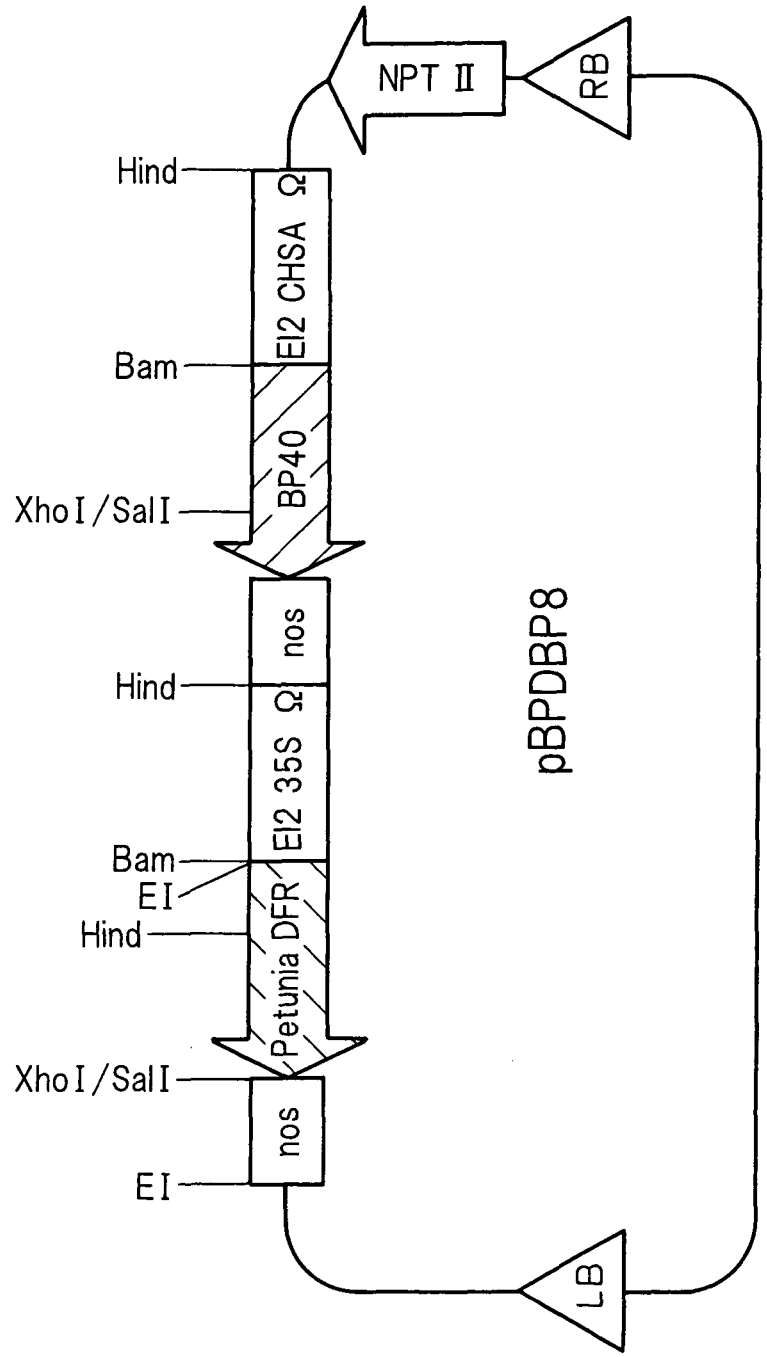
FIG. 4 shows the structure of plasmid pBPDBP8.

This fragment was ligated with an approximately 700 bp fragment obtained by digesting plasmid pCGP1707 with HindIII, blunting the ends and further digesting with XbaI, to obtain plasmid pUFBP40. Next, pUFBP40 was partially digested with HindIII and an approximately 3.4 kb DNA fragment was recovered containing the cauliflower 35S promoter enhancer, CHS-A promoter, pansy F3'5'H #40 cDNA and the nos terminator. This fragment was ligated with a DNA fragment obtained by partial digestion of pBEPD2 with HindIII to obtain a binary vector plasmid pBPDBP8 (FIG. 4). This plasmid was introduced into *Agrobacterium tumefaciens* Ag10.

Plasmid pBPDBP8 (FIG. 4) was transferred into the white rose cultivar "Tineke", and 53 transformants were obtained. Flower color was altered in 17 of the obtained transformants, and pigment analysis confirmed accumulation of delphinidin in 8 of the 9 analyzed transformants (Table 4). The delphinidin content was 93% at maximum (average: 79%), but the maximum amount of pigment was very low at 0.014 mg per gram of petals and the flower color was only altered from RHS Color Chart 158d (Yellow-White group) to 56a (Red group) or 65b (Red-Purple group), while no color of the Violet group, Violet-Blue group or Blue group according to the RHSCC was achieved and the target blue rose could not be obtained. This suggested that the Tineke variety is not a variety lacking only the DFR gene.

TABLE 4

| Plant No. | Del content (%) | Del (mg/g) | Cya (mg/g) | M (mg/g) | Q (mg/g) | K (mg/g) |
|---|---|---|---|---|---|---|
| 1 | 0 | 0.000 | 0.001 | 0.000 | 0.018 | 2.023 |
| 2 | 9 | 0.001 | 0.006 | na | na | na |
| 3 | 93 | 0.011 | 0.001 | 0.000 | 0.036 | 2.724 |
| 4 | 86 | 0.007 | 0.001 | 0.000 | 0.076 | 2.957 |
| 5 | 71 | 0.013 | 0.006 | 0.000 | 0.073 | 2.503 |
| 6 | 87 | 0.014 | 0.002 | 0.000 | 0.058 | 3.390 |
| 7 | 78 | 0.005 | 0.002 | 0.000 | 0.049 | 1.241 |
| 8 | 47 | 0.004 | 0.004 | 0.000 | 0.070 | 1.800 |
| 9 | 78 | 0.004 | 0.001 | 0.000 | 0.029 | 2.326 | na: no analysis/measurement

Example 10

Transfer of Pansy F3'5'H Gene (#18) and Petunia DFR Gene into WKS36

Plasmid pBPDBP2 (FIG. 3) was transferred into the white rose "WKS36", and 138 transformants were obtained. Flower color was altered in 10 of the obtained transformants, and accumulation of delphinidin was confirmed in all of the plants (Table 5). The delphinidin content was 91% at maximum (average: 60%), but the maximum amount of pigment was very low at 0.033 mg per gram of petals and the flower color was only altered to very light pink, while no color of the Violet group, Violet-Blue group or Blue group according to the RHSCC was achieved and the target blue rose could not be obtained. This suggested that the WKS36 variety is not a variety lacking only the DFR gene.

TABLE 5

| Plant No. | Del content (%) | Del (mg/g) | Cya (mg/g) | M (mg/g) | Q (mg/g) | K (mg/g) |
|---|---|---|---|---|---|---|
| 1 | 60 | 0.008 | 0.005 | 0.381 | 0.169 | 2.291 |
| 2 | 40 | 0.006 | 0.009 | 0.633 | 0.486 | 2.911 |
| 3 | 54 | 0.005 | 0.005 | 0.654 | 0.336 | 3.460 |
| 4 | 43 | 0.016 | 0.021 | 0.000 | 0.656 | 2.469 |
| 5 | 53 | 0.009 | 0.008 | 0.404 | 0.325 | 2.397 |
| 6 | 53 | 0.004 | 0.003 | 0.498 | 0.251 | 2.768 |
| 7 | 45 | 0.013 | 0.016 | 0.000 | 0.381 | 1.537 |
| 8 | 83 | 0.004 | 0.001 | 0.000 | 0.156 | 1.632 |
| 9 | 80 | 0.033 | 0.008 | 0.000 | 0.557 | 3.766 |
| 10 | 91 | 0.013 | 0.000 | 0.000 | 0.184 | 2.610 |

Example 11

Transfer of Pansy F3'5'H Gene (#18) and Petunia DFR Gene into WKS36

A plasmid obtained by replacing the AscI site of plasmid pUCAP (van Engelen et al., Transgenic Research 4, 288-290, 1995) with PacI linker was designated as pUCPP. Separately, an expression cassette prepared by linking the rose chalcone synthase promoter, pansy F3'5'H #18 cDNA and nos terminator was obtained in the following manner.

Chromosomal DNA was extracted from young leaves of the Kardinal rose cultivar (Tanaka et al., Plant Cell Physiol. 36, 1023-1031, 1995). An approximately 100 µg portion of DNA was partially digested with Sau3AI, and approximately 20-kb DNA fragments were recovered by sucrose density gradient.

These were ligated with lambda phage EMBL3 (for example, Stratagene) that had been digested with BamHI, and a chromosomal DNA library was prepared by the manufacturer's recommended protocol. The library was screened by a publicly known method (Tanaka et al., Plant Cell Physiol. 36, 1023-1031, 1995) using rose chalcone synthase cDNA (DNA database: GenBank Accession No. AB038246) as the probe. Among the obtained chalcone synthase chromosome clones, there existed lambda CHS20 which included an approximately 6.4 kb DNA sequence upstream from the start codon of chalcone synthase. The approximately 2.9 kb DNA fragment obtained by digestion of lambda CHS20 with HindIII and EcoRV includes the chalcone synthase promoter region.

This fragment was ligated with a fragment obtained by digestion of pUC19 (Yanisch-Perron C et al., Gene 33:103-119, 1985) with HindIII and SmaI. This was designated as pCGP1116. The sequence of the chalcone synthase promoter region included therein is listed as SEQ ID NO: 21. An approximately 2.9 kb DNA fragment obtained by digestion of pCGP1116 with HindIII and KpnI was ligated with a DNA fragment obtained by digestion of pJB1 (Bodeau, Molecular and genetic regulation of Bronze-2 and other maize anthocyanin genes. Dissertation, Stanford University, USA, 1994) with HindIII and KpnI to obtain pCGP197.

Separately, an approximately 300 bp DNA fragment containing the nopaline synthase terminator, obtained by digestion of pUE5 with SacI and KpnI, was blunted and linked with pBluescriptSK—which had been digested with EcoRV and BamHI and blunted. A plasmid of those obtained in which the 5' end of the terminator was close to the SalI site of pBluescriptSK—was designated as pCGP1986.

A DNA fragment obtained by digesting pCGP1986 with XhoI, blunting the ends and further digesting with SalI was linked with a DNA fragment obtained by digesting pCGP197 with HindIII, blunting the ends and further digesting with SalI, to obtain pCGP2201.

Next, a DNA fragment obtained by digesting pCGP2201 with SalI and blunting the ends was linked with an approximately 1.7 kb DNA fragment (containing the pansy flavonoid 3',5'-hydroxylase gene) obtained by digesting pCGP1959 with BamHI and KpnI and blunting the ends. A plasmid of those obtained in which the rose chalcone synthase promoter had been inserted in a direction allowing transcription of the pansy flavonoid 3',5'-hydroxylase gene in the forward direction was designated as pCGP2203. Plasmid pCGP2203 was recovered by digestion with HindIII and SacI. The DNA fragment was cloned at the HindIII and SacI sites of pUCPP, and the resulting plasmid was designated as pSPB459. Next, plasmid pE2113 was digested with SnaBI and a BamHI linker (Takara) was inserted to obtain a plasmid designated as pUE6.

Figure 5:
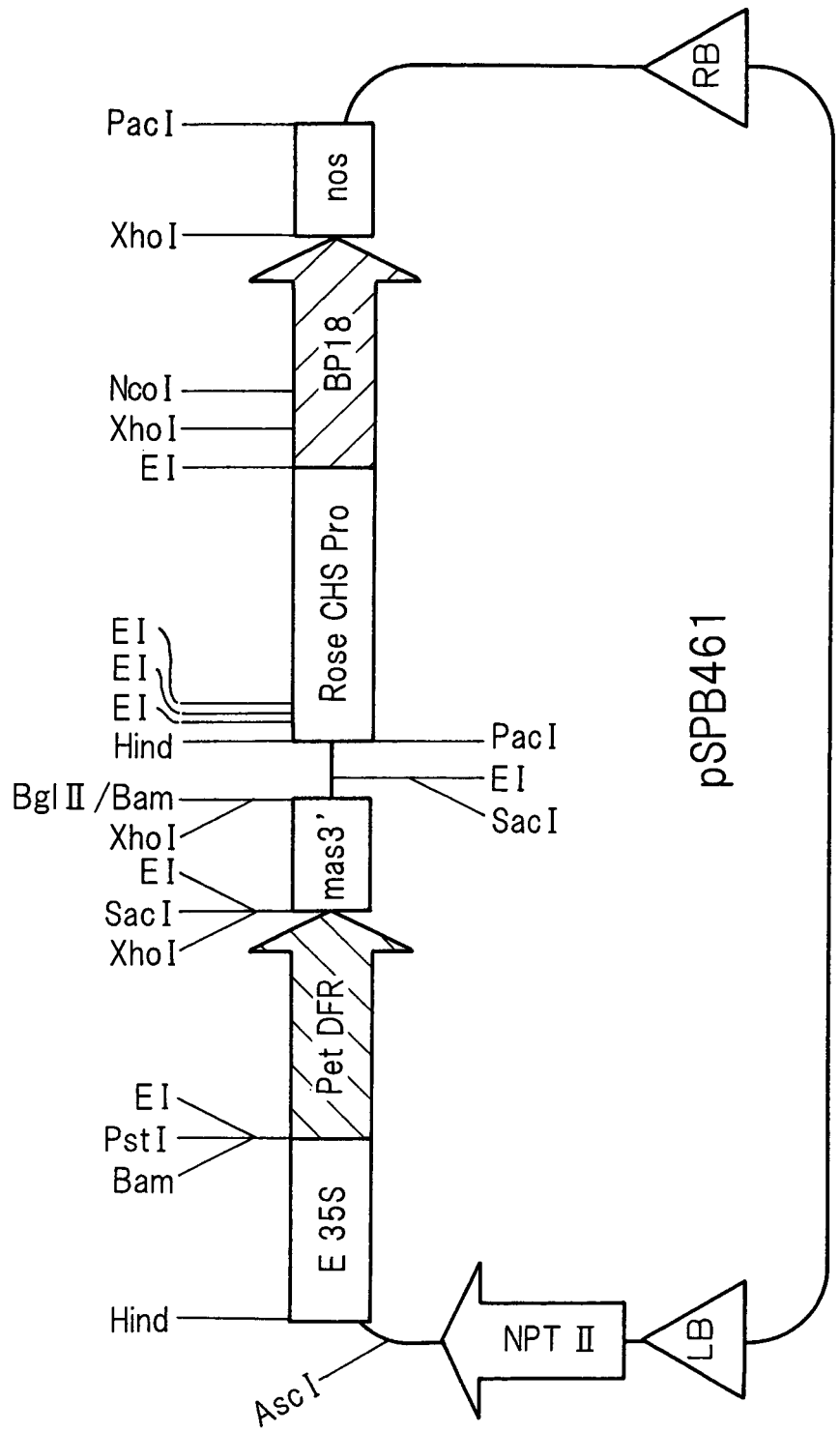
FIG. 5 shows the structure of plasmid pSPB461.

An approximately 700 bp DNA fragment obtained by digestion of pUE6 with HindIII and BamHI was linked with an approximately 2.2 kb DNA fragment obtained by digestion of pCGP1405 (WO96/36716) with BamHI and BglII and with the binary vector pBinplus (van Engelen et al., Transgenic Research 4, 288-290, 1995) digested with HindIII and BamHI, to obtain pSPB460. An approximately 5 kb DNA fragment obtained by digestion of pSPB459 with PacI was introduced into the PacI site of pSPB460 to obtain pSPB461 (FIG. 5) having the petunia DFR and pansy F3'5'H #18 genes linked in the forward direction on the binary vector. This plasmid is modified for constitutive expression of the petunia DFR gene in plants and specific transcription of the pansy F3'5'H #18 gene in flower petals. The plasmid was transferred into *Agrobacterium tumefaciens* Ag10.

Plasmid pSPB461 (FIG. 5) was transferred into the white rose "WKS36", and 229 transformants were obtained. Flower color was altered in 16 of the obtained transformants, and accumulation of delphinidin was confirmed in all 12 of the pigment-analyzed plants (Table 6). The delphinidin content was 79% at maximum (average: 58%), but the amount of pigment was very low at 0.031 mg per gram of petals and the flower color was only altered to very light pink, while no color of the Violet group, Violet-Blue group or Blue group according to the RHSCC was achieved and the target blue rose could not be obtained. This suggested that the WKS36 variety is not a variety lacking only the DFR gene.

TABLE 6

| Plant No. | Del content (%) | Del (mg/g) | Cya (mg/g) | M (mg/g) | Q (mg/g) | K (mg/g) |
|---|---|---|---|---|---|---|
| 1 | 39 | 0.002 | 0.004 | 0.000 | 0.414 | 3.744 |
| 2 | 52 | 0.006 | 0.005 | 0.000 | 0.465 | 3.363 |
| 3 | 27 | 0.002 | 0.005 | 0.000 | 0.342 | 3.703 |
| 4 | 58 | 0.014 | 0.010 | 0.000 | 0.430 | 2.780 |
| 5 | 62 | 0.008 | 0.005 | 0.498 | 0.281 | 2.189 |
| 6 | 72 | 0.002 | 0.001 | 0.000 | 0.193 | 2.391 |
| 7 | 71 | 0.010 | 0.004 | 0.000 | 0.152 | 4.021 |
| 8 | 79 | 0.031 | 0.008 | 0.403 | 0.215 | 2.660 |
| 9 | 26 | 0.004 | 0.011 | 0.000 | 0.249 | 2.331 |
| 10 | 54 | 0.007 | 0.006 | 0.000 | 0.299 | 2.085 |
| 11 | 74 | 0.017 | 0.006 | 0.145 | 0.248 | 3.505 |
| 12 | 74 | 0.013 | 0.005 | 0.000 | 0.229 | 2.005 |

Example 12

Transfer of Pansy F3'5'H Gene (#18), Petunia DFR Gene and Perilla Anthocyanin β-Glucoside Acyltransferase Gene into WKS36

A gene comprising a start codon added to the perilla hydroxycinnamoyl CoA: anthocyanin β-glucoside acyltransferase (3AT) gene was designated as pSAT208F (Yonekura-Sakakibara et al., Plant Cell Physiol. 41, 495-502, 2000). An approximately 3.9 kb DNA fragment obtained by digestion of pSPB580 (PCT/AU03/00079) with BamHI and XhoI was linked with an approximately 1.8 kb DNA fragment obtained by digestion of pSAT208F with BamHI and XhoI.

Figure 6:
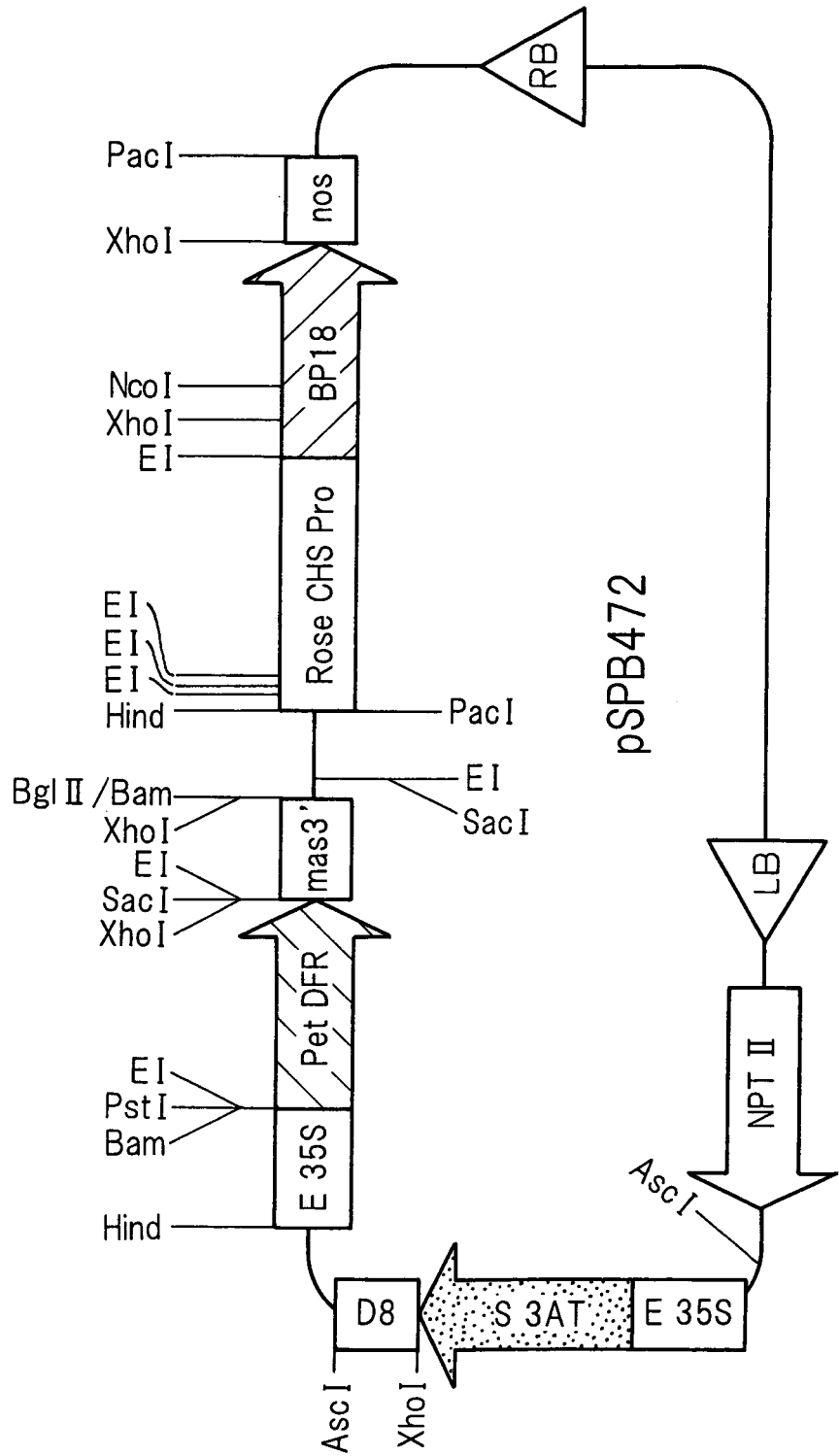
FIG. 6 shows the structure of plasmid pSPB472.

The obtained plasmid was digested with AscI, and a DNA fragment was recovered containing the E1235S promoter, the perilla 3AT gene and the petunia phospholipid transfer protein terminator. The DNA fragment was inserted into the AscI site of pSPB461 to obtain plasmid pSPB472 (FIG. 6) having the perilla 3AT, petunia DFR and pansy F3'5'H #18 gene transcription directions in the forward direction. This plasmid is modified for constitutive expression of the perilla 3AT gene and the *petunia* DFR gene in plants and specific transcription of the pansy F3'5'H #18 gene in flower petals. The plasmid was transferred into *Agrobacterium tumefaciens* Ag10.

Plasmid pSPB472 (FIG. 6) was transferred into the white rose "WKS36", and 75 transformants were obtained. Flower color was altered in four of the obtained transformants, and accumulation of delphinidin was confirmed in all three of the pigment-analyzed plants (Table 7). The delphinidin content was 67% at maximum (average: 49%), but the amount of pigment was very low at 0.011 mg per gram of petals and the flower color was only altered to very light pink, while no color of the Violet group, Violet-Blue group or Blue group according to the RHSCC was achieved and the target blue rose could not be obtained. This suggested that the WKS36 variety is not a variety lacking only the DFR gene.

TABLE 7

| Plant Plant No. | Del content (%) | Del (mg/g) | Cya (mg/g) | M (mg/g) | Q (mg/g) | K (mg/g) |
|---|---|---|---|---|---|---|
| 1 | 32 | 0.003 | 0.006 | 0.219 | 0.236 | 1.972 |
| 2 | 67 | 0.011 | 0.005 | 0.520 | 0.329 | 3.234 |
| 3 | 46 | 0.006 | 0.007 | 0.000 | 0.579 | 3.874 |

Thus, despite screening of several white roses, it was not possible to obtain a cultivar lacking only the DFR gene. In other words, it was not possible to obtain a blue rose by the method for creation of blue carnation (WO94/28140).

Example 13

Inhibition of Rose DFR Gene by Cosuppression

Plasmid pBERD1 was transferred into the pale violet rose "Lavande", and 26 transformants were obtained. However, none of the plants exhibited altered flower color, suggesting that it is difficult to inhibit the rose endogenous DFR gene by cosuppression.

Example 14

Screening for Colored Roses

Cultivars for creation of blue roses were then selected from among colored roses. After visually selecting 136 lines from colored rose cultivars with relatively blue shades, 89 of the lines were subjected to pigment analysis. The values obtained for the examined colored roses are shown in Tables 8 to 10.

TABLE 8

| Name | Cya (mg/g) | Pel (mg/g) | Peo (mg/g) | Q (mg/g) | K (mg/g) |
|---|---|---|---|---|---|
| Lavande | 0.078 | 0.000 | 0.000 | 0.451 | 0.078 |
| Madam Violet | 0.055 | 0.000 | 0.000 | 1.780 | 0.189 |
| Vol de Nuit | 0.317 | 0.003 | 0.000 | 2.661 | 0.316 |
| Blue Moon | 0.049 | 0.000 | 0.000 | 1.341 | 0.119 |
| Seiryu | 0.015 | 0.000 | 0.000 | 3.030 | 1.300 |
| WKS077 | 1.875 | 0.008 | 0.000 | 1.430 | 0.247 |
| WKS078 | 0.211 | 0.000 | 0.000 | 1.286 | 0.133 |
| WKS079 | 2.864 | 0.003 | 0.000 | 1.030 | 0.106 |
| WKS080 | 0.040 | 0.000 | 0.000 | 0.362 | 0.047 |
| WKS081 | 0.032 | 0.000 | 0.000 | 4.480 | 1.563 |
| WKS082 | 0.074 | 0.000 | 0.000 | 2.400 | 0.196 |
| WKS083 | 0.018 | 0.405 | 0.000 | 0.146 | 0.962 |
| WKS084 | 0.055 | 0.000 | 0.000 | 1.269 | 0.159 |
| WKS087 | 0.032 | 0.000 | 0.000 | 0.797 | 0.134 |
| WKS089 | 0.030 | 0.000 | 0.000 | 1.484 | 0.317 |
| WKS090 | 1.571 | 0.007 | 0.000 | 1.346 | 0.339 |
| WKS091 | 0.045 | 0.169 | 0.000 | 0.186 | 0.899 |
| WKS092 | 0.038 | 0.002 | 0.000 | 1.358 | 0.135 |
| WKS095 | 0.015 | 0.000 | 0.000 | 2.945 | 0.255 |
| WKS096 | 0.024 | 0.000 | 0.000 | 2.032 | 0.349 |
| WKS097 | 0.991 | 0.002 | 0.000 | 1.659 | 0.185 |
| WKS100 | 0.051 | 0.000 | 0.000 | 1.410 | 0.615 |
| WKS101 | 0.424 | 0.000 | 0.000 | 2.194 | 0.482 |
| WKS104 | 0.066 | 0.000 | 0.000 | 2.347 | 0.424 |
| WKS107 | 1.202 | 0.004 | 0.000 | 3.134 | 0.460 |
| WKS114 | 0.429 | 0.000 | 0.000 | 3.509 | 0.541 |
| WKS116 | 0.026 | 0.000 | 0.000 | 3.440 | 0.868 |

TABLE 8-continued

| Name | Cya (mg/g) | Pel (mg/g) | Peo (mg/g) | Q (mg/g) | K (mg/g) |
|---|---|---|---|---|---|
| WKS117 | 0.027 | 0.000 | 0.000 | 0.227 | 0.149 |
| WKS121 | 0.669 | 0.006 | 0.000 | 1.336 | 0.453 |
| WKS123 | 0.487 | 0.003 | 0.000 | 3.663 | 0.826 |

Peo: Peonidin

TABLE 9

| Name | Cya (mg/g) | Pel (mg/g) | Peo (mg/g) | Q (mg/g) | K (mg/g) |
|---|---|---|---|---|---|
| WKS124 | 0.022 | 0.045 | 0.000 | 0.192 | 2.012 |
| WKS125 | 0.187 | 0.002 | 0.000 | 0.349 | 0.089 |
| WKS126 | 0.544 | 0.002 | 0.000 | 2.226 | 0.895 |
| WKS127 | 1.609 | 0.008 | 0.006 | 2.278 | 0.528 |
| WKS128 | 1.844 | 0.003 | 0.007 | 2.576 | 0.409 |
| WKS129 | 1.645 | 0.002 | 0.006 | 0.450 | 0.160 |
| WKS130 | 1.332 | 0.008 | 0.005 | 1.599 | 0.525 |
| WKS131 | 0.582 | 0.002 | 0.001 | 2.460 | 0.567 |
| WKS132 | 1.101 | 0.006 | 0.000 | 0.298 | 0.208 |
| WKS133 | 2.773 | 0.003 | 0.000 | 1.263 | 0.230 |
| WKS133 | 3.487 | 0.011 | 0.023 | 0.414 | 0.108 |
| WKS134 | 1.084 | 0.001 | 0.002 | 2.777 | 0.413 |
| WKS135 | 0.241 | 0.007 | 0.001 | 0.803 | 0.113 |
| WKS136 | 0.637 | 0.000 | 0.003 | 1.451 | 0.062 |
| WKS137 | 1.208 | 0.014 | 0.002 | 1.034 | 1.027 |
| WKS138 | 1.955 | 0.006 | 0.000 | 3.857 | 0.855 |
| WKS139 | 0.285 | 0.003 | 0.000 | 1.363 | 0.538 |
| WKS140 | 0.075 | 0.000 | 0.000 | 0.291 | 0.097 |
| WKS141 | 0.197 | 0.000 | 0.000 | 0.358 | 0.045 |
| WKS142 | 1.906 | 0.029 | 0.106 | 1.890 | 1.860 |
| WKS143 | 1.125 | 0.027 | 0.020 | 1.596 | 1.129 |
| WKS144 | 2.685 | 0.484 | 0.000 | 0.160 | 0.184 |
| WKS145 | 0.948 | 0.006 | 0.000 | 3.086 | 1.222 |
| WKS146 | 3.108 | 0.047 | 0.000 | 0.228 | 0.398 |
| WKS147 | 0.593 | 0.003 | 0.004 | 3.619 | 0.924 |
| WKS148 | 0.059 | 0.000 | 0.000 | 3.113 | 0.466 |
| WKS149 | 1.101 | 0.013 | 0.000 | 1.481 | 1.866 |
| WKS150 | 0.498 | 0.562 | 0.000 | 0.061 | 0.156 |
| WKS151 | 0.947 | 1.073 | 0.000 | 0.038 | 0.227 |
| WKS152 | 0.303 | 1.599 | 0.000 | 0.015 | 0.464 |

Peo: Peonidin

TABLE 10

| Name | Cya (mg/g) | Pel (mg/g) | Peo (mg/g) | Q (mg/g) | K (mg/g) |
|---|---|---|---|---|---|
| WKS153 | 1.178 | 0.796 | 0.000 | 0.020 | 0.179 |
| WKS154 | 0.219 | 0.659 | 0.000 | 0.007 | 0.265 |
| WKS155 | 0.547 | 0.006 | 0.000 | 1.274 | 0.073 |
| WKS156 | 0.851 | 0.005 | 0.000 | 1.139 | 0.238 |
| WKS157 | 0.955 | 0.555 | 0.000 | 0.133 | 1.315 |
| WKS158 | 0.634 | 0.005 | 0.000 | 0.526 | 0.219 |
| WKS159 | 0.106 | 0.320 | 0.000 | 0.034 | 0.959 |
| WKS160 | 0.750 | 0.005 | 0.000 | 2.283 | 0.768 |
| WKS161 | 0.262 | 0.419 | 0.000 | 0.197 | 1.115 |
| WKS162 | 0.039 | 0.564 | 0.000 | 0.041 | 0.447 |
| WKS163 | 0.184 | 0.002 | 0.000 | 0.756 | 0.105 |
| WKS164 | 0.918 | 0.012 | 0.000 | 1.954 | 2.832 |
| WKS165 | 0.097 | 0.604 | 0.000 | 0.026 | 0.197 |
| WKS166 | 0.116 | 0.015 | 0.000 | 0.488 | 0.566 |
| WKS167 | 0.647 | 0.002 | 0.000 | 2.507 | 0.499 |
| WKS168 | 1.109 | 0.029 | 0.000 | 1.797 | 2.328 |
| WKS169 | 0.070 | 0.003 | 0.000 | 0.208 | 1.369 |
| Baby Faurax | 2.247 | 0.022 | 0.058 | 4.518 | 0.580 |
| Indigo | 0.891 | 0.006 | 0.000 | 5.781 | 3.820 |
| Intermezzo | 0.040 | 0.000 | 0.000 | 1.075 | 0.443 |
| James Veitch | 1.281 | 0.004 | 0.002 | 2.087 | 0.923 |
| Lagoon | 0.053 | 0.000 | 0.000 | 2.887 | 0.315 |
| Magenta | 0.126 | 0.000 | 0.000 | 1.062 | 0.191 |
| MRS COLVILLE | 1.666 | 0.012 | 0.000 | 3.500 | 2.940 |

TABLE 10-continued

| Name | Cya (mg/g) | Pel (mg/g) | Peo (mg/g) | Q (mg/g) | K (mg/g) |
|---|---|---|---|---|---|
| Mme. Isaac Pereire | 0.629 | 0.003 | 0.000 | 1.021 | 0.105 |
| Mme. de La Roche-Lambert | 0.869 | 0.005 | 0.000 | 4.994 | 2.794 |
| Roseraie de L'hay | 0.364 | 0.005 | 1.256 | 0.156 | 0.077 |
| Rose de Rescht | 1.348 | 0.004 | 0.000 | 4.027 | 0.842 |
| Rose du Roi a Fleurs Pourpres | 2.556 | 0.017 | 0.000 | 0.968 | 0.411 |

Peo: Peonidin

Example 15

Transfer of Pansy F3'5'H Gene (#40) and *Torenia* Anthocyanin 5-acyltransferase Gene into Lavande Modification of anthocyanins with aromatic acyl groups can stabilize the anthocyanins and produce a bluer color (for example, WO96/25500). The following experiment was conducted with the goal of producing acylated delphinidin-type anthocyanins.

RNA was obtained from *Torenia* Summer Wave flower petals, and polyA+RNA was prepared therefrom. A cDNA library was prepared from the polyA+RNA with λZAPII (Stratagene) as the vector, using a directional cDNA library preparation kit (Stratagene) according to the manufacturer's recommended protocol. The major anthocyanin of *Torenia* is modified with an aromatic acyl group at the 5-position glucose (Suzuki et al., Molecular Breeding 2000 6, 239-246), and therefore anthocyanin acyltransferase is expressed in *Torenia* petals.

Anthocyanin acyltransferase includes the conserved amino acid sequence Asp-Phe-Gly-Trp-Gly-Lys, and corresponding synthetic DNA can be used as primer to obtain the anthocyanin acyltransferase gene (WO96/25500). Specifically, 10 ng of single-stranded cDNA synthesized for construction of the *Torenia* cDNA library was used as template, and 100 ng of ATC primer (5'-GA(TC)TT(TC)GG(T)GGGGIAA-3', I: inosine) (SEQ ID NO: 17) and 100 ng of oligo dT primer (5'-TTTTTTTTTTTTTTTTCTCGAG-3') (SEQ ID NO: 18) were used as primers for PCR with Taq polymerase (Takara, Japan), under the manufacturer's recommended conditions.

The PCR was carried out in 25 cycles of reaction with one cycle consisting of 1 minute at 95° C., 1 minute at 55° C. and 1 minute at 72° C. The approximately 400 bp DNA fragment that was obtained was recovered with Gene Clean II (BIO, 101. Inc.) according to the manufacturer's recommended protocol, and was subcloned in pCR-TOPO. Determination of the nucleotide sequence revealed a sequence homologous to the gentian acyltransferase gene (Fujiwara et al., 1998, Plant J. 16 421-431). The nucleotide sequence was determined by the Dye Primer method (Applied Biosystems), using Sequencer 310 or 377 (both by Applied Biosystems).

The DNA fragment was labeled with DIG using a DIG-labeling detection kit (Japan Roche), and used for screening of a *Torenia* cDNA library by plaque hybridization according to the manufacturer's recommended protocol. Twelve of the obtained positive signal clones were randomly selected, the plasmids were recovered, and their nucleotide sequences were determined. These exhibited high homology with anthocyanin acyltransferase. The total nucleotide sequence of the cDNA in the clone designated as pTAT7 was determined. The nucleotide sequence is listed as SEQ ID NO: 7, and the corresponding amino acid sequence is listed as SEQ ID NO: 8.

After digesting pBE2113-GUS (Mitsuhara et al., Plant Cell Physiol. 37, 49-59, 1996) with SacI, the ends were blunted and an 8 bp XhoI linker (Takara) was inserted. An approximately 1.7 kb DNA fragment obtained by digesting pTAT7 with BamHI and XhoI was inserted at the BamHI and XhoI sites of this plasmid, to obtain pSPB120. After digesting pSPB120 with SnaBI and BamHI, the ends were blunted and ligation was performed to obtain pSPB120'. Separately, plasmid pCGP1961 containing pansy F3'5'H #40 cDNA was completely digested with BamHI and then partially digested with XhoI to obtain an approximately 1.8 kb DNA fragment which was recovered and ligated with pUE5H previously digested with BamHI and XhoI, to obtain a plasmid which was designated as pUEBP40.

Figure 7:
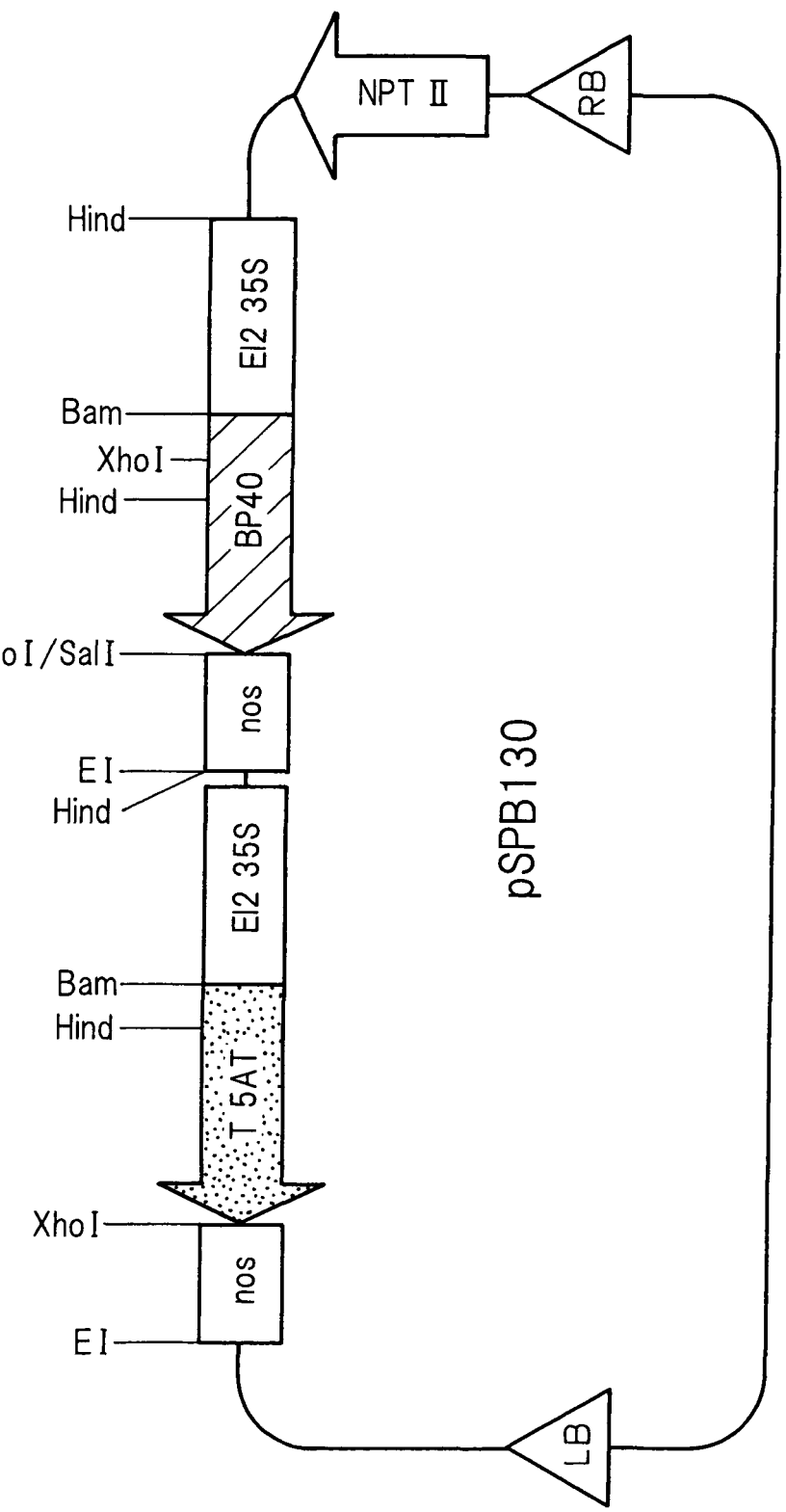
FIG. 7 shows the structure of plasmid pSPB130.

After digesting pUEBP40 with SnaBI and BamHI, the ends were blunted and ligation was performed to obtain pUEBP40'. This plasmid pUEBP40' was partially digested with HindIII to obtain an approximately 2.7 kb DNA fragment which was recovered and linked with a DNA fragment obtained by partial digestion of pSPB120' with HindIII. Of the obtained plasmids, a binary vector having the neomycin phosphotransferase gene, pansy F3'5'H #40 gene and *Torenia* 5AT gene linked in that order in the same direction from the right border sequence on the binary vector, was designated as pSPB130 (FIG. 7). This plasmid is modified for constitutive expression of the pansy F3'5'H #40 gene and the *Torenia* 5AT gene in plants and specific transcription of the genes in the flower petals. The plasmid was transferred into *Agrobacterium tumefaciens* Ag10.

Plasmid pSPB130 (FIG. 7) was transferred into the pale violet rose variety "Lavande", and 41 transformants were obtained. Accumulation of delphinidin was confirmed in 20 of the 32 pigment-analyzed plants (Tables 11 and 12). The delphinidin content was 71% at maximum (average: 36%). The flower color was altered from RHS Color Chart 186c (Greyed-Purple group) to 79d (Purple group). The proportion of acylated anthocyanins was only about 30% of the total anthocyanins. Upon spectral measurement of the acylated anthocyanins, the maximum absorption wavelength had shifted toward longer wavelength by 4 nm from delphinidin 3,5-diglucoside, but because of the low proportion among the total anthocyanins, no clear effect was achieved for the flower color.

TABLE 11

| Plant No. | Acylation (%) | Del content (%) | Del (mg/g) | Cya (mg/g) | M (mg/g) | Q (mg/g) | K (mg/g) |
|---|---|---|---|---|---|---|---|
| 1 | 0 | 9 | 0.005 | 0.050 | na | na | na |
| 2 | 0 | 11 | 0.009 | 0.069 | na | na | na |
| 3 | 0 | 10 | 0.010 | 0.087 | na | na | na |
| 4 | 0 | 22 | 0.028 | 0.102 | na | na | na |
| 5 | 5 | 51 | 0.073 | 0.069 | na | na | na |
| 6 | 4 | 57 | 0.093 | 0.069 | na | na | na |
| 7 | 5 | 48 | 0.039 | 0.042 | na | na | na |
| 8 | 13 | 0 | 0.000 | 0.065 | na | na | na |
| 9 | 17 | 9 | 0.006 | 0.062 | na | na | na |
| 10 | 26 | 0 | 0.000 | 0.104 | na | na | na |
| 11 | 17 | 67 | 0.074 | 0.036 | na | na | na |
| 12 | 0 | 0 | 0.000 | 0.131 | na | na | na |
| 13 | 0 | 0 | 0.000 | 0.083 | na | na | na |
| 14 | 6 | 48 | 0.084 | 0.092 | na | na | na |
| 15 | 0 | 20 | 0.020 | 0.081 | na | na | na |
| 16 | 42 | 13 | 0.020 | 0.131 | 0.000 | 0.637 | 0.020 |
| 17 | 32 | 36 | 0.032 | 0.058 | na | na | na |

TABLE 11-continued

| Plant No. | Acylation (%) | Del content (%) | Del (mg/g) | Cya (mg/g) | M (mg/g) | Q (mg/g) | K (mg/g) |
|---|---|---|---|---|---|---|---|
| 18 | 7 | 0 | 0.000 | 0.146 | na | na | na |
| 19 | 0 | 0 | 0.000 | 0.069 | na | na | na |
| 20 | 0 | 0 | 0.000 | 0.142 | na | na | na |
| 21 | 0 | 0 | 0.000 | 0.080 | na | na | na | na: no analysis/measurement

TABLE 12

| Plant No. | Acylation (%) | Del content (%) | Del (mg/g) | Cya (mg/g) | M (mg/g) | Q (mg/g) | K (mg/g) |
|---|---|---|---|---|---|---|---|
| 22 | 0 | 0 | 0.000 | 0.069 | na | na | na |
| 23 | 0 | 0 | 0.000 | 0.057 | na | na | na |
| 24 | 18 | 4 | 0.006 | 0.149 | na | na | na |
| 25 | 17 | 4 | 0.008 | 0.208 | na | na | na |
| 26 | 0 | 0 | 0.000 | 0.188 | na | na | na |
| 27 | 0 | 0 | 0.000 | 0.078 | na | na | na |
| 28 | 17 | 67 | 0.090 | 0.044 | na | na | na |
| 29 | 17 | 71 | 0.057 | 0.024 | na | na | na |
| 30 | 16 | 40 | 0.040 | 0.059 | na | na | na |
| 31 | 21 | 70 | 0.082 | 0.036 | 0.305 | 0.062 | 0.008 |
| 32 | 18 | 62 | 0.066 | 0.040 | na | na | na | na: no analysis/measurement

Example 16

Transfer of Pansy F3'5'H Gene (#40) and *Torenia anthocyanin* 5-acyltransferase gene into WKS100

Plasmid pSPB130 (FIG. 7) was transferred into the pale violet rose variety "WKS100", and 146 transformants were obtained. Accumulation of delphinidin was confirmed in 56 of the 63 pigment-analyzed plants (Tables 13-15). The delphinidin content was 95% at maximum (average: 44%). The flower color was altered from RHS Color Chart 56d (Red group) to 186d (Greyed-Purple group). However, no color of the Violet group, Violet-Blue group or Blue group according to the RHSCC was achieved and the target blue rose could not be obtained.

TABLE 13

| Plant No. | Acylation (%) | Del content (%) | Del (mg/g) | Cya (mg/g) | Pel (mg/g) | M (mg/g) | Q (mg/g) | K (mg/g) |
|---|---|---|---|---|---|---|---|---|
| 1 | 20 | 75 | 0.036 | 0.012 | 0.000 | 2.944 | 0.974 | 0.322 |
| 2 | 16 | 51 | 0.027 | 0.027 | 0.000 | 1.685 | 1.734 | 0.512 |
| 3 | 13 | 50 | 0.024 | 0.024 | 0.000 | 0.000 | 1.382 | 1.912 |
| 4 | 23 | 50 | 0.037 | 0.037 | 0.000 | na | na | na |
| 5 | 9 | 25 | 0.013 | 0.033 | 0.005 | na | na | na |
| 6 | 10 | 26 | 0.034 | 0.097 | 0.000 | na | na | na |
| 7 | 13 | 65 | 0.053 | 0.028 | 0.000 | 1.936 | 1.184 | 0.760 |
| 8 | 13 | 65 | 0.044 | 0.024 | 0.000 | 1.622 | 1.065 | 0.562 |
| 9 | 14 | 62 | 0.033 | 0.021 | 0.000 | 2.096 | 1.444 | 0.710 |
| 10 | 14 | 95 | 0.137 | 0.008 | 0.000 | 0.000 | 0.156 | 1.097 |
| 11 | 10 | 62 | 0.036 | 0.022 | 0.000 | 2.025 | 1.194 | 0.799 |
| 12 | 5 | 59 | 0.054 | 0.038 | 0.000 | 2.194 | 1.289 | 0.783 |
| 13 | 9 | 43 | 0.033 | 0.044 | 0.000 | 2.542 | 1.803 | 0.734 |
| 14 | 9 | 50 | 0.030 | 0.031 | 0.000 | 0.020 | 1.971 | 0.741 |
| 15 | 1 | 70 | 0.066 | 0.028 | 0.000 | 1.652 | 1.659 | 0.867 |
| 16 | 0 | 20 | 0.008 | 0.023 | 0.008 | 0.308 | 2.632 | 1.463 |
| 17 | 1 | 63 | 0.068 | 0.040 | 0.000 | 2.037 | 2.128 | 1.554 |
| 18 | 21 | 51 | 0.037 | 0.035 | 0.000 | 2.659 | 1.936 | 1.002 |
| 19 | 0 | 0 | 0.000 | 0.095 | 0.000 | na | na | na |
| 20 | 0 | 0 | 0.000 | 0.037 | 0.000 | na | na | na |
| 21 | 0 | 23 | 0.026 | 0.086 | 0.003 | 0.182 | 4.554 | 3.083 |
| 22 | 4 | 71 | 0.110 | 0.044 | 0.000 | 3.265 | 1.643 | 1.341 |
| 23 | 12 | 65 | 0.051 | 0.025 | 0.002 | 1.356 | 0.888 | 0.387 |
| 24 | 6 | 58 | 0.038 | 0.027 | 0.000 | 2.374 | 2.016 | 0.809 |
| 25 | 5 | 52 | 0.044 | 0.040 | 0.000 | 2.651 | 2.546 | 1.108 | na: no analysis/measurement

TABLE 14

| Plant No. | Acylation (%) | Del content (%) | Del (mg/g) | Cya (mg/g) | Pel (mg/g) | M (mg/g) | Q (mg/g) | K (mg/g) |
|---|---|---|---|---|---|---|---|---|
| 26 | 6 | 64 | 0.033 | 0.019 | 0.000 | 2.707 | 1.546 | 0.605 |
| 27 | 16 | 0 | 0.000 | 0.041 | 0.000 | na | na | na |
| 28 | 16 | 13 | 0.007 | 0.050 | 0.000 | 0.249 | 3.359 | 1.459 |
| 29 | 12 | 7 | 0.007 | 0.095 | 0.000 | na | na | na |
| 30 | 15 | 9 | 0.007 | 0.069 | 0.000 | na | na | na |
| 31 | 15 | 8 | 0.007 | 0.081 | 0.000 | na | na | na |
| 32 | 7 | 7 | 0.007 | 0.094 | 0.000 | na | na | na |
| 33 | 13 | 10 | 0.006 | 0.055 | 0.000 | na | na | na |
| 34 | 14 | 46 | 0.078 | 0.090 | 0.002 | na | na | na |

TABLE 14-continued

| Plant No. | Acylation (%) | Del content (%) | Del (mg/g) | Cya (mg/g) | Pel (mg/g) | M (mg/g) | Q (mg/g) | K (mg/g) |
|---|---|---|---|---|---|---|---|---|
| 35 | 7 | 8 | 0.007 | 0.078 | 0.000 | na | na | na |
| 36 | 3 | 48 | 0.045 | 0.039 | 0.010 | 3.050 | 2.304 | 1.326 |
| 37 | 2 | 39 | 0.029 | 0.046 | 0.000 | na | na | na |
| 38 | 1 | 55 | 0.073 | 0.059 | 0.000 | 1.608 | 2.138 | 1.015 |
| 39 | 1 | 33 | 0.030 | 0.063 | 0.000 | na | na | na |
| 40 | 2 | 59 | 0.050 | 0.035 | 0.000 | 3.651 | 2.727 | 1.076 |
| 41 | 17 | 15 | 0.011 | 0.061 | 0.000 | na | na | na |
| 42 | 0 | 0 | 0.000 | 0.048 | 0.002 | na | na | na |
| 43 | 3 | 17 | 0.009 | 0.046 | 0.000 | na | na | na |
| 44 | 40 | 32 | 0.027 | 0.058 | 0.000 | na | na | na |
| 45 | 2 | 0 | 0.000 | 0.031 | 0.000 | na | na | na |
| 46 | 2 | 0 | 0.000 | 0.038 | 0.000 | na | na | na |
| 47 | 1 | 8 | 0.004 | 0.048 | 0.000 | na | na | na |
| 48 | 19 | 57 | 0.046 | 0.034 | 0.000 | 2.626 | 2.165 | 0.900 |
| 49 | 10 | 59 | 0.047 | 0.032 | 0.000 | 1.737 | 1.901 | 1.054 |
| 50 | 2 | 70 | 0.057 | 0.024 | 0.000 | 1.545 | 0.880 | 0.694 | na: no analysis/measurement

TABLE 15

| Plant No. | Acylation (%) | Del content (%) | Del (mg/g) | Cya (mg/g) | Pel (mg/g) | M (mg/g) | Q (mg/g) | K (mg/g) |
|---|---|---|---|---|---|---|---|---|
| 51 | 4 | 10 | 0.006 | 0.056 | 0.000 | na | na | na |
| 52 | 16 | 12 | 0.006 | 0.039 | 0.002 | na | na | na |
| 53 | 34 | 84 | 0.156 | 0.030 | 0.000 | 5.100 | 1.056 | 0.511 |
| 54 | 32 | 89 | 0.131 | 0.017 | 0.000 | 3.907 | 0.803 | 0.431 |
| 55 | 29 | 89 | 0.098 | 0.013 | 0.000 | 3.687 | 0.453 | 0.226 |
| 56 | 21 | 83 | 0.083 | 0.017 | 0.000 | 2.679 | 0.817 | 0.431 |
| 57 | 14 | 8 | 0.007 | 0.082 | 0.000 | na | na | na |
| 58 | 9 | 44 | 0.034 | 0.041 | 0.002 | 2.258 | 2.054 | 0.672 |
| 59 | 7 | 51 | 0.040 | 0.038 | 0.000 | 2.246 | 2.151 | 0.765 |
| 60 | 0 | 7 | 0.008 | 0.111 | 0.000 | na | na | na |
| 61 | 1 | 48 | 0.069 | 0.073 | 0.000 | 1.558 | 1.730 | 0.565 |
| 62 | 13 | 0 | 0.000 | 0.036 | 0.000 | na | na | na |
| 63 | 16 | 14 | 0.005 | 0.029 | 0.000 | na | na | na | na: no analysis/measurement

Example 17

Transfer of Pansy F3'5'H Gene (#40) and *Torenia* Anthocyanin 5-Acyltransferase Gene into WKS116

Plasmid pSPB130 (FIG. 7) was transferred into the pale violet rose variety "WKS116", and 282 transformants were obtained. Accumulation of delphinidin was confirmed in 33 of the 36 pigment-analyzed plants (Tables 16 and 17). The delphinidin content was 80% at maximum (average: 73%). The flower color was altered from RHS Color Chart 196d (Greyed-Green group) to 186d (Greyed-Purple group). However, no color of the Violet group, Violet-Blue group or Blue group according to the RHSCC was achieved and the target blue rose could not be obtained.

TABLE 16

| Plant No. | Acylation (%) | Del content (%) | Del (mg/g) | Cya (mg/g) | M (mg/g) | Q (mg/g) | K (mg/g) |
|---|---|---|---|---|---|---|---|
| 1 | 1.8 | 78 | 0.015 | 0.004 | 0.746 | 0.753 | 0.507 |
| 2 | 12.7 | 78 | 0.097 | 0.028 | 1.826 | 2.352 | 1.572 |
| 3 | 5.9 | 78 | 0.030 | 0.009 | 1.000 | 1.452 | 0.934 |
| 4 | 0.0 | 76 | 0.030 | 0.010 | 0.813 | 0.990 | 0.480 |
| 5 | 2.6 | 72 | 0.038 | 0.015 | 1.279 | 1.835 | 0.832 |
| 6 | 0.0 | 72 | 0.019 | 0.007 | 0.839 | 0.983 | 0.642 |
| 7 | 3.1 | 75 | 0.033 | 0.011 | 1.131 | 1.476 | 0.877 |
| 8 | 1.9 | 75 | 0.028 | 0.009 | 0.761 | 0.977 | 0.466 |
| 9 | 2.6 | 76 | 0.034 | 0.011 | na | na | na |
| 10 | 2.7 | 73 | 0.031 | 0.011 | na | na | na |
| 11 | 4.4 | 77 | 0.033 | 0.010 | 1.001 | 1.003 | 0.618 |
| 12 | 7.0 | 74 | 0.035 | 0.012 | 0.849 | 0.945 | 0.577 |
| 13 | 9.3 | 74 | 0.025 | 0.009 | na | na | na |
| 14 | 3.2 | 80 | 0.044 | 0.011 | 1.045 | 0.959 | 0.545 |
| 15 | 4.5 | 75 | 0.031 | 0.010 | 1.115 | 1.256 | 0.729 |
| 16 | 10.5 | 71 | 0.028 | 0.012 | 1.055 | 1.155 | 0.670 |
| 17 | 1.7 | 51 | 0.016 | 0.016 | 0.330 | 1.537 | 1.052 |
| 18 | 10.5 | 77 | 0.112 | 0.033 | 2.008 | 2.976 | 2.216 |
| 19 | 0.0 | 0 | 0.000 | 0.010 | na | na | na |
| 20 | 0.0 | 30 | 0.007 | 0.015 | na | na | na |
| 21 | na | 56 | 0.013 | 0.010 | 0.197 | 1.960 | 1.463 |

TABLE 16-continued

| Plant No. | Acylation (%) | Del content (%) | Del (mg/g) | Cya (mg/g) | M (mg/g) | Q (mg/g) | K (mg/g) |
|---|---|---|---|---|---|---|---|
| 22 | 4.4 | 47 | 0.006 | 0.007 | na | na | na |
| 23 | 3.6 | 77 | 0.026 | 0.008 | na | na | na | na: no analysis/measurement

TABLE 17

| Plant No. | Acylation (%) | Del content (%) | Del (mg/g) | Cya (mg/g) | M (mg/g) | Q (mg/g) | K (mg/g) |
|---|---|---|---|---|---|---|---|
| 24 | 7.2 | 82 | 0.028 | 0.006 | 1.295 | 1.272 | 0.805 |
| 25 | 3.5 | 83 | 0.035 | 0.007 | na | na | na |
| 26 | 17.4 | 26 | 0.009 | 0.025 | na | na | na |
| 27 | 39.3 | 91 | 0.101 | 0.010 | 3.499 | 0.563 | 0.178 |
| 28 | 28.2 | 85 | 0.047 | 0.005 | na | na | na |
| 29 | 0.0 | 0 | 0.000 | 0.025 | na | na | na |
| 30 | 10.4 | 89 | 0.092 | 0.012 | na | na | na |
| 31 | 1.9 | 0 | 0.000 | 0.036 | na | na | na |
| 32 | 5.8 | 76 | 0.027 | 0.009 | na | na | na |
| 33 | 16.8 | 88 | 0.066 | 0.009 | na | na | na |
| 34 | 10.5 | 87 | 0.103 | 0.015 | na | na | na |
| 35 | 13.7 | 38 | 0.021 | 0.034 | na | na | na |
| 36 | 18.3 | 95 | 0.051 | 0.003 | na | na | na | na: no analysis/measurement

Example 18

Transfer of Pansy F3'5'H Gene (#40) and *Torenia* Anthocyanin 5-Acyltransferase Gene into WKS124

Plasmid pSPB130 (FIG. 7) was transferred into the pale orange rose variety "WKS124", and 0.50 transformants were obtained. Accumulation of delphinidin was confirmed in 13 of the 15 pigment-analyzed plants (Table 18). The delphinidin content was 95% at maximum (average: 82%). The flower color was altered from RHS Color Chart 52d (Red group) to 71c (Red-Purple group). However, no color of the Violet group, Violet-Blue group or Blue group according to the RHSCC was achieved and the target blue rose could not be obtained.

Example 19

Transfer of Pansy F3'5'H Gene (#40) and *Torenia* Anthocyanin 5-Acyltransferase Gene into WKS132

Plasmid pSPB130 (FIG. 7) was transferred into the bright red rose variety "WKS132", and 24 transformants were obtained. Accumulation of delphinidin was confirmed in 6 of the 7 pigment-analyzed plants (Table 19). The delphinidin content was 43% at maximum (average: 12%). The flower color was altered from RHS Color Chart 57a (Red-Purple group) to 66a (Red-Purple group). However, no color of the Violet group, Violet-Blue group or Blue group according to the RHSCC was achieved and the target blue rose could not be obtained.

TABLE 19

| Plant No. | Acylation (%) | Del content (%) | Del (mg/g) | Cya (mg/g) | Pel (mg/g) |
|---|---|---|---|---|---|
| 1 | 1.8 | 0.4 | 0.008 | 1.872 | 0.009 |
| 2 | 1.0 | 0.0 | 0.000 | 1.409 | 0.010 |
| 3 | 21.3 | 11.4 | 0.237 | 1.841 | 0.007 |
| 4 | 6.8 | 42.5 | 0.461 | 0.619 | 0.006 |
| 5 | 7.6 | 9.5 | 0.204 | 1.936 | 0.011 |
| 6 | na | 1.3 | 0.016 | 1.227 | 0.007 |
| 7 | 23.7 | 5.4 | 0.081 | 1.407 | 0.005 |

Example 20

Transfer of Pansy F3'5'H gene (#40) and *Torenia* Anthocyanin 5-Acyltransferase Gene into WKS133

Plasmid pSPB130 (FIG. 7) was transferred into the dark red-violet rose variety "WKS133", and 16 transformants were obtained. Accumulation of delphinidin was confirmed in all eight of the pigment-analyzed plants (Table 20). The delphinidin content was 34% at maximum (average: 11%). The flower color was altered from RHS Color Chart 53a (Red group) to 61a (Red-Purple group). However, no color of the Violet group, Violet-Blue group or Blue group according to the RHSCC was achieved and the target blue rose could not be obtained.

TABLE 18

| Plant No. | Acylation (%) | Del content (%) | Del (mg/g) | Cya (mg/g) | Pel (mg/g) | M (mg/g) | Q (mg/g) | K (mg/g) |
|---|---|---|---|---|---|---|---|---|
| 1 | 0.6 | 0 | 0.000 | 0.013 | 0.069 | na | na | na |
| 2 | 35.5 | 75 | 0.256 | 0.051 | 0.034 | 0.066 | 0.093 | 1.190 |
| 3 | 43.0 | 78 | 0.385 | 0.068 | 0.041 | 0.039 | 0.046 | 1.197 |
| 4 | 44.2 | 85 | 0.811 | 0.120 | 0.028 | 0.106 | 0.094 | 1.021 |
| 5 | na | 86 | 0.907 | 0.123 | 0.024 | 0.219 | 0.066 | 0.852 |
| 6 | 4.6 | 0 | 0.000 | 0.023 | 0.075 | na | na | na |
| 7 | 7.9 | 90 | 1.498 | 0.169 | 0.008 | 0.905 | 0.143 | 0.679 |
| 8 | 8.4 | 90 | 1.403 | 0.146 | 0.008 | 0.971 | 0.145 | 0.827 |
| 9 | 26.7 | 88 | 0.521 | 0.066 | 0.003 | 0.623 | 0.108 | 0.853 |
| 10 | 21.9 | 89 | 0.504 | 0.058 | 0.003 | 0.636 | 0.098 | 0.727 |
| 11 | 26.0 | 85 | 0.928 | 0.145 | 0.019 | 0.424 | 0.152 | 0.455 |
| 12 | 3.8 | 95 | 1.017 | 0.058 | 0.000 | 1.161 | 0.140 | 0.262 |
| 13 | 11.6 | 84 | 0.939 | 0.156 | 0.025 | 0.748 | 0.128 | 0.262 |
| 14 | 38.5 | 69 | 0.166 | 0.071 | 0.007 | 0.000 | 0.059 | 0.776 |
| 15 | 27.1 | 55 | 0.137 | 0.040 | 0.074 | 0.000 | 0.021 | 2.330 | na: no analysis/measurement

TABLE 20

| Plant No. | Acylation (%) | Del content (%) | Del (mg/g) | Cya (mg/g) | Pel (mg/g) | Peo (mg/g) | M (mg/g) | Q (mg/g) | K (mg/g) |
|---|---|---|---|---|---|---|---|---|---|
| 1 | 10.3 | 23.7 | 1.322 | 4.253 | 0.009 | 0.004 | 0.691 | 0.792 | 0.133 |
| 2 | 11.8 | 33.8 | 1.192 | 2.324 | 0.005 | 0.003 | 0.621 | 0.422 | 0.093 |
| 3 | 6.1 | 12.9 | 0.009 | 0.060 | 0.000 | 0.000 | 0.102 | 0.500 | 0.048 |
| 4 | 3.8 | 9.1 | 0.363 | 3.627 | 0.005 | 0.008 | na | na | na |
| 5 | 15.8 | 2.0 | 0.078 | 3.774 | 0.009 | 0.000 | 0.045 | 0.939 | 0.472 |
| 6 | 11.5 | 2.7 | 0.135 | 4.771 | 0.011 | 0.005 | 0.046 | 0.576 | 0.034 |
| 7 | 13.3 | 3.0 | 0.180 | 5.800 | 0.009 | 0.009 | 0.100 | 0.937 | 0.179 |
| 8 | 12.2 | 3.5 | 0.161 | 4.470 | 0.009 | 0.009 | 0.068 | 0.738 | 0.148 | na: no analysis/measurement

Example 21

Transfer of Pansy F3'5'H Gene (#40) and *Torenia* Anthocyanin 5-Acyltransferase Gene into WKS137

Plasmid pSPB130 (FIG. 7) was transferred into the dark red-violet rose variety "WKS137", and 20 transformants were obtained. Accumulation of delphinidin was confirmed in all 17 of the pigment-analyzed plants (Table 21). The delphinidin content was 1.3% at maximum (average: 0.4%). No alteration in flower color was observed from RHS Color Chart 61b (Red-Purple group).

TABLE 21

| Plant No. | Acylation (%) | Del content (%) | Del (mg/g) | Cya (mg/g) | Pel (mg/g) | Peo (mg/g) | M (mg/g) | Q (mg/g) | K (mg/g) |
|---|---|---|---|---|---|---|---|---|---|
| 1 | 0.5 | 0.3 | 0.008 | 2.821 | 0.037 | 0.000 | na | na | na |
| 2 | 0.8 | 0.3 | 0.010 | 3.384 | 0.051 | 0.000 | na | na | na |
| 3 | 0.4 | 0.3 | 0.005 | 1.982 | 0.014 | 0.000 | na | na | na |
| 4 | 0.6 | 0.2 | 0.008 | 3.344 | 0.057 | 0.000 | na | na | na |
| 5 | 0.7 | 0.4 | 0.011 | 3.145 | 0.035 | 0.000 | na | na | na |
| 6 | 0.7 | 1.3 | 0.025 | 2.919 | 0.040 | 0.003 | na | na | na |
| 7 | 0.4 | 0.3 | 0.008 | 2.820 | 0.045 | 0.000 | na | na | na |
| 8 | 0.5 | 0.4 | 0.010 | 2.467 | 0.042 | 0.000 | na | na | na |
| 9 | 0.7 | 0.2 | 0.010 | 3.836 | 0.024 | 0.000 | na | na | na |
| 10 | 0.1 | 0.5 | 0.008 | 1.743 | 0.016 | 0.000 | na | na | na |
| 11 | 0.7 | 0.4 | 0.011 | 2.593 | 0.027 | 0.003 | na | na | na |
| 12 | 0.6 | 0.3 | 0.007 | 2.393 | 0.022 | 0.000 | 0.048 | 3.026 | 2.812 |
| 13 | 1.4 | 0.2 | 0.009 | 3.756 | 0.065 | 0.000 | na | na | na |
| 14 | 0.7 | 0.4 | 0.008 | 2.149 | 0.024 | 0.001 | na | na | na |
| 15 | 0.8 | 0.5 | 0.007 | 2.281 | 0.041 | 0.000 | na | na | na |
| 16 | 0.5 | 0.5 | 0.007 | 1.314 | 0.014 | 0.000 | na | na | na |
| 17 | 1.0 | 0.2 | 0.007 | 2.892 | 0.051 | 0.000 | na | na | na | na: no analysis/measurement

Example 22

Transfer of Pansy F3'5'H Gene (#40) and *Torenia* Anthocyanin 5-acyltransferase gene into WKS140

Plasmid pSPB130 (FIG. 7) was transferred into the pale violet rose variety "WKS140", and 197 transformants were obtained. Accumulation of delphinidin was confirmed in 37 of the 45 pigment-analyzed plants (Tables 22 and 23). The delphinidin content was 94% at maximum (average: 47%). The flower color was altered from RHS Color Chart 186d (Greyed-Purple group) to 79d (Purple group). However, no color of the Violet group, Violet-Blue group or Blue group according to the RHSCC was achieved and the target blue rose could not be obtained.

TABLE 22

| Plant No. | Acylation (%) | Del content (%) | Del (mg/g) | Cya (mg/g) | M (mg/g) | Q (mg/g) | K (mg/g) |
|---|---|---|---|---|---|---|---|
| 1 | 3.5 | 0.0 | 0.000 | 0.090 | na | na | na |
| 2 | 2.5 | 0.0 | 0.000 | 0.093 | 0.096 | 2.429 | 0.246 |
| 3 | 5.5 | 63.5 | 0.061 | 0.035 | 0.688 | 1.090 | 0.106 |
| 4 | 13.2 | 17.7 | 0.013 | 0.059 | na | na | na |
| 5 | 5.4 | 11.6 | 0.017 | 0.129 | na | na | na |
| 6 | 3.6 | 12.3 | 0.011 | 0.078 | na | na | na |
| 7 | 13.6 | 11.7 | 0.009 | 0.069 | na | na | na |
| 8 | 4.1 | 22.3 | 0.012 | 0.041 | 0.057 | 1.950 | 0.492 |

TABLE 22-continued

| Plant No. | Acylation (%) | Del content (%) | Del (mg/g) | Cya (mg/g) | M (mg/g) | Q (mg/g) | K (mg/g) |
|---|---|---|---|---|---|---|---|
| 9 | 3.3 | 0.0 | 0.000 | 0.071 | na | na | na |
| 10 | 2.6 | 18.6 | 0.017 | 0.076 | na | na | na |
| 11 | 4.2 | 18.6 | 0.012 | 0.052 | 0.130 | 3.101 | 1.172 |
| 12 | 6.5 | 25.0 | 0.026 | 0.079 | 0.251 | 2.300 | 0.592 |
| 13 | 1.3 | 0.0 | 0.000 | 0.062 | 0.000 | 2.200 | 0.552 |
| 14 | 22.7 | 85.4 | 0.261 | 0.045 | 1.649 | 0.943 | 0.126 |
| 15 | 20.9 | 57.4 | 0.093 | 0.069 | 0.481 | 1.418 | 0.182 |
| 16 | 16.4 | 39.9 | 0.052 | 0.078 | na | na | na |
| 17 | 15.2 | 50.8 | 0.074 | 0.072 | na | na | na |
| 18 | 6.1 | 22.6 | 0.036 | 0.111 | 0.148 | 2.152 | 0.279 |

TABLE 22-continued

| Plant No. | Acylation (%) | Del content (%) | Del (mg/g) | Cya (mg/g) | M (mg/g) | Q (mg/g) | K (mg/g) |
|---|---|---|---|---|---|---|---|
| 19 | 2.7 | 0.0 | 0.000 | 0.033 | na | na | na |
| 20 | 9.1 | 52.6 | 0.041 | 0.037 | na | na | na |
| 21 | 4.4 | 46.2 | 0.075 | 0.087 | na | na | na |
| 22 | 8.5 | 34.7 | 0.040 | 0.075 | 0.195 | 1.847 | 0.394 |
| 23 | 11.0 | 30.9 | 0.018 | 0.040 | 0.155 | 1.106 | 0.142 |
| 24 | 13.4 | 46.8 | 0.056 | 0.063 | na | na | na |
| 25 | 2.8 | 5.1 | 0.006 | 0.107 | na | na | na | na: no analysis/measurement

TABLE 23

| Plant No. | Acylation (%) | Del content (%) | Del (mg/g) | Cya (mg/g) | M (mg/g) | Q (mg/g) | K (mg/g) |
|---|---|---|---|---|---|---|---|
| 26 | 4.1 | 6.8 | 0.007 | 0.098 | na | na | na |
| 27 | 31.4 | 93.4 | 0.252 | 0.018 | 1.434 | 0.361 | 0.052 |
| 28 | 13.4 | 86.7 | 0.101 | 0.016 | 1.237 | 1.740 | 0.499 |

TABLE 23-continued

| Plant No. | Acylation (%) | Del content (%) | Del (mg/g) | Cya (mg/g) | M (mg/g) | Q (mg/g) | K (mg/g) |
|---|---|---|---|---|---|---|---|
| 29 | 32.3 | 94.2 | 0.200 | 0.012 | 0.862 | 0.131 | 0.029 |
| 30 | 13.0 | 89.7 | 0.176 | 0.020 | 0.553 | 0.289 | 0.026 |
| 31 | 12.3 | 87.1 | 0.150 | 0.022 | 1.007 | 0.674 | 0.135 |
| 32 | 6.7 | 9.9 | 0.009 | 0.086 | na | na | na |
| 33 | 11.5 | 67.4 | 0.108 | 0.052 | na | na | na |
| 34 | 5.0 | 11.2 | 0.014 | 0.110 | 0.074 | 2.588 | 0.659 |
| 35 | 12.5 | 79.7 | 0.088 | 0.022 | 1.192 | 1.185 | 0.574 |
| 36 | 15.0 | 83.4 | 0.065 | 0.013 | 1.478 | 1.147 | 0.570 |
| 37 | 1.8 | 0.0 | 0.000 | 0.068 | na | na | na |
| 38 | 1.3 | 44.3 | 0.105 | 0.132 | 0.582 | 3.259 | 1.232 |
| 39 | 2.5 | 73.6 | 0.114 | 0.041 | na | na | na |
| 40 | 14.0 | 85.3 | 0.165 | 0.028 | 1.881 | 1.035 | 0.180 |
| 41 | 0.5 | 4.3 | 0.006 | 0.144 | na | na | na |
| 42 | 9.9 | 53.3 | 0.040 | 0.035 | 0.373 | 1.038 | 0.164 |
| 43 | 33.5 | 87.4 | 0.275 | 0.040 | 1.851 | 0.701 | 0.148 |
| 44 | 1.3 | 0.0 | 0.000 | 0.073 | na | na | na |
| 45 | 1.5 | 0.0 | 0.000 | 0.062 | na | na | na | na: no analysis/measurement

Example 23

Transfer of Pansy F3'5'H Gene (#40) and *Torenia* Anthocyanin 5-Acyltransferase Gene into WKS77

Plasmid pSPB130 (FIG. 7) was transferred into the dark red-purple rose variety "WKS77", and 35 transformants were obtained. Accumulation of delphinidin was confirmed in all 17 of the pigment-analyzed plants (Table 24). The delphinidin content was 57% at maximum (average: 33%). The flower color was altered from RHS Color Chart 57a (Red-Purple group) to 71a (Red-Purple group). However, no color of the Violet group, Violet-Blue group or Blue group according to the RHSCC was achieved and the target blue rose could not be obtained.

TABLE 24

| Plant No. | Acylation (%) | Del content (%) | Del (mg/g) | Cya (mg/g) | Pel (mg/g) | M (mg/g) | Q (mg/g) | K (mg/g) |
|---|---|---|---|---|---|---|---|---|
| 1 | 6.2 | 42.5 | 1.153 | 1.552 | 0.008 | 0.484 | 0.679 | 0.196 |
| 2 | 7.6 | 38.6 | 0.618 | 0.979 | 0.005 | 0.267 | 0.465 | 0.094 |
| 3 | 3.9 | 40.4 | 0.706 | 1.030 | 0.011 | 1.266 | 1.768 | 0.722 |
| 4 | 2.0 | 46.9 | 0.372 | 0.417 | 0.004 | 0.363 | 0.608 | 0.276 |
| 5 | 5.4 | 40.6 | 0.540 | 0.784 | 0.005 | 1.077 | 1.809 | 0.645 |
| 6 | 2.0 | 44.7 | 1.078 | 1.325 | 0.009 | 0.516 | 1.034 | 0.382 |
| 7 | 2.1 | 46.5 | 0.398 | 0.453 | 0.005 | 0.353 | 0.792 | 0.569 |
| 8 | 5.8 | 39.7 | 0.647 | 0.980 | 0.005 | 0.425 | 0.706 | 0.183 |
| 9 | 4.7 | 40.0 | 0.844 | 1.268 | 0.000 | 0.310 | 0.764 | 0.199 |
| 10 | 7.6 | 39.7 | 1.345 | 2.033 | 0.009 | 0.350 | 0.635 | 0.119 |
| 11 | 14.1 | 2.9 | 0.068 | 2.274 | 0.013 | na | na | na |
| 12 | 12.8 | 6.9 | 0.126 | 1.688 | 0.009 | na | na | na |
| 13 | 12.7 | 4.2 | 0.109 | 2.468 | 0.012 | 0.060 | 1.541 | 0.366 |
| 14 | 13.0 | 20.9 | 0.704 | 2.669 | 0.000 | 0.407 | 2.502 | 0.694 |
| 15 | 19.3 | 43.5 | 1.011 | 1.308 | 0.007 | 0.357 | 0.843 | 0.276 |
| 16 | 19.6 | 6.1 | 0.092 | 1.414 | 0.010 | 0.120 | 1.740 | 0.477 |
| 17 | 22.8 | 56.6 | 1.068 | 0.814 | 0.004 | 0.604 | 0.503 | 0.126 | na: no analysis/measurement

Example 24

Transfer of Pansy F3'5'H Gene (#40) and *Torenia* Anthocyanin 5-Acyltransferase Gene into WKS82

Plasmid pSPB130 (FIG. 7) was transferred into the pale violet rose variety "WKS82", and 89 transformants were obtained. Accumulation of delphinidin was confirmed in all 44 of the pigment-analyzed plants (Tables 25 and 26). The delphinidin content was 91% at maximum (average: 49%). The flower color was altered from RHS Color Chart 186d (Greyed-Purple group) to 80c (Purple-Violet group). However, no color of the Violet group, Violet-Blue group or Blue group according to the RHSCC was achieved and the target blue rose could not be obtained.

TABLE 25

| Plant No. | Acylation (%) | Del content (%) | Del (mg/g) | Cya (mg/g) | Pel (mg/g) | M (mg/g) | Q (mg/g) | K (mg/g) |
|---|---|---|---|---|---|---|---|---|
| 1 | 10.5 | 52.3 | 0.055 | 0.050 | 0.000 | 0.430 | 0.883 | 0.083 |
| 2 | 15.9 | 62.5 | 0.091 | 0.054 | 0.000 | 0.570 | 0.549 | 0.030 |
| 3 | 15.9 | 36.6 | 0.044 | 0.076 | 0.000 | 0.622 | 2.221 | 0.102 |
| 4 | 6.8 | 40.0 | 0.023 | 0.034 | 0.000 | 0.247 | 0.986 | 0.172 |
| 5 | 15.0 | 82.9 | 0.087 | 0.018 | 0.000 | 5.451 | 0.403 | 0.042 |
| 6 | na | 89.7 | 0.072 | 0.008 | 0.000 | 0.853 | 0.163 | 0.062 |
| 7 | 9.5 | 89.5 | 0.101 | 0.012 | 0.000 | 0.719 | 0.144 | 0.019 |
| 8 | 14.7 | 11.4 | 0.012 | 0.090 | 0.000 | na | na | na |
| 9 | 11.6 | 29.3 | 0.024 | 0.059 | 0.000 | na | na | na |
| 10 | 8.7 | 15.2 | 0.010 | 0.053 | 0.000 | na | na | na |
| 11 | 7.9 | 59.0 | 0.046 | 0.032 | 0.000 | 0.580 | 0.619 | 0.022 |
| 12 | 8.5 | 55.6 | 0.060 | 0.048 | 0.000 | 1.318 | 1.615 | 0.165 |
| 13 | 13.9 | 42.3 | 0.026 | 0.035 | 0.000 | 0.603 | 1.094 | 0.052 |
| 14 | 10.1 | 10.3 | 0.008 | 0.073 | 0.000 | na | na | na |
| 15 | 10.6 | 18.8 | 0.018 | 0.079 | 0.000 | na | na | na |
| 16 | 9.3 | 11.7 | 0.009 | 0.066 | 0.000 | na | na | na |
| 17 | 14.3 | 76.2 | 0.112 | 0.035 | 0.000 | 3.741 | 1.587 | 0.377 |
| 18 | 12.7 | 76.7 | 0.101 | 0.031 | 0.000 | 1.608 | 0.656 | 0.075 |
| 19 | 9.8 | 71.7 | 0.057 | 0.022 | 0.000 | 1.403 | 0.455 | 0.041 |
| 20 | 5.3 | 14.1 | 0.011 | 0.068 | 0.000 | 0.132 | 2.999 | 0.720 |
| 21 | 3.5 | 18.5 | 0.008 | 0.035 | 0.000 | na | na | na |
| 22 | 7.7 | 23.1 | 0.017 | 0.055 | 0.000 | 0.141 | 0.929 | 0.034 |
| 23 | 5.4 | 19.0 | 0.015 | 0.065 | 0.000 | 0.297 | 4.128 | 1.350 | na: no analysis/measurement

TABLE 26

| Plant No. | Acylation (%) | Del content (%) | Del (mg/g) | Cya (mg/g) | Pel (mg/g) | M (mg/g) | Q (mg/g) | K (mg/g) |
|---|---|---|---|---|---|---|---|---|
| 24 | 1.1 | 42.1 | 0.036 | 0.050 | 0.000 | 0.609 | 2.929 | 0.679 |
| 25 | 22.7 | 91.0 | 0.079 | 0.008 | 0.000 | 0.964 | 0.218 | 0.018 |
| 26 | 6.1 | 61.3 | 0.048 | 0.030 | 0.000 | 0.490 | 0.468 | 0.029 |
| 27 | 8.7 | 91.3 | 0.097 | 0.009 | 0.000 | 2.053 | 0.339 | 0.123 |
| 28 | 9.4 | 59.9 | 0.060 | 0.040 | 0.000 | 1.537 | 1.631 | 0.422 |
| 29 | 5.5 | 51.2 | 0.040 | 0.038 | 0.000 | 0.688 | 0.723 | 0.038 |
| 30 | 5.1 | 61.4 | 0.056 | 0.032 | 0.003 | 0.637 | 0.537 | 0.087 |
| 31 | 7.0 | 53.3 | 0.037 | 0.032 | 0.000 | 0.706 | 1.032 | 0.051 |
| 32 | 5.7 | 58.1 | 0.071 | 0.051 | 0.000 | 1.592 | 1.478 | 0.220 |
| 33 | 4.3 | 64.6 | 0.092 | 0.050 | 0.000 | 0.849 | 0.753 | 0.035 |
| 34 | 6.4 | 61.7 | 0.042 | 0.026 | 0.000 | 0.477 | 0.468 | 0.023 |
| 35 | 8.9 | 58.8 | 0.048 | 0.034 | 0.000 | 0.646 | 0.928 | 0.063 |
| 36 | 6.2 | 11.6 | 0.007 | 0.057 | 0.000 | 0.094 | 1.132 | 0.066 |
| 37 | 7.1 | 51.2 | 0.038 | 0.036 | 0.000 | 0.911 | 1.135 | 0.079 |
| 38 | 5.8 | 50.8 | 0.029 | 0.028 | 0.000 | 0.868 | 1.105 | 0.096 |
| 39 | 5.5 | 47.0 | 0.027 | 0.023 | 0.007 | 1.366 | 1.632 | 0.105 |
| 40 | 4.9 | 67.0 | 0.044 | 0.022 | 0.000 | 0.795 | 0.586 | 0.051 |
| 41 | na | 61.1 | 0.053 | 0.033 | 0.000 | 1.310 | 1.466 | 0.259 |
| 42 | 9.6 | 71.0 | 0.074 | 0.030 | 0.000 | 0.460 | 0.337 | 0.023 |
| 43 | 1.2 | 27.6 | 0.009 | 0.024 | 0.000 | na | na | na |
| 44 | 5.2 | 13.8 | 0.013 | 0.078 | 0.000 | na | na | na | na: no analysis/measurement

Example 25

Transfer of Pansy F3'5'H Gene (#40) and *Torenia* Anthocyanin 5-Acyltransferase Gene into WKS91

Plasmid pSPB130 (FIG. 7) was transferred into the light orange rose variety "WKS91", and 10 transformants were obtained. Accumulation of delphinidin was confirmed in only one of the two pigment-analyzed plants (Table 27). The delphinidin content was 2% at maximum. No alteration in flower color was observed from RHS Color Chart 43c (Red group).

TABLE 27

| Plant No. | Acylation (%) | Del content (%) | Del (mg/g) | Cya (mg/g) | Pel (mg/g) |
|---|---|---|---|---|---|
| 1 | 0.7 | 0.0 | 0.000 | 0.090 | 0.307 |
| 2 | 0.0 | 1.8 | 0.006 | 0.040 | 0.295 |

Example 26

Expression of Pansy F3'5'H Gene (#40) and Iris DFR Gene and Suppression of Rose Endogenous DFR Gene in Lavande RNA was obtained from blue iris petals of cut flowers, and polyA+RNA was prepared therefrom. A cDNA library was prepared from the polyA+RNA with λZAPII (Stratagene) as the vector, using a cDNA library preparation kit (Stratagene) according to the manufacturer's recommended protocol. An iris DFR gene fragment was prepared by the same method as reported for obtaining gentian DFR gene fragment (Tanaka et al. Plant Cell Physiol. 37, 711-716 1996).

The approximately 400 bp DNA fragment obtained was recovered with Gene Clean according to the manufacturer's recommended protocol, and was subcloned in pCR-TOPO. Determination of the nucleotide sequence revealed a sequence homologous to the rose DFR gene. The DNA fragment was used for screening of the iris cDNA library, and iris DFR cDNA including the full-length amino acid sequence was obtained. The total nucleotide sequence of the cDNA in the clone designated as pSPB906 was determined. The nucleotide sequence is listed as SEQ ID NO: 9, and the corresponding amino acid sequence is listed as SEQ ID NO: 10.

Next, an approximately 3.9 kb DNA fragment obtained by digestion of pSPB580 with BamHI and XhoI was linked with an approximately 1.5 kb DNA fragment obtained by digestion of pSPB906 with BamHI and XhoI, and the obtained plasmid was designated as pSPB909.

A vector for transcription of double-stranded RNA for the rose DFR cDNA in plants was prepared in the following manner. An approximately 3.5 kb DNA fragment (including Mac1 promoter, rose DFR cDNA and mas terminator) obtained by partial digestion of pCGP1364 (Tanaka et al., Plant Cell Physiol. (1995) 36, 1023-1031) with PstI was inserted at the PstI site of pUC19 (Yanisch-Perron C et al., Gene 33:103-119, 1985) to obtain plasmids, among which a plasmid having the HindIII site of pUC19 near the MacI promoter was designated as pCGP1394.

Next, an approximately 1.4 kb DNA fragment obtained by digestion of pCGP1394 with HindIII and SacII was ligated with an approximately 1.9 kb DNA fragment obtained by digestion of pCGP1394 with PstI, blunting of the ends and further digestion with SacII, and with a binary vector fragment obtained by digestion of pBinPLUS with SacI, blunting of the ends and further digestion with HindIII, to obtain pSPB185. Plasmid pSPB185 was digested with XbaI, blunted and ligated with a SalI linker to obtain pSPB521. An approximately 700 bp DNA fragment obtained by digestion of pUE6 with HindIII and BamHI was ligated with a binary vector DNA fragment obtained by digestion of pSPB521 with HindIII and SacI and with a GUS gene fragment obtained by digestion of pE2113 with BamHI and SacI, to obtain pSPB528.

Plasmid pSPB528 is a binary vector having a structural gene inserted between the enhancer-containing cauliflower mosaic virus 35S promoter and the manopine synthase terminator, which is expressible in plants. Also, in order to shorten the 5'-end non-translated sequence of rose DFR cDNA in pCGP645, plasmid pCGP645 was digested with SmaI and PvuI, blunted and re-ligated to obtain pCGP645s.

The 5'-end sequence of rose DFR cDNA was obtained by PCR amplification using pCGP645s as the template and a reverse primer and the synthetic primer RDF310 (5'-CCCTCGAGCCCTTGATGGCCTCGTCG-3') (SEQ ID NO: 19) as the primers, and was cloned in pCRTOPO. The DNA nucleotide sequence was determined and absence of errors by PCR was confirmed. This plasmid was designated as pSPB569. Also, a rose DFR cDNA 5'-end sequence with a different length was obtained by amplification using pCGP645s as the template and a reverse primer and the synthetic primer RDF830 (5'-GGGTCGACGCGGCCCTCTGCTTTCGG-3') (SEQ ID NO: 20) as the primers, and was cloned in pCR-TOPO. The DNA nucleotide sequence was determined and absence of errors by PCR was confirmed.

This plasmid was designated as pSPB570. A binary vector DNA fragment obtained by digestion of pSPB528 with BamHI and SacI, and an approximately 0.3 kb DNA fragment obtained by digestion of pSPB569 with SacI and XhoI, were ligated with a DNA fragment obtained by digestion of pSPB570 with BamHI and SalI, to obtain pSPB572. This vector is designed for transcription of double-stranded RNA for rose DFR cDNA in plants.

Plasmid pUE6 was digested with SacI and blunted, and a SalI linker was inserted to obtain pUE8. A DNA fragment obtained by digesting pUE8 with HindIII and EcoRI was introduced at the HindIII and EcoRI sites of pBinPLUS to obtain plasmid pSPB189. An approximately 3.7 kb DNA fragment obtained by digestion of pSPB189 with BamHI and SalI was ligated with an approximately 1.8 kb DNA fragment obtained by complete digestion of pCGP1961 with BamHI followed by partial digestion with XhoI, to obtain plasmid pSPB567. After PacI digestion and dephosphorylation treatment of pSPB572, it was linked with an approximately 2.8 kb DNA fragment obtained by digestion of pSPB567 with PacI, and a plasmid with transcription of the nptII gene and pansy F3'5'H #40 in the same direction was selected and designated as pSPB905.

Figure 8:
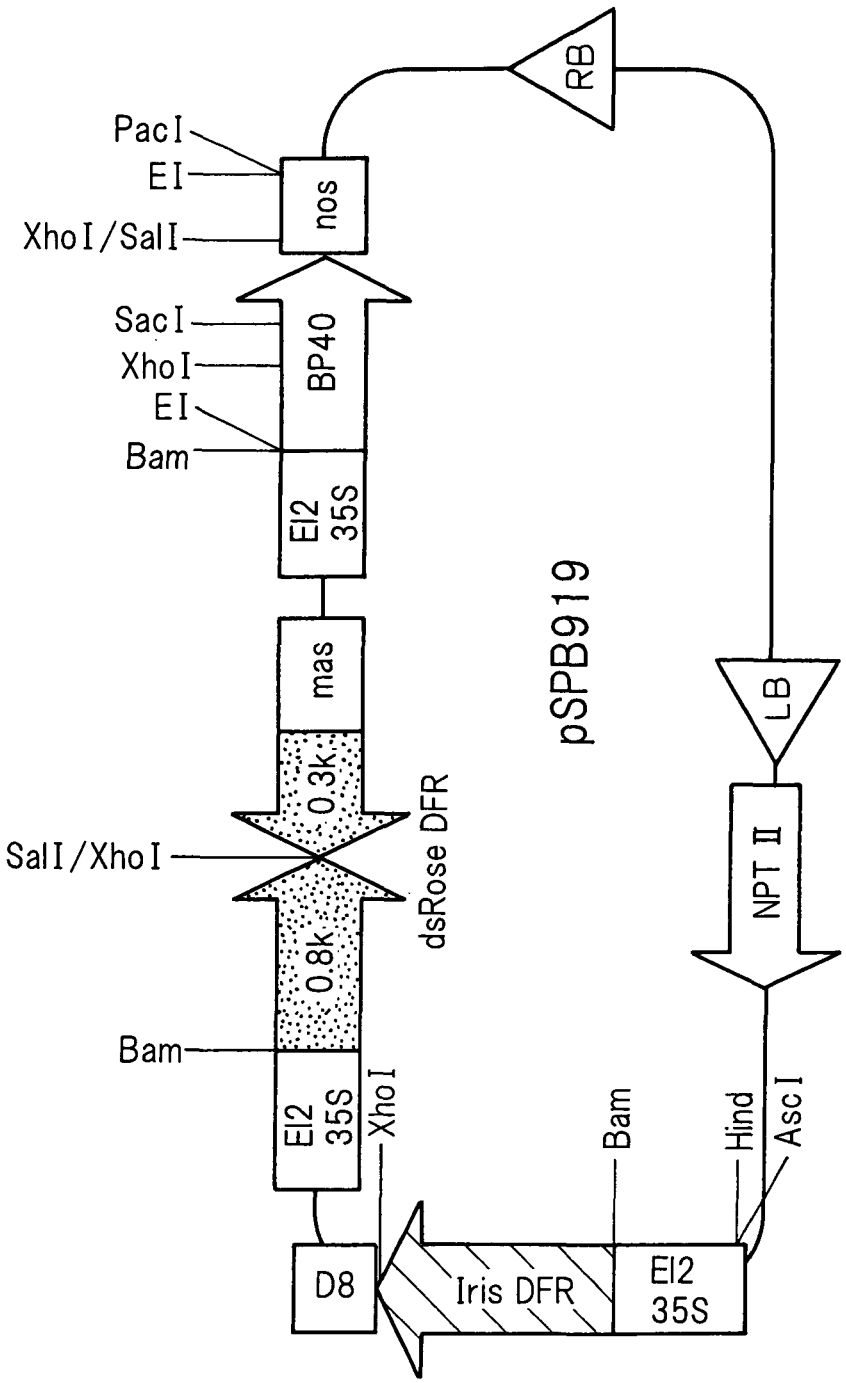
FIG. 8 shows the structure of plasmid pSPB919.

After AscI digestion and dephosphorylation treatment of pSPB905, it was linked with an approximately 2.5 kb DNA fragment obtained by digestion of pSPB909 with AscI, and a plasmid with transcription of the iris DFR gene in the same direction as the nptII gene was obtained and designated as pSPB919 (FIG. 8). This plasmid is expected to allow transcription of the iris DFR gene and pansy F3'S'H #40 gene in rose, while suppressing expression of the rose DFR gene due to transcription of double-stranded RNA. The plasmid was transferred into *Agrobacterium tumefaciens* Ag10.

Plasmid pSPB919 (FIG. 8) was transferred into the pale violet rose variety "Lavande", and 87 transformants were obtained. Accumulation of delphinidin was confirmed in 31 of the 38 pigment-analyzed plants (Tables 28 and 29). The delphinidin content was 100% at maximum (average: 76%). The flower color was altered from RHS Color Chart 186c (Greyed-Purple group) to 85a,b (Violet group).

RNA was extracted from rose petals in the same manner as explained above, and after separating the RNA by agarose gel electrophoresis, it was transferred onto Hybond N (Amersham) (for example, Tanaka et al., 1995). The mRNA was detected using a DIG Northern Starter Kit (Roche) by the manufacturer's recommended protocol. The rose DFR mRNA was detected using pCGP645 (Tanaka et al., Plant Cell Physiol. 36, 1023-1031, 1995) as template and a T7 primer transcript as the probe.

Detection of pansy F3'5'H #40 mRNA was accomplished using pCGP1961 as template and a T7 primer transcript as the probe. Detection of iris DFR mRNA was accomplished using pSPB906 as template and a T7 primer transcript as the probe. Pansy F3'5'H #40 and iris DFR gene mRNA were detected in the altered-color roses. On the other hand, rose DFR mRNA was significantly reduced compared to the host and a band was detected at the low molecular weight position, indicating decomposition of the rose DFR mRNA.

TABLE 28

| Plant No. | Del content (%) | Del (mg/g) | Cya (mg/g) | M (mg/g) | Q (mg/g) | K (mg/g) |
|---|---|---|---|---|---|---|
| 1 | 0.0 | 0.000 | 0.105 | 0.036 | 0.856 | 0.038 |
| 2 | 0.0 | 0.000 | 0.125 | na | na | na |

TABLE 28-continued

| Plant No. | Del content (%) | Del (mg/g) | Cya (mg/g) | M (mg/g) | Q (mg/g) | K (mg/g) |
|---|---|---|---|---|---|---|
| 3 | 0.0 | 0.000 | 0.091 | 0.023 | 0.851 | 0.101 |
| 4 | 0.0 | 0.000 | 0.116 | 0.000 | 1.336 | 0.087 |
| 5 | 0.0 | 0.000 | 0.048 | na | na | na |
| 6 | 88.5 | 0.086 | 0.011 | 1.626 | 1.187 | 0.411 |
| 7 | 90.8 | 0.089 | 0.009 | 0.797 | 1.548 | 0.087 |
| 8 | 84.0 | 0.046 | 0.009 | 0.163 | 0.699 | 0.016 |
| 9 | 87.8 | 0.062 | 0.009 | 0.193 | 0.760 | 0.022 |
| 10 | 89.3 | 0.072 | 0.009 | 0.210 | 0.575 | 0.033 |
| 11 | 91.5 | 0.049 | 0.005 | 0.398 | 0.805 | 0.050 |
| 12 | 91.5 | 0.032 | 0.003 | 0.100 | 0.811 | 0.014 |
| 13 | 85.7 | 0.040 | 0.007 | 0.092 | 0.497 | 0.012 |
| 14 | 64.9 | 0.040 | 0.021 | 0.263 | 0.327 | 0.015 |
| 15 | 88.3 | 0.041 | 0.005 | na | na | na |
| 16 | 66.4 | 0.011 | 0.006 | 0.036 | 1.221 | 0.030 |
| 17 | 79.7 | 0.008 | 0.002 | 0.030 | 0.765 | 0.009 |
| 18 | 100.0 | 0.010 | 0.000 | 0.048 | 1.343 | 0.067 |
| 19 | 95.9 | 0.040 | 0.002 | 0.159 | 0.136 | 0.004 |
| 20 | 65.4 | 0.016 | 0.008 | 0.090 | 1.244 | 0.048 |
| 21 | 18.8 | 0.011 | 0.049 | 0.048 | 0.855 | 0.020 |
| 22 | 0.0 | 0.000 | 0.110 | 0.000 | 1.274 | 0.079 |
| 23 | 0.0 | 0.000 | 0.140 | 0.000 | 1.952 | 0.200 | na: no analysis/measurement

TABLE 29

| Plant No. | Del content (%) | Del (mg/g) | Cya (mg/g) | M (mg/g) | Q (mg/g) | K (mg/g) |
|---|---|---|---|---|---|---|
| 24 | 41.4 | 0.102 | 0.144 | 0.265 | 0.417 | 0.015 |
| 25 | 34.3 | 0.042 | 0.081 | 0.167 | 0.429 | 0.024 |
| 26 | 34.6 | 0.023 | 0.043 | na | na | na |
| 27 | 41.4 | 0.082 | 0.116 | 0.232 | 0.385 | 0.019 |
| 28 | 37.7 | 0.046 | 0.076 | 0.254 | 0.429 | 0.018 |
| 29 | 36.1 | 0.032 | 0.057 | 0.151 | 0.235 | 0.042 |
| 30 | 97.2 | 0.052 | 0.002 | 0.208 | 0.088 | 0.004 |
| 31 | 93.0 | 0.038 | 0.003 | 0.347 | 0.137 | 0.007 |
| 32 | 98.2 | 0.101 | 0.002 | 0.339 | 0.258 | 0.029 |
| 33 | 91.3 | 0.039 | 0.004 | na | na | na |
| 34 | 91.9 | 0.041 | 0.004 | 0.332 | 0.120 | 0.007 |
| 35 | 96.8 | 0.052 | 0.002 | na | na | na |
| 36 | 96.7 | 0.084 | 0.003 | 0.342 | 0.168 | 0.010 |
| 37 | 88.0 | 0.014 | 0.002 | 0.076 | 1.000 | 0.029 |
| 38 | 84.5 | 0.016 | 0.003 | 0.074 | 1.121 | 0.025 | na: no analysis/measurement

Example 27

Expression of Pansy F3'5'H Gene (#40) and *Nierembergia* DFR gene, and Suppression of Rose Endogenous DFR gene in Lavande RNA was obtained from petals of the *Nierembergia hybrida* cultivar Fairy Bell Patio Light Blue (Suntory Flowers Co., Ltd.), and polyA⁺RNA was prepared therefrom. A cDNA library was prepared from the polyA⁺RNA with λZA-PII (Stratagene) as the vector, using a cDNA library synthesis kit (Stratagene) according to the manufacturer's recommended protocol. The cDNA library was screened using DIG-labeled petunia DFR cDNA (from pCGP1405).

The screening conditions were according to the plaque hybridization method using a DIG-labeling system, according to the manufacturer's recommended protocol. However, the formaldehyde concentration was 30% for the pre-hybridization and hybridization buffers, and hybridization was carried out overnight at 37° C. The membrane was rinsed at 55° C. in 5×SSC containing 1% SDS. Plasmids were recovered from 20 plaques among the numerous positive signals, and their nucleotide sequences were determined using Reverse Primer (Takara). These exhibited high homology with the DFR genes of other plants including petunia. The total nucleotide sequence of the cDNA in the clone designated as pSPB709 was determined. The nucleotide sequence is listed as SEQ ID NO: 11, and the corresponding amino acid sequence is listed as SEQ ID NO: 12

Figure 9:
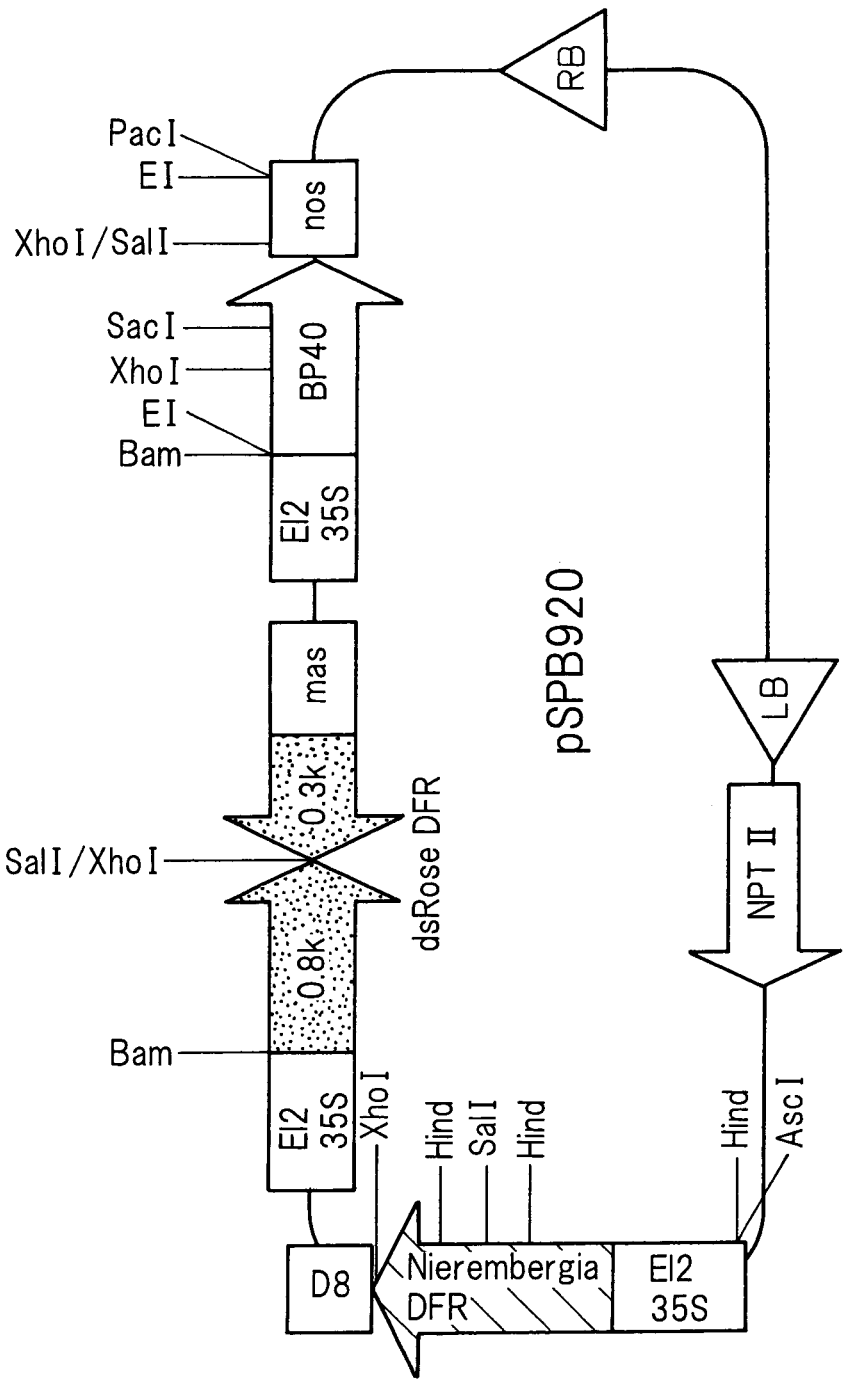
FIG. 9 shows the structure of plasmid pSPB920.

An approximately 3.9 kb DNA fragment obtained by digestion of pSPB580 with BamHI and XhoI was linked with an approximately 1.5 kb DNA fragment obtained by digestion of pSPB709 with BamHI and XhoI, to obtain plasmid pSPB910. After AscI digestion and dephosphorylation treatment of pSPB910, it was linked with an approximately 2.5 kb DNA fragment obtained by digestion of pSPB910 with AscI, and a plasmid with transcription of the *Nierembergia* DFR gene in the same direction as the nptII gene was obtained and designated as pSPB920 (FIG. 9). This plasmid is expected to allow transcription of the *Nierembergia* DFR gene and pansy F3'5'H #40 gene in rose, while suppressing expression of the rose DFR gene due to transcription of double-stranded RNA. The plasmid was transferred into *Agrobacterium tumefaciens* Ag10.

Plasmid pSPB920 (FIG. 9) was transferred into the pale violet rose variety "Lavande", and 56 transformants were obtained. Accumulation of delphinidin was confirmed in 23 of the 24 pigment-analyzed plants (Table 30). The delphinidin content was 100% at maximum (average: 43%). The flower color was altered from RHS Color Chart 186c (Greyed-Purple group) to 85b (Violet group).

TABLE 30

| Plant No. | Del content (%) | Del (mg/g) | Cya (mg/g) | M (mg/g) | Q (mg/g) | K (mg/g) |
|---|---|---|---|---|---|---|
| 1 | 69.5 | 0.025 | 0.002 | 0.081 | 2.265 | 0.066 |
| 2 | 85.4 | 0.024 | 0.004 | 0.114 | 1.355 | 0.032 |
| 3 | 71.8 | 0.006 | 0.002 | 0.043 | 0.781 | 0.027 |
| 4 | 100.0 | 0.012 | 0.000 | 0.414 | 0.283 | 0.030 |
| 5 | 88.2 | 0.015 | 0.002 | 0.506 | 0.126 | 0.030 |
| 6 | 100.0 | 0.013 | 0.000 | 0.430 | 0.123 | 0.008 |
| 7 | 33.3 | 0.019 | 0.038 | na | na | na |
| 8 | 37.3 | 0.012 | 0.020 | na | na | na |
| 9 | 48.2 | 0.012 | 0.013 | na | na | na |
| 10 | 18.9 | 0.011 | 0.049 | 0.053 | 1.023 | 0.022 |
| 11 | 39.7 | 0.037 | 0.056 | 0.120 | 1.157 | 0.035 |
| 12 | 9.4 | 0.010 | 0.095 | na | na | na |
| 13 | 11.0 | 0.008 | 0.062 | na | na | na |
| 14 | 24.4 | 0.017 | 0.054 | 0.128 | 1.852 | 0.181 |
| 15 | 12.4 | 0.015 | 0.102 | na | na | na |
| 16 | 89.7 | 0.089 | 0.010 | 0.530 | 1.424 | 0.165 |
| 17 | 15.4 | 0.006 | 0.035 | na | na | na |
| 18 | 22.3 | 0.006 | 0.019 | 0.018 | 1.286 | 0.038 |
| 19 | 10.4 | 0.007 | 0.058 | 0.039 | 1.673 | 0.045 |
| 20 | 28.3 | 0.006 | 0.015 | 0.028 | 0.932 | 0.025 |
| 21 | 35.2 | 0.015 | 0.028 | 0.105 | 0.743 | 0.028 |
| 22 | 16.0 | 0.010 | 0.052 | na | na | na |
| 23 | 0.0 | 0.000 | 0.018 | 0.013 | 1.764 | 0.027 |
| 24 | 13.7 | 0.007 | 0.042 | 0.033 | 1.469 | 0.041 | na: no analysis/measurement

Example 28

Inheritance of Traits to Progeny

Cross-breeding was carried out using a transformant (LA/919-2-13) obtained by transfer of pSPB919 (FIG. 8) into the pale violet rose variety "Lavande" as the pollen parent and non-recombinant WKS77 or WKS133 as the maternal parent (Suzuki, S., "Bara, Hanazufu", Shogakkann, p. 256-260, 1990). Fruit was collected on the 100th day after pollination. Seed production was accomplished by first peeling the fruit, harvesting the achene, peeling the achene, and then removing the germ and embedding it on moistened filter paper in a dish. The water used for seed production was sterilized water containing 1 ml/l PPM™ (Plant Preservative Mixture, Plant Cell Technology, Inc.) and 50 mg/l kanamycin, and seedlings were raised by potting only the normally budded plants.

Accumulation of delphinidin was confirmed in all 40 of the pigment-analyzed transformant progeny (Tables 31 and 32). The delphinidin content was 99% at maximum (average: 46%).

TABLE 31

| Plant No. | Del content (%) | Del (mg/g) | Cya (mg/g) | Pel (mg/g) | Peo (mg/g) |
|---|---|---|---|---|---|
| 1 | 89.8 | 0.494 | 0.056 | 0.000 | 0.000 |
| 2 | 96.1 | 3.900 | 0.153 | 0.005 | 0.000 |
| 3 | 55.9 | 0.836 | 0.660 | 0.000 | 0.000 |
| 4 | 24.6 | 0.041 | 0.127 | 0.000 | 0.000 |
| 5 | 23.5 | 1.108 | 3.605 | 0.009 | 0.002 |
| 6 | 25.9 | 0.191 | 0.545 | 0.003 | 0.000 |
| 7 | 0.5 | 0.013 | 2.552 | 0.012 | 0.002 |
| 8 | 75.8 | 0.283 | 0.090 | 0.000 | 0.000 |
| 9 | 95.9 | 1.420 | 0.061 | 0.000 | 0.000 |
| 10 | 30.8 | 0.862 | 1.841 | 0.007 | 0.105 |
| 11 | 13.3 | 0.068 | 0.441 | 0.004 | 0.000 |
| 12 | 23.9 | 0.529 | 1.667 | 0.023 | 0.000 |
| 13 | 43.7 | 0.280 | 0.362 | 0.000 | 0.000 |
| 14 | 19.3 | 0.035 | 0.145 | 0.000 | 0.000 |
| 15 | 0.6 | 0.008 | 1.418 | 0.021 | 0.000 |
| 16 | 20.8 | 0.048 | 0.183 | 0.000 | 0.000 |
| 17 | 92.5 | 2.257 | 0.177 | 0.007 | 0.000 |
| 18 | 66.4 | 2.496 | 1.247 | 0.015 | 0.000 |
| 19 | 42.4 | 0.369 | 0.497 | 0.004 | 0.000 |
| 20 | 75.6 | 0.597 | 0.183 | 0.010 | 0.000 |
| 21 | 19.6 | 0.271 | 1.103 | 0.008 | 0.000 |
| 22 | 71.0 | 0.107 | 0.044 | 0.000 | 0.000 |
| 23 | 0.6 | 0.006 | 0.850 | 0.004 | 0.000 |

TABLE 32

| Plant No. | Del content (%) | Del (mg/g) | Cya (mg/g) | Pel (mg/g) | Peo (mg/g) |
|---|---|---|---|---|---|
| 24 | 16.7 | 0.053 | 0.263 | 0.000 | 0.000 |
| 25 | 71.8 | 0.211 | 0.083 | 0.000 | 0.000 |
| 26 | 18.6 | 0.177 | 0.769 | 0.003 | 0.000 |
| 27 | 1.3 | 0.009 | 0.652 | 0.004 | 0.000 |
| 28 | 59.7 | 0.183 | 0.124 | 0.000 | 0.000 |
| 29 | 39.6 | 0.124 | 0.187 | 0.003 | 0.000 |
| 30 | 21.4 | 0.187 | 0.684 | 0.003 | 0.000 |
| 31 | 0.6 | 0.005 | 0.763 | 0.004 | 0.000 |
| 32 | 38.8 | 0.226 | 0.353 | 0.003 | 0.000 |
| 33 | 50.5 | 0.154 | 0.151 | 0.000 | 0.000 |
| 34 | 28.0 | 0.267 | 0.682 | 0.003 | 0.000 |
| 35 | 83.9 | 0.204 | 0.039 | 0.000 | 0.000 |
| 36 | 64.9 | 0.380 | 0.205 | 0.000 | 0.000 |
| 37 | 78.8 | 0.239 | 0.064 | 0.000 | 0.000 |
| 38 | 97.4 | 0.614 | 0.016 | 0.000 | 0.000 |
| 39 | 98.7 | 0.805 | 0.011 | 0.000 | 0.000 |
| 40 | 54.9 | 0.083 | 0.068 | 0.000 | 0.000 |

Example 29

Expression of Pansy F3'5'H #40 Gene and Iris DFR Gene and Suppression of Rose Endogenous DFR Gene in WKS140

Plasmid pSPB919 was transferred into the pale violet rose variety "WKS140", and 89 transformants were obtained. Accumulation of delphinidin was confirmed in 74 of the 79 pigment-analyzed plants. The delphinidin content was 100% at maximum (average: 68%). The flower color was altered from RHS Color Chart 186d (Greyed-Purple group) to primarily 84c (Violet group).

TABLE 33

| Plant No. | Del (%) | Del (mg/g) | Cya (mg/g) | Pel (mg/g) |
|---|---|---|---|---|
| 1 | 0.0% | 0.0000 | 0.0423 | 0.0000 |
| 2 | 89.9% | 0.0242 | 0.0027 | na |
| 3 | 90.0% | 0.0245 | 0.0027 | na |
| 4 | 88.6% | 0.0093 | 0.0012 | na |
| 5 | 43.5% | 0.0042 | 0.0054 | na |
| 6 | 91.2% | 0.0118 | 0.0011 | na |
| 7 | 81.2% | 0.0027 | 0.0006 | na |
| 8 | 81.0% | 0.0173 | 0.0041 | na |
| 9 | 73.9% | 0.0733 | 0.0259 | na |
| 10 | 62.9% | 0.0321 | 0.0190 | na |
| 11 | 91.9% | 0.0962 | 0.0084 | na |
| 12 | 99.1% | 0.1606 | 0.0015 | na |
| 13 | 94.7% | 0.0588 | 0.0033 | na |
| 14 | 100.0% | 0.0839 | 0.0000 | na |
| 15 | 0.0% | 0.0000 | 0.0005 | na |
| 16 | 98.4% | 0.0296 | 0.0005 | na |
| 17 | 80.4% | 0.1748 | 0.0451 | na |
| 18 | 94.6% | 0.0190 | 0.0000 | na |
| 19 | 0.0% | 0.0000 | 0.0714 | na |
| 20 | 34.3% | 0.0099 | 0.0191 | na |
| 21 | 30.9% | 0.0126 | 0.0282 | na |
| 22 | 65.6% | 0.0294 | 0.0154 | na |
| 23 | 24.1% | 0.0205 | 0.0646 | na | na: no analysis/measurement

Example 30

Expression of Pansy F3'5'H #40 Gene and Iris DFR Gene and Suppression of Rose Endogenous DFR Gene in WKS77

Plasmid pSPB919 was transferred into the dark red-purple rose variety "WKS77", and 50 transformants were obtained. Accumulation of delphinidin was confirmed in 21 of the 23 pigment-analyzed plants. The delphinidin content was 81% at maximum (average: 19%). The flower color was altered from RHS Color Chart 57a (Red-Purple group) to 77b (Purple group).

TABLE 34

| Plant No. | Del (%) | Del (mg/g) | Cya (mg/g) | Pel (mg/g) |
|---|---|---|---|---|
| 1 | 26.0% | 1.2028 | 3.4033 | 0.0117 |
| 2 | 41.5% | 0.6473 | 0.9093 | 0.0048 |
| 3 | 80.8% | 0.2210 | 0.0526 | na |
| 4 | 68.0% | 0.1865 | 0.0878 | na |
| 5 | 68.5% | 0.2090 | 0.0951 | 0.0010 |
| 6 | 1.5% | 0.0119 | 0.7731 | 0.0051 |
| 7 | 1.5% | 0.0114 | 0.7304 | 0.0041 |
| 8 | 0.2% | 0.0069 | 2.9266 | 0.0063 |
| 9 | 0.2% | 0.0017 | 1.0791 | 0.0062 |
| 10 | 0.0% | 0.0000 | 0.5013 | 0.0043 |

TABLE 34-continued

| Plant No. | Del (%) | Del (mg/g) | Cya (mg/g) | Pel (mg/g) |
|---|---|---|---|---|
| 11 | 0.1% | 0.0028 | 2.3418 | 0.0110 |
| 12 | 0.4% | 0.0091 | 2.4603 | 0.0126 |
| 13 | 0.2% | 0.0040 | 1.7766 | 0.0096 |
| 14 | 0.3% | 0.0026 | 0.9046 | 0.0052 |
| 15 | 0.0% | 0.0000 | 1.6063 | 0.0100 |
| 16 | 22.2% | 0.3279 | 1.1392 | 0.0049 |
| 17 | 24.0% | 0.2638 | 0.8288 | 0.0052 |
| 18 | 1.4% | 0.0240 | 1.6777 | 0.0118 |
| 19 | 1.1% | 0.0186 | 1.6352 | 0.0101 |
| 20 | 26.7% | 0.2645 | 0.7230 | 0.0037 |
| 21 | 22.7% | 0.2200 | 0.7460 | 0.0046 |
| 22 | 40.1% | 0.8929 | 1.3374 | 0.0071 | na: no analysis/measurement

Example 31

Expression of Pansy F3'5'H #40 Gene and *Nierembergia* DFR Gene and Suppression of Rose Endogenous DFR Gene in WKS77

Plasmid pSPB920 was transferred into the dark red-purple rose variety "WKS77", and 30 transformants were obtained. Accumulation of delphinidin was confirmed in 26 of the 27 pigment-analyzed plants. The delphinidin content was 98% at maximum (average: 60%). The flower color was altered from RHS Color Chart 57a (Red-Purple group) to 77b (Purple group).

TABLE 35

| Plant No. | Del (%) | Del (mg/g) | Cya (mg/g) | Pel (mg/g) |
|---|---|---|---|---|
| 1 | 93.9% | 0.1679 | 0.0110 | 0.0000 |
| 2 | 97.6% | 0.2311 | 0.0058 | na |
| 3 | 96.3% | 0.1684 | 0.0065 | na |
| 4 | 97.1% | 0.1012 | 0.0017 | na |
| 5 | 9.6% | 0.0946 | 0.7810 | 0.1104 |
| 6 | 21.9% | 0.1462 | 0.5166 | 0.0034 |
| 7 | 12.7% | 0.1097 | 0.7495 | 0.0049 |
| 8 | 97.9% | 0.1942 | 0.0042 | na |
| 9 | 98.1% | 0.1228 | 0.0024 | na |
| 10 | 3.2% | 0.0360 | 1.0689 | 0.0035 |
| 11 | 3.1% | 0.0267 | 0.9587 | 0.0032 |
| 12 | 4.8% | 0.1138 | 2.2562 | 0.0049 |
| 13 | 6.2% | 0.1066 | 1.5999 | 0.0080 |
| 14 | 96.5% | 0.3541 | 0.0132 | na |
| 15 | 2.1% | 0.0173 | 0.7852 | 0.0068 |
| 16 | 94.7% | 0.2898 | 0.0160 | 0.0000 |
| 17 | 96.7% | 0.0819 | 0.0020 | 0.0000 |
| 18 | 95.8% | 0.6969 | 0.0309 | na |
| 19 | 96.4% | 0.4868 | 0.0181 | na |
| 20 | 64.3% | 0.3092 | 0.1724 | na |
| 21 | 26.9% | 0.2740 | 0.7431 | 0.0025 |
| 22 | 19.9% | 0.3760 | 1.5028 | 0.0071 |
| 23 | 88.2% | 0.0316 | 0.0042 | na |
| 24 | 94.2% | 0.0259 | 0.0016 | na |
| 25 | 90.4% | 0.0481 | 0.0051 | na | na: no analysis/measurement

Example 32

Expression of Pansy F3'5'H#40 Gene and Petunia DFR Gene and Suppression of Rose Endogenous DFR Gene in WKS77

Plasmid pSPB921 was transferred into the dark red-purple rose variety "WKS77", and 15 transformants were obtained. Accumulation of delphinidin was confirmed in 12 of the 13 pigment-analyzed plants. The delphinidin content was 98% at maximum (average: 60%). The flower color was altered from RHS Color Chart 57a (Red-Purple group) to 72b (Red-Purple group).

TABLE 36

| Plant No. | Del (%) | Del (mg/g) | Cya (mg/g) | Pel (mg/g) |
|---|---|---|---|---|
| 1 | 90.0% | 0.0549 | 0.0061 | na |
| 2 | 38.4% | 0.3397 | 0.5402 | 0.0041 |
| 3 | 56.9% | 0.7834 | 0.5824 | 0.0099 |
| 4 | 58.5% | 0.0196 | 0.0139 | na |
| 5 | 90.3% | 0.1336 | 0.0144 | na |
| 6 | 90.9% | 0.1251 | 0.0126 | na |
| 7 | 86.7% | 0.1771 | 0.0274 | na |
| 8 | 91.6% | 0.0113 | 0.0010 | na |
| 9 | 97.5% | 0.0864 | 0.0022 | na |
| 10 | 9.5% | 0.2687 | 2.6591 | 0.0000 |
| 11 | 8.8% | 0.1421 | 1.4598 | 0.0071 |
| 12 | 0.4% | 0.0060 | 1.3554 | 0.0053 | na: no analysis/measurement

Example 33

Inheritance of Traits to Progeny

Cross-breeding was carried out in the same manner as Example 28, using a transformant (LA/919-4-10) obtained by transfer of pSPB919 into the pale violet rose variety "Lavande" as the pollen parent and the non-recombinant rose variety "Black Baccara" as the maternal parent. Fruit was collected on the 100th day after pollination. Seed production was accomplished by first peeling the fruit, harvesting the achene, peeling the achene, and then removing the germ and embedding it on moistened filter paper in a dish. The water used for seed production was sterilized water containing 1 ml/l PPM™ (Plant Preservative Mixture, Plant Cell Technology, Inc.) and 50 mg/l kanamycin, and seedlings were raised by potting only the normally budded plants.

Accumulation of delphinidin was confirmed in all 18 of the pigment-analyzed transformant progeny. The delphinidin content was 99.8% at maximum (average: 98.7%).

TABLE 37

| Plant No. | Del (%) | Del (mg/g) | Cya (mg/g) | Pel (mg/g) |
|---|---|---|---|---|
| 1 | 97.8% | 0.6633 | 0.0142 | 0.0009 |
| 2 | 99.0% | 0.9002 | 0.0096 | na |
| 3 | 98.5% | 0.5385 | 0.0080 | na |
| 4 | 99.5% | 2.0561 | 0.0087 | 0.0016 |
| 5 | 99.8% | 1.6556 | 0.0034 | na |
| 6 | 96.6% | 0.5601 | 0.0200 | na |
| 7 | 99.0% | 0.6148 | 0.0063 | na |
| 8 | 98.9% | 1.6867 | 0.0193 | na |
| 9 | 95.0% | 0.5740 | 0.0304 | na |
| 10 | 96.9% | 0.1152 | 0.0036 | na |
| 11 | 99.3% | 0.0683 | 0.0005 | na |
| 12 | 99.6% | 0.1248 | 0.0005 | na |
| 13 | 99.5% | 0.3574 | 0.0010 | 0.0000 |
| 14 | 99.6% | 0.5500 | 0.0021 | na |
| 15 | 99.6% | 1.2322 | 0.0049 | na |
| 16 | 99.7% | 1.4384 | 0.0042 | na |
| 17 | 99.8% | 0.5117 | 0.0010 | na |
| 18 | 98.3% | 0.8073 | 0.0140 | na | na: no analysis/measurement

Example 34

Expression of Pansy F3'5'H #40 Gene and Suppression of Rose Endogenous F3'H Gene in WKS77

Figure 10:
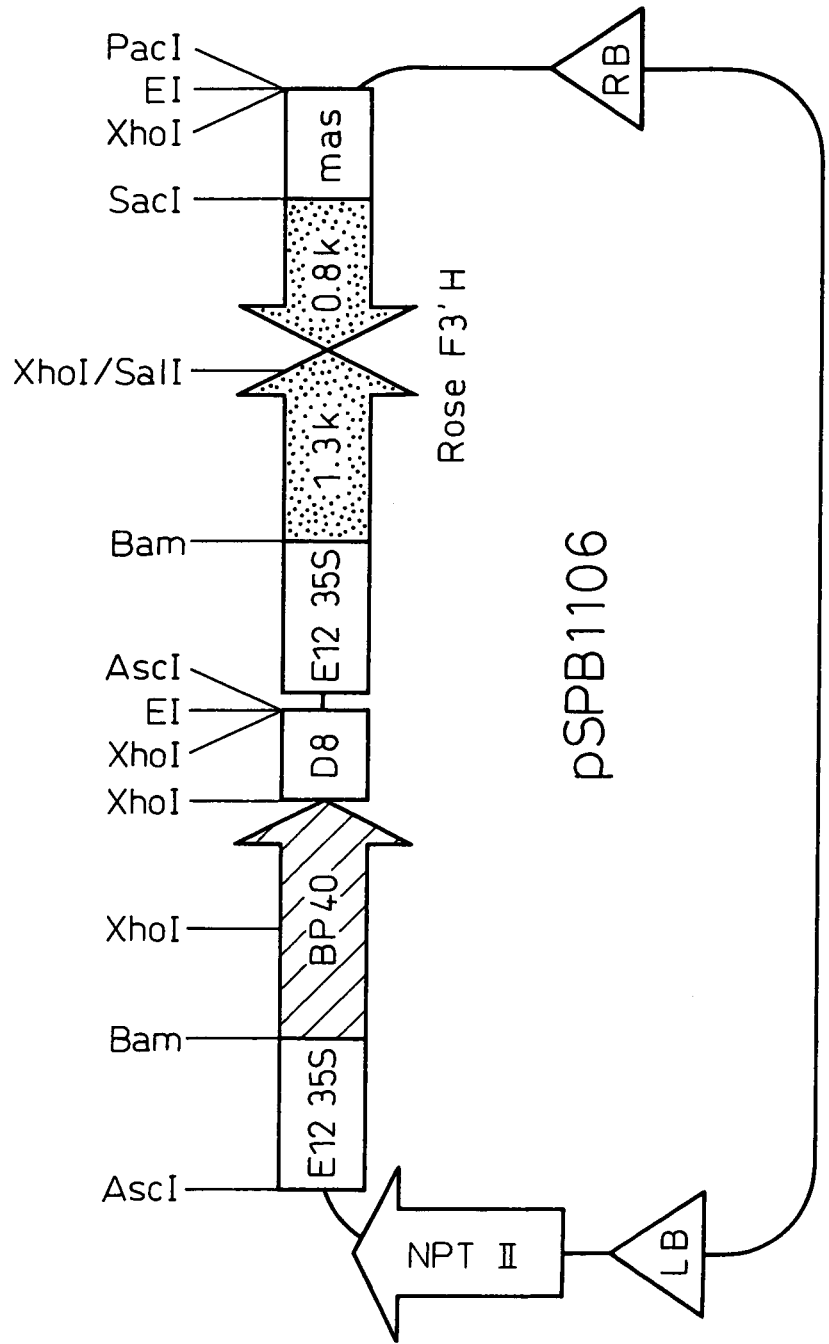
FIG. 10 shows the structure of plasmid pSPB1106.

Plasmid pSPB1106 (FIG. 10) was transferred into the dark red-purple rose variety "WKS77", and 40 transformants were obtained. Accumulation of delphinidin was confirmed in all 26 of the pigment-analyzed plants. The delphinidin content was 80.0% at maximum (average: 30.5%). The flower color underwent a major alteration from RHS Color Chart 57a (Red-Purple group) to 83d (Violet group).

TABLE 38

| Plant No. | Del (%) | Del (mg/g) | Cya (mg/g) | Pel (mg/g) | M (mg/g) | Q (mg/g) | K (mg/g) |
|---|---|---|---|---|---|---|---|
| 1 | 68.7% | 0.5497 | 0.2275 | 0.0241 | na | na | na |
| 2 | 78.8% | 0.3449 | 0.0830 | 0.0096 | na | na | na |
| 3 | 80.0% | 0.6949 | 0.1604 | 0.0144 | na | na | na |
| 4 | 71.2% | 0.4377 | 0.1563 | 0.0214 | na | na | na |
| 5 | 72.7% | 0.5260 | 0.1715 | 0.0266 | 0.3812 | 0.2275 | 1.7669 |
| 6 | 70.7% | 0.3829 | 0.1449 | 0.0146 | na | na | na |
| 7 | 10.3% | 0.0358 | 0.3031 | 0.0071 | na | na | na |
| 8 | 15.6% | 0.1847 | 0.9530 | 0.0444 | na | na | na |
| 9 | 4.8% | 0.0739 | 1.4586 | 0.0149 | na | na | na |
| 10 | 1.1% | 0.0114 | 1.0411 | 0.0144 | na | na | na |
| 11 | 54.0% | 1.3206 | 1.1166 | 0.0092 | na | na | na |
| 12 | 57.8% | 0.8842 | 0.6410 | 0.0056 | na | na | na |
| 13 | 0.9% | 0.0242 | 2.5500 | 0.0168 | na | na | na |
| 14 | 23.0% | 0.2087 | 0.6909 | 0.0062 | na | na | na |
| 15 | 12.7% | 0.1645 | 1.1271 | 0.0058 | na | na | na |
| 16 | 26.4% | 0.5275 | 1.4645 | 0.0132 | na | na | na |
| 17 | 18.7% | 0.3555 | 1.5310 | 0.0109 | na | na | na |
| 18 | 24.2% | 0.4388 | 1.3687 | 0.0072 | na | na | na |
| 19 | 64.7% | 0.4029 | 0.1945 | 0.0249 | 0.6368 | 0.3949 | 2.0567 |
| 20 | 0.1% | 0.0021 | 1.8646 | 0.0077 | na | na | na |
| 21 | 0.0% | 0.0000 | 0.9708 | 0.0062 | na | na | na |
| 22 | 0.1% | 0.0022 | 2.6049 | 0.0127 | na | na | na |
| 23 | 0.4% | 0.0066 | 1.8002 | 0.0066 | na | na | na |
| 24 | 0.5% | 0.0079 | 1.4670 | 0.0056 | 0.0000 | 1.3096 | 0.2414 |
| 25 | 17.3% | 0.1000 | 0.4671 | 0.0099 | na | na | na |
| 26 | 18.3% | 0.1232 | 0.5418 | 0.0052 | na | na | na | na: no analysis/measurement

Example 35

Expression of Pansy F3'5'H #40 Gene and Suppression of Rose Endogenous F3'H Gene in Lavande Plasmid pSPB1106 was transferred into the pale violet rose variety "Lavande", and 40 transformants were obtained. Accumulation of delphinidin was confirmed in 23 of the 25 pigment-analyzed plants. The delphinidin content was 98.3% at maximum (average: 46.9%).

TABLE 39

| Plant No. | Del (%) | Del (mg/g) | Cya (mg/g) | Pel (mg/g) | M (mg/g) | Q (mg/g) | K (mg/g) |
|---|---|---|---|---|---|---|---|
| 1 | 76.8% | 0.0732 | 0.0188 | 0.0032 | 0.5705 | 0.1595 | 0.3073 |
| 2 | 80.1% | 0.1441 | 0.0296 | 0.0061 | 0.5298 | 0.1881 | 4.3294 |
| 3 | 3.7% | 0.0086 | 0.2174 | 0.0027 | na | na | na |
| 4 | 4.4% | 0.0079 | 0.1691 | 0.0034 | na | na | na |
| 5 | 8.8% | 0.0158 | 0.1557 | 0.0070 | na | na | na |
| 6 | 39.0% | 0.0212 | 0.0128 | 0.0204 | 0.0000 | 0.0363 | 1.3107 |
| 7 | 44.4% | 0.0089 | 0.0027 | 0.0084 | 0.0756 | 0.0573 | 1.3689 |
| 8 | 40.4% | 0.0165 | 0.0071 | 0.0172 | 0.0365 | 0.0592 | 2.5211 |
| 9 | 42.0% | 0.0087 | 0.0036 | 0.0084 | 0.0752 | 0.0596 | 1.2661 |
| 10 | 13.5% | 0.0153 | 0.0939 | 0.0040 | 0.1288 | 1.0594 | 0.5440 |
| 11 | 81.6% | 0.2252 | 0.0447 | 0.0061 | 0.3947 | 0.1401 | 0.3947 |
| 12 | 78.8% | 0.1022 | 0.0239 | 0.0036 | 0.6700 | 0.2137 | 0.5847 |
| 13 | 81.7% | 0.2125 | 0.0438 | 0.0036 | 1.3616 | 0.4621 | 0.7478 |
| 14 | 80.9% | 0.1829 | 0.0388 | 0.0044 | 0.4100 | 0.2405 | 0.0567 |
| 15 | 70.9% | 0.0664 | 0.0204 | 0.0069 | 0.4230 | 0.1221 | 0.1788 |
| 16 | 0.0% | 0.0000 | 0.0844 | 0.0000 | na | na | na |
| 17 | 98.0% | 0.2363 | 0.0048 | 0.0000 | 0.0000 | 1.0613 | 0.2698 |
| 18 | 98.3% | 0.1398 | 0.0025 | 0.0000 | 0.0479 | 0.7060 | 0.1299 |
| 19 | 4.2% | 0.0078 | 0.1724 | 0.0040 | 0.0000 | 0.8627 | 0.2075 |
| 20 | 0.0% | 0.0000 | 0.1696 | 0.0043 | na | na | na |
| 21 | 60.0% | 0.0333 | 0.0115 | 0.0107 | 0.0000 | 0.0740 | 1.8678 |
| 22 | 14.3% | 0.0091 | 0.0454 | 0.0088 | 0.1096 | 0.5305 | 0.6453 |
| 23 | 15.1% | 0.0082 | 0.0408 | 0.0053 | na | na | na |
| 24 | 17.6% | 0.0082 | 0.0324 | 0.0059 | na | na | na |
| 25 | 24.4% | 0.0147 | 0.0375 | 0.0080 | 0.0000 | 0.2147 | 0.9765 | na: no analysis/measurement

These results demonstrate that the transferred exogenous gene was inherited and expressed by the progeny, and that the trait of delphinidin production which is not found in ordinary rose petals was successfully inherited by the rose progeny. Thus, this gene can be used for cross-breeding cultivation of roses with altered colors to create roses with new colors including blue and purple.

INDUSTRIAL APPLICABILITY

By artificially suppressing function of the endogenous metabolic pathway such as, for example, expression of dihydroflavonol reductase, in rose, and expressing the gene coding for pansy flavonoid 3',5'-hydroxylase and a gene coding for dihydroflavonol reductase from species other than rose, it is possible to create blue to violet roses. These genes are inherited by subsequent generations, and the blue rose trait can be utilized for cross-breeding.

---

What is claimed is:

1. A method for producing a rose, comprising:
   artificially suppressing a rose flavonoid synthesis pathway by artificially suppressing expression of either a rose endogenous dihydroflavonol reductase (DFR) using a double-stranded RNA (dsRNA) of the DFR gene or a rose endogenous flavonoid 3'-hydroxylase (F3'H) using a dsRNA of the F3'H gene; and
   expressing a pansy gene coding for flavonoid 3',5'-hydroxylase (F3'5'H) having the nucleotide sequence of SEQ ID NO: 1 or SEQ ID NO: 3.

2. The method for producing a rose according to claim 1, further comprising expressing a gene coding for dihydroflavonol reductase derived from a plant other than rose.

3. The method for producing a rose according to claim 1, wherein the plant other than rose is selected from the group consisting of iris, *Nierembergia*, and petunia.

4. The rose obtained by the method according to any one of claim 1, 2, or 3, or a progeny or a tissue thereof, the progeny or the tissue comprising the dsRNA of the DFR gene or the dsRNA of the F3'H gene and the pansy gene coding for F3'5'H, having the nucleotide sequence of SEQ ID NO: 1 or SEQ ID NO: 3.

5. The rose, progeny, or tissue thereof, according to claim 4, wherein the petal color of the rose is violet.

6. The rose, progeny, or tissue thereof, according to claim 4, wherein the petal color of the rose belongs to the "Violet group", according to the Royal Horticultural Society Colour Chart (RHSCC).

7. The rose, progeny, or tissue thereof, according to claim 4, wherein the petal color of the rose belongs to "Violet group" 85a or 85b according to the Royal Horticultural Society Colour Chart (RHSCC).

8. A method for producing a rose, comprising:
   artificially suppressing a rose flavonoid synthesis pathway by artificially suppressing expression of a rose endogenous dihydroflavonol reductase (DFR) using a dsRNA of the DFR gene;
   expressing a pansy gene coding for flavonoid 3',5'-hydroxylase (F3'5'H) having the nucleotide sequence of SEQ ID NO: 1 or SEQ ID NO: 3; and
   expressing a gene coding for a dihydroflavonol reductase derived from a plant other than rose.

9. The method for producing a rose according to claim 8, wherein the plant other than rose is selected from the group consisting of iris, *Nierembergia*, and petunia.

10. The rose obtained by the method according to claim 8, or a progeny or a tissue thereof, the progeny or the tissue comprising the dsRNA of the DFR gene and the pansy gene coding for F3'5'H having the nucleotide sequence of SEQ ID NO: 1 or SEQ ID NO: 3.

11. The rose, the progeny, or the tissue thereof, according to claim 10, wherein the petal color of the rose is violet.

12. The rose, the progeny, or the tissue according to claim 10, wherein the petal color of the rose belongs to the "Violet group", according to the Royal Horticultural Society Colour Chart (RHSCC).

13. The rose, or progeny or tissue thereof, according to claim 10, wherein the petal color of the rose belongs to "Violet group" 85a or 85b according to the Royal Horticultural Society Colour Chart (RHSCC).

* * * * *

UNITED STATES PATENT AND TRADEMARK OFFICE
CERTIFICATE OF CORRECTION

PATENT NO.          : 8,410,335 B2                       Page 1 of 1
APPLICATION NO.     : 10/567931
DATED               : April 2, 2013
INVENTOR(S)         : Yoshikazu Tanaka et al.

It is certified that error appears in the above-identified patent and that said Letters Patent is hereby corrected as shown below:

In the Claims

Column 69, Claim 3, line 35          Delete "claim 1"
                                     Insert -- claim 2 --

Column 69, Claim 4, line 39          Delete "claim"
                                     Insert -- claims --

Column 69, Claim 4, line 41          After "F3'H gene"
                                     Insert -- , --

Column 70, Claim 12, line 43         After "tissue"
                                     Insert -- thereof, --

Signed and Sealed this
Fourth Day of February, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,410,335 B2
APPLICATION NO. : 10/567931
DATED : April 2, 2013
INVENTOR(S) : Tanaka et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2061 days.

Signed and Sealed this
First Day of September, 2015

Michelle K. Lee
*Director of the United States Patent and Trademark Office*